(12) United States Patent
Romanov et al.

(10) Patent No.: US 12,351,871 B2
(45) Date of Patent: Jul. 8, 2025

(54) SUBSTITUTED COUMARIN DYES AND USES AS FLUORESCENT LABELS

(71) Applicant: Illumina Cambridge Limited, Cambridge (GB)

(72) Inventors: Nikolai Nikolaevich Romanov, Cambridge (GB); Michael Callingham, Cambridge (GB); Carole Anastasi, Cambridge (GB); Patrick McCauley, Cambridge (GB); Niall Hynes, Cambridge (GB); Natasha Crake, Cambridge (GB); Xiaolin Wu, Cambridge (GB); Xiaohai Liu, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 0 days.

(21) Appl. No.: 18/630,722

(22) Filed: Apr. 9, 2024

(65) Prior Publication Data
US 2024/0271209 A1    Aug. 15, 2024

Related U.S. Application Data

(62) Division of application No. 17/385,232, filed on Jul. 26, 2021, now Pat. No. 11,981,964.

(60) Provisional application No. 63/057,758, filed on Jul. 28, 2020.

(51) Int. Cl.
| | | |
|---|---|---|
| C12Q 1/68 | (2018.01) | |
| C07D 405/14 | (2006.01) | |
| C07D 407/02 | (2006.01) | |
| C07D 407/04 | (2006.01) | |
| C07D 409/04 | (2006.01) | |
| C07D 409/14 | (2006.01) | |
| C07D 413/04 | (2006.01) | |
| C07D 417/04 | (2006.01) | |
| C07D 417/14 | (2006.01) | |
| C09B 57/02 | (2006.01) | |
| C12Q 1/6869 | (2018.01) | |
| C12Q 1/6876 | (2018.01) | |
| G01N 21/64 | (2006.01) | |

(52) U.S. Cl.
CPC ......... *C12Q 1/6876* (2013.01); *C07D 405/14* (2013.01); *C07D 407/02* (2013.01); *C07D 407/04* (2013.01); *C07D 409/04* (2013.01); *C07D 409/14* (2013.01); *C07D 413/04* (2013.01); *C07D 417/04* (2013.01); *C07D 417/14* (2013.01); *C09B 57/02* (2013.01); *C12Q 1/6869* (2013.01); *G01N 21/6428* (2013.01); *G01N 2021/6439* (2013.01)

(58) Field of Classification Search
CPC .. C07D 405/14; C07D 407/04; C07D 409/04; C07D 409/14; C07D 413/04; C07D 417/04; C07D 417/14; C07D 405/02; C07D 407/02; C07D 409/02; C07D 421/02; C07H 19/10; C07H 19/14; C12Q 1/6876; C12Q 1/6869
See application file for complete search history.

(56) References Cited

U.S. PATENT DOCUMENTS

| | | | |
|---|---|---|---|
| 4,404,389 | A | 9/1983 | Vamvakaris |
| 5,268,486 | A | 12/1993 | Waggoner et al. |
| 5,302,509 | A | 4/1994 | Cheeseman |
| 5,429,807 | A | 7/1995 | Matson et al. |
| 5,436,327 | A | 7/1995 | Southern et al. |
| 5,470,502 | A | 11/1995 | Hahn et al. |
| 5,547,860 | A | 8/1996 | Kocher et al. |
| 5,561,071 | A | 10/1996 | Hollenberg et al. |
| 5,583,211 | A | 12/1996 | Coassin et al. |
| 5,658,734 | A | 8/1997 | Brock et al. |
| 5,837,858 | A | 11/1998 | Brennan |
| 5,874,219 | A | 2/1999 | Rava et al. |
| 5,919,523 | A | 7/1999 | Sundberg et al. |
| 6,136,269 | A | 10/2000 | Winkler et al. |
| 6,172,218 | B1 | 1/2001 | Brenner |
| 6,287,768 | B1 | 9/2001 | Chenchik et al. |
| 6,287,776 | B1 | 9/2001 | Hefti |
| 6,288,220 | B1 | 9/2001 | Kambara et al. |
| 6,291,193 | B1 | 9/2001 | Khodadoust |
| 6,297,006 | B1 | 10/2001 | Drmanac et al. |
| 6,346,413 | B1 | 2/2002 | Fodor et al. |
| 6,355,431 | B1 | 3/2002 | Chee et al. |
| 6,416,949 | B1 | 7/2002 | Dower et al. |
| 6,465,178 | B2 | 10/2002 | Chappa et al. |
| 6,482,591 | B2 | 11/2002 | Lockhart et al. |
| 6,514,751 | B2 | 2/2003 | Johann et al. |

(Continued)

FOREIGN PATENT DOCUMENTS

| | | |
|---|---|---|
| CN | 104449669 | 3/2015 |
| CN | 104610251 | 5/2015 |

(Continued)

OTHER PUBLICATIONS

Butkevich et al., 2018, PONy dyes: direct addition of P(111) nucleophiles ot organic fluorophores, Org. Lett. 26:1261-1264.
CAS Registry No. 2415499-72-6, entered STN: May 1, 2020, 1 p.
Kubo et al., 2012, Solid-state fluorescence properties and crystal structures of 7-(diethylamino)coumarin derivatives, Heterocycles, 84(1):315-321.
Hu et al., Apr. 19, 2015, Development of a highly sensitive fluorescent light-up probe for G-quadruplexes, Analyst, 140(13):4616-4625.
Kuziv et al., Jul. 17, 2020, Synthesis, spectral properties and evaluation of carboxy-functionalized 3-thiazolylcoumarins as blue-emitting fluorescent labeling reagents, Tetrahedron Letters, 61(35):152227.

(Continued)

*Primary Examiner* — Jezia Riley
(74) *Attorney, Agent, or Firm* — Knobbe, Martens, Olson & Bear, LLP

(57) ABSTRACT

The present application relates to substituted coumarin derivatives and their uses as fluorescent labels. These compounds may be used as fluorescent labels for nucleotides in nucleic acid sequencing applications.

25 Claims, 10 Drawing Sheets

(56) References Cited

U.S. PATENT DOCUMENTS

| | | |
|---|---|---|
| 6,524,793 B1 | 2/2003 | Chandler et al. |
| 6,610,482 B1 | 8/2003 | Fodor et al. |
| 6,924,372 B2 | 8/2005 | Czerney et al. |
| 8,431,416 B2 | 4/2013 | Diwu et al. |
| 10,160,861 B2 * | 12/2018 | Jansen ............... C07K 16/2812 |
| 11,390,619 B2 | 7/2022 | Romanov et al. |
| 2002/0102578 A1 | 8/2002 | Dickinson |
| 2002/0137062 A1 | 9/2002 | Williams et al. |
| 2003/0104437 A1 | 6/2003 | Barnes et al. |
| 2013/0079232 A1 | 3/2013 | Kain |
| 2014/0079923 A1 | 3/2014 | George |
| 2020/0277529 A1 | 9/2020 | Romanov et al. |
| 2020/0277670 A1 | 9/2020 | Romanov et al. |
| 2021/0188832 A1 | 6/2021 | Romanov et al. |
| 2022/0033900 A1 | 2/2022 | Romanov et al. |

FOREIGN PATENT DOCUMENTS

| | | |
|---|---|---|
| DE | 3609804 | 8/1987 |
| EP | 0 742 287 | 11/1996 |
| EP | 0 799 897 | 10/1997 |
| EP | 3 219 712 | 9/2017 |
| GB | 2017133 | 10/1979 |
| JP | 2016-138053 | 8/2016 |
| WO | WO 93/17126 | 9/1993 |
| WO | WO 95/11995 | 5/1995 |
| WO | WO 95/35505 | 12/1995 |
| WO | WO 98/44151 | 10/1998 |
| WO | WO 00/06770 | 2/2000 |
| WO | WO 00/18957 | 4/2000 |
| WO | WO 00/31148 | 6/2000 |
| WO | WO 00/53812 | 9/2000 |
| WO | WO 00/63437 | 10/2000 |
| WO | WO 01/01143 | 1/2001 |
| WO | WO 01/57248 | 8/2001 |
| WO | WO 02/12566 | 2/2002 |
| WO | WO 02/26891 | 4/2002 |
| WO | WO 03/014392 | 2/2003 |
| WO | WO 2003/105842 | 12/2003 |
| WO | WO 04/018493 | 3/2004 |
| WO | WO 04/018497 | 3/2004 |
| WO | WO 05/024010 | 3/2005 |
| WO | WO 05/047301 | 5/2005 |
| WO | WO 05/065814 | 7/2005 |
| WO | WO 06/120433 | 11/2006 |
| WO | WO 07/020457 | 2/2007 |
| WO | WO 11/127070 | 10/2011 |
| WO | WO 14/135221 | 9/2014 |
| WO | WO 14/139596 | 9/2014 |
| WO | WO 17/051201 | 3/2017 |
| WO | WO 18/060482 | 4/2018 |
| WO | WO 18/129214 | 7/2018 |
| WO | WO 2018/114710 | 8/2018 |
| WO | WO 19/077331 | 4/2019 |
| WO | WO 20/097607 | 5/2020 |

OTHER PUBLICATIONS

Margulies, Sep. 15, 2005, Genome sequencing in microfabricated high-density picolitre reactors, Nature, 437:376-380.

Nishizono et al., Jan. 2001, Synthesis of 3-aryl-7-7diethylaminocoumarin derivatives: reaction with isatin and their fluorescent properties, Heterocycles, 55(1):1897-1906.

Scheit, K. H. (1980). *Nucleotide analogs: Synthesis and biological function.* New York: John Wiley & Sons, TOC, 5 pages.

Schendure et al., Sep. 9, 2005, Accurate multiplex plogy sequencing of an evolved bacterial genome, Science, 309(5741):1728-1732.

Takechi et al., Nov. 2000, Screening search for organic fluorophores: syntheses and fluorescence properties of 3-azolyl-7-diethylaminocourain derivatives, Chemical and Pharmaceutical Bulletin, 48(11):1702-1710.

Uhlman et al., Jun. 1990, Antisense oligonucleotides: a new therapeutic principle, Chemical Reviews, 90(4):543-584.

Yamaguchi et al., Jun. 2017, Evaluation of synthesized coumarin derivatives on aromatase inhibitory activity, Bioorganic & Medicinal Chemistry Letters, 27(12):2645-2649.

International Search Report and Written Opinion dated Jan. 19, 2022 in international application No. PCT/EP2021/071024, filed Jul. 27, 2021.

Kuziv et al., 2008, Synthesis of reagents based on 7-substituted 3-thiazolylcoumarins for covalent labeling of oligonucleotides, Ukrainica Bioorganica Acta 1, 3-12.

\* cited by examiner

C/T 1X = 0.84

C/T 10X/1X = 0.85

C/T 1X = 0.53

C/T 10X/1X = 0.93

C/T 1X = 0.81

C/T 10X/1X = 0.85

C/T 1X = 0.69

C/T 10X/1X = 0.86

SUBSTITUTED COUMARIN DYES AND USES AS FLUORESCENT LABELS

INCORPORATION BY REFERENCE TO PRIORITY APPLICATION

The present application is a divisional application of U.S. application Ser. No. 17/385,232, filed Jul. 26, 2021, which claims the benefit of priority to U.S. Provisional Appl. No. 63/057,758, filed Jul. 28, 2020, each of which is incorporated by reference in its entirety.

FIELD

The present disclosure relates to substituted coumarin derivatives and their uses as fluorescent labels. In particular, the compounds may be used as fluorescent labels for nucleotides in nucleic acid sequencing applications.

BACKGROUND

Non-radioactive detection of nucleic acids bearing fluorescent labels is an important technology in molecular biology. Many procedures employed in recombinant DNA technology previously relied on the use of nucleotides or polynucleotides radioactively labeled with, for example $^{32}$P. Radioactive compounds permit sensitive detection of nucleic acids and other molecules of interest. However, there are serious limitations in the use of radioactive isotopes such as their expense, limited shelf life, insufficient sensitivity, and, more importantly, safety considerations. Eliminating the need for radioactive labels reduces both the safety risks and the environmental impact and costs associated with, for example, reagent disposal. Methods amenable to non-radioactive fluorescent detection include by way of non-limiting examples, automated DNA sequencing, hybridization methods, real-time detection of polymerase-chain-reaction products, and immunoassays.

For many applications, it is desirable to employ multiple spectrally-distinguishable fluorescent labels to achieve independent detection of a plurality of spatially-overlapping analytes. In such multiplex methods, the number of reaction vessels may be reduced, simplifying experimental protocols and facilitating the production of application-specific reagent kits. In multi-color automated DNA sequencing systems for example, multiplex fluorescent detection allows for the analysis of multiple nucleotide bases in a single electrophoresis lane, thereby increasing throughput over single-color methods, and reducing uncertainties associated with inter-lane electrophoretic mobility variations.

However, multiplex fluorescent detection can be problematic and there are a number of important factors that constrain selection of appropriate fluorescent labels. First, it may be difficult to find dye compounds with substantially-resolved absorption and emission spectra in a given application. In addition, when several fluorescent dyes are used together, generating fluorescence signals in distinguishable spectral regions by simultaneous excitation may be complicated because absorption bands of the dyes are usually widely separated, so it is difficult to achieve comparable fluorescence excitation efficiencies even for two dyes. Many excitation methods use high power light sources like lasers and therefore the dye must have sufficient photo-stability to withstand such excitation. A final consideration of particular importance to molecular biology methods is the extent to which the fluorescent dyes must be compatible with reagent chemistries such as, for example, DNA synthesis solvents and reagents, buffers, polymerase enzymes, and ligase enzymes.

As sequencing technology advances, a need has developed for further fluorescent dye compounds, their nucleic acid conjugates, and multiple dye sets that satisfy all the above constraints and that are amenable particularly to high throughput molecular methods such as solid phase sequencing and the like.

Fluorescent dye molecules with improved fluorescence properties such as suitable fluorescence intensity, shape, and wavelength maximum of fluorescence band can improve the speed and accuracy of nucleic acid sequencing. Strong fluorescence signals are especially important when measurements are made in water-based biological buffers and at higher temperatures as the fluorescence intensities of most organic dyes are significantly lower under such conditions. Moreover, the nature of the base to which a dye is attached also affects the fluorescence maximum, fluorescence intensity, and others spectral dye properties. The sequence-specific interactions between the nucleobases and the fluorescent dyes can be tailored by specific design of the fluorescent dyes. Optimization of the structure of the fluorescent dyes can improve the efficiency of nucleotide incorporation, reduce the level of sequencing errors, and decrease the usage of reagents in, and therefore the costs of, nucleic acid sequencing.

Some optical and technical developments have already led to greatly improved image quality but were ultimately limited by poor optical resolution. Generally, optical resolution of light microscopy is limited to objects spaced at approximately half of the wavelength of the light used. In practical terms, then, only objects that are laying quite far apart (at least 200 to 350 nm) could be resolved by light microscopy. One way to improve image resolution and increase the number of resolvable objects per unit of surface area is to use excitation light of a shorter wavelength. For example, if light wavelength is shortened by $\Delta\lambda\sim100$ nm with the same optics, resolution will be better (about $\Delta$ 50 nm/(about 15%)), less-distorted images will be recorded, and the density of objects on the recognizable area will be increased about 35%.

Certain nucleic acid sequencing methods employ laser light to excite and detect dye-labeled nucleotides. These instruments use longer wavelength light, such as red lasers, along with appropriate dyes that are excitable at 660 nm. To detect more densely packed nucleic acid sequencing clusters while maintaining useful resolution, a shorter wavelength blue light source (450-460 nm) may be used. In this case, optical resolution will be limited not by the emission wavelength of the longer wavelength red fluorescent dyes but rather by the emission of dyes excitable by the next longest wavelength light source, for example, by "green laser" at 532 nm. Thus, there is a need for blue dye labels for use in fluorescence detection in sequencing applications.

Although blue-dye chemistry and associated laser technologies have improved, for example, to yield dyes for DVD and Blu-ray disks, these compounds are not suitable for bio-labeling and cannot be used as biomarkers. Furthermore, certain blue dyes are not stable in an aqueous environment for a prolonged period of time. For example, in basic conditions these dyes may be easily attacked by nucleophiles, thus resulted in disturbance or deterioration of the dyes.

Unfortunately, appropriate commercially available blue dyes with strong fluorescence for nucleotide labeling are still quite rare. Described herein are fluorescent compounds with improved chemical stability suitable for nucleotide labeling with strong fluorescence under blue light excitation (e.g., blue LED or laser, for example, at about 450 nm to about 460 nm).

SUMMARY

The present invention relates to substituted coumarin derivatives. The compounds may be useful as fluorescent labels, particularly for nucleotide labeling in nucleic acid sequencing applications. In some aspect, the dyes absorb short-wavelength light, optimally at a wavelength of 450-460 nm and are particularly advantageous in situations where blue wavelength excitation sources having a wavelength of 450-460 nm are used. Blue wavelength excitation allows detection and resolution of a higher density of features per unit area due to the shorter wavelength of emission. When such dyes are used in conjugates with nucleotides, improvements can be seen in the length, intensity, accuracy, and quality of sequencing reads obtained during nucleic acid sequencing methods.

Some embodiments of the present disclosure relate to a compound of Formula (I), or a salt or mesomeric form thereof:

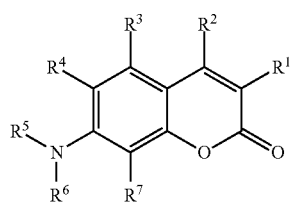
(I)

wherein $R^1$ is

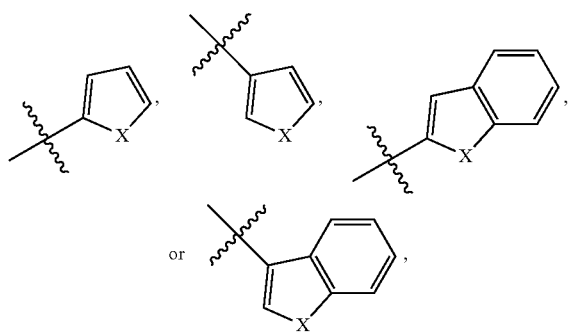

each optionally substituted with one or more substituents independently selected from the group consisting of carboxyl, —C(O)$NR^bR^c$, —C(O)$OR^d$, $C_1$-$C_6$ alkyl, substituted $C_1$-$C_6$ alkyl, halo, optionally substituted amino, hydroxy, sulfo, sulfonate, sulfate, N-sulfonamido, and S-sulfonamido;

$R^2$ is H, optionally substituted $C_1$-$C_6$ alkyl, or phenyl optionally substituted with one or more substituents selected from the group consisting of carboxyl, —C(O)$NR^bR^c$, —C(O)$OR^d$, optionally substituted $C_1$-$C_6$ alkyl, halo, cyano, nitro, sulfonyl, sulfino, sulfo, sulfonate, optionally substituted amino, and hydroxy;

each $R^3$, $R^4$ and $R^7$ is independently H, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, ($C_1$-$C_6$ alkoxy)($C_1$-$C_6$ alkyl), optionally substituted amino, halo, cyano, hydroxy, nitro, sulfonyl, sulfino, sulfo, sulfonate, S-sulfonamido, N-sulfonamido, optionally substituted $C_3$-$C_{10}$ carbocyclyl, or optionally substituted 3 to 10 membered heterocyclyl;

each $R^5$ and $R^6$ is independently H, $C_1$-$C_6$ alkyl, substituted $C_1$-$C_6$ alkyl, or $R^5$ and $R^6$ together with the nitrogen atom to which they are attached form an optionally substituted 4 to 10 membered heterocyclyl;

X is O, S, or $NR^a$;

$R^a$ is H or $C_1$-$C_6$ alkyl;

each $R^b$ and $R^c$ is independently H, $C_1$-$C_6$ alkyl, or substituted $C_1$-$C_6$ alkyl; and $R^d$ is optionally substituted $C_1$-$C_6$ alkyl or optionally substituted phenyl. In some embodiments, at least one of $R^5$ or $R^6$, or the optionally substituted 4 to 10 membered heterocyclyl formed from $R^5$ and $R^6$ and the nitrogen atom to which they are attached, comprises a carboxyl or —C(O)$OR^d$. In some other embodiments, $R^1$ comprises a carboxyl or —C(O)$OR^d$.

Some additional embodiments of the present disclosure relate to a compound of Formula (II) or (II'), or a salt or mesomeric form thereof:

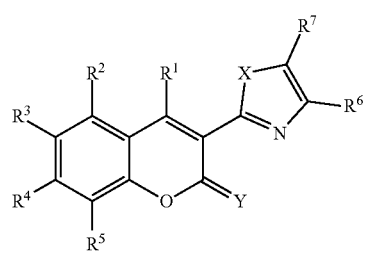
(II)

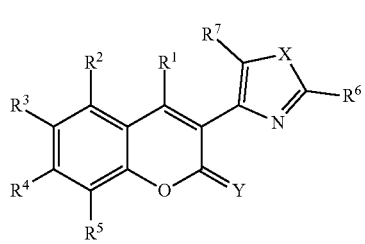
(II')

wherein X is S, O, or $NR^a$;

Y is O or NH;

each $R^1$, $R^2$, $R^3$ and $R^5$ is independently H, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, ($C_1$-$C_6$ alkoxy)($C_1$-$C_6$ alkyl), optionally substituted amino, halo, cyano, hydroxy, nitro, sulfonyl, sulfino, sulfo, sulfonate, S-sulfonamido, N-sulfonamido, optionally substituted $C_3$-$C_{10}$ carbocyclyl, optionally substituted $C_6$-$C_{10}$ aryl, optionally substituted 5 to 10 membered heteroaryl, or optionally substituted 3 to 10 membered heterocyclyl;

$R^4$ is —$NR^bR^c$, halo, —$OR^d$ or —$OS(O)_2R^d$;

each of $R^6$ and $R^7$ is independently H, carboxyl, —C(O)$NR^bR^c$, —C(O)$OR^d$, $C_1$-$C_6$ alkyl, substituted $C_1$-$C_6$ alkyl, $C_1$-$C_6$ haloalkyl, halo, optionally substituted amino, N-sulfonamido, sulfonyl, S-sulfonamido, hydroxy, cyano, nitro, optionally substituted phenyl, optionally substituted $C_3$-$C_8$ carbocyclyl, optionally substituted 5 to 10 membered heteroaryl, or optionally substituted 3 to 10 membered heterocyclyl; or $R^6$ and $R^7$ in Formula (II) together with the atoms to which they are attached form an optionally substituted $C_5$-$C_8$ carbocyclyl or an optionally substituted 5 to 8 membered heterocyclyl;

$R^a$ is H or $C_1$-$C_6$ alkyl;

each $R^b$ and $R^c$ is independently H, $C_1$-$C_6$ alkyl, or substituted $C_1$-$C_6$ alkyl; or $R^b$ and $R^c$ together with the nitrogen atom to which they are attached form an optionally substituted 4 to 10 membered heterocyclyl; and each $R^d$ is independently optionally substituted $C_1$-$C_6$ alkyl or optionally substituted phenyl. In some embodiments, $R^4$ is —$NR^bR^c$ and the compound is also represented by Formula (IIa) or (IIa'):

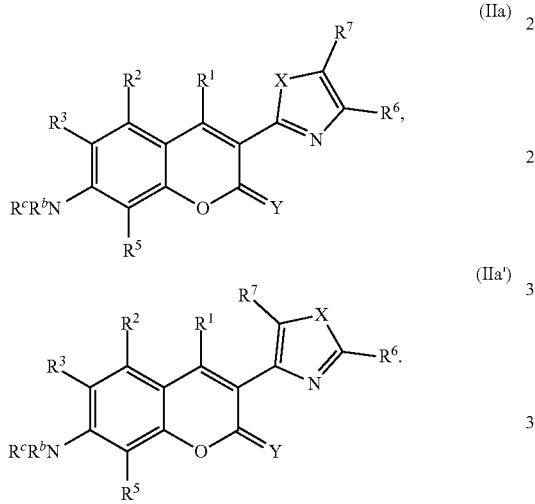

In some embodiments of the compounds of Formula (II), (II'), (IIa) or (IIa'), at least one of $R^6$ and $R^7$ comprises a carboxyl. In some embodiments of the compounds of Formula (II) or (IIa), when $R^6$ and $R^7$ and the atoms to which they are attached forms optionally substituted $C_5$-$C_8$ carbocyclyl or optionally substituted 5 to 8 membered heterocyclyl, the $C_5$-$C_8$ carbocyclyl or 5 to 8 membered heterocyclyl comprises or is substituted with a carboxyl. In some embodiments of Formula (IIa) or (IIa'), at least one of $R^b$ and $R^c$ comprises a carboxyl or —C(O)$OR^d$.

In some aspects, a compound of the present disclosure is labeled or conjugated with a substrate moiety such as, for example, a nucleoside, nucleotide, polynucleotide, polypeptide, carbohydrate, ligand, particle, cell, semi-solid surface (e.g., gel), or solid surface. The labelling or conjugation may be carried out via a carboxyl group (—$CO_2H$), which can be reacted using methods known in the art with an amino or hydroxyl group on a moiety (such as a nucleotide) or a linker bound thereto, to form an amide or ester.

Some other aspects of the present disclosure relate to dye compounds comprising linker groups to enable, for example, covalent attachment to a substrate moiety. Linking may be carried out at any position of the dye, including at any of the R groups. In some embodiments, linking may be carried out via $R^1$ or via $R^5$ or $R^6$ of Formula (I). In some other embodiments, linking may be carried out via $R^6$ or $R^7$ of Formula (II) or (II'), or via $R^b$ or $R^c$ of Formula (IIa) or (IIa').

Some further aspects of the present disclosure provide a labeled nucleoside or nucleotide compound defined by the formula:

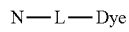

wherein N is a nucleoside or nucleotide;
L is an optional linker moiety; and
Dye is a moiety of a fluorescent compound of Formula (I), (II) or (II') according to the present disclosure.

Some additional aspects of the present disclosure relate to a moiety, in particular nucleotide or oligonucleotide, labeled with a compound of Formula (I), Formula (II), or Formula (II').

Some additional aspects of the present disclosure relate to a kit comprising a dye compound (free or in labeled form) that may be used in various immunological assays, oligonucleotide or nucleic acid labeling, or for DNA sequencing by synthesis. In yet another aspect, the disclosure provides kits comprising dye "sets" particularly suited to cycles of sequencing by synthesis on an automated instrument platform. In some aspect, the kit contains one or more nucleotides where at least one nucleotide is a labeled nucleotide described herein.

A further aspect of the disclosure is a method of determining the sequence of a single-stranded target polynucleotide, comprising:
(a) contacting a primer polynucleotide/target polynucleotide complex with one or more labeled nucleotides (e.g., A, G, C and T), wherein at least one of said labeled nucleotide is a nucleotide described herein, and wherein the primer polynucleotide is complementary to at least a portion of the target polynucleotide;
(b) incorporating a labeled nucleotide into the primer polynucleotide; and
(c) performing one or more fluorescent measurements to determine the identity of the incorporated nucleotide.

DETAILED DESCRIPTION

Figure 1:
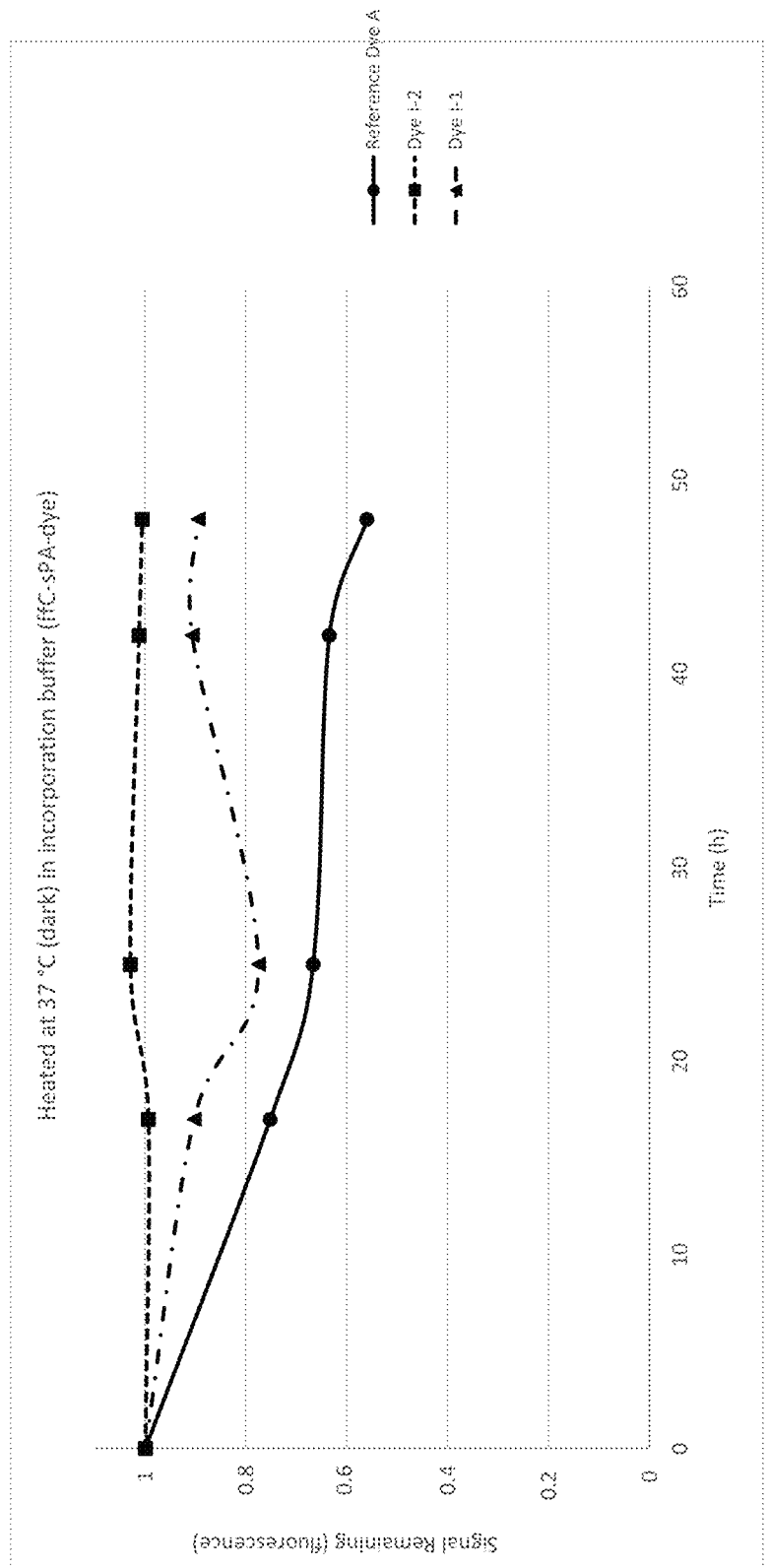
FIG. 1 is a line chart illustrating the fluorescent intensity of a fully functionalized C nucleotide (ffC) labeled with reference Dye A as compared to the same ffC labeled with Dye I-1 or Dye I-2 in a buffer solution at 37° C.

The present disclosure provides substituted coumarin compounds particularly suitable for methods of fluorescence detection and sequencing applications.

Definitions

The section headings used herein are for organizational purposes only and are not to be construed as limiting the subject matter described.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps but may include additional steps. When used in the context of a compound, composition, or device, the term "comprising" means that the compound, composition, or device includes at least the recited features or components, but may also include additional features or components.

As used herein, common organic abbreviations are defined as follows:

° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP Dideoxynucleotide triphosphate
ffN Fully functionalized nucleotide
h Hour(s)
RT Room temperature
SBS Sequencing by Synthesis
SM Starting material As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "$C_a$ to $C_b$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_2$-$C_6$ alkenyl includes $C_2$, $C_3$, $C_4$, $C_5$ and $C_6$ alkenyl, $C_2$-$C_5$ alkenyl, $C_3$-$C_4$ alkenyl, etc.; and $C_2$-$C_6$ alkynyl includes $C_2$, $C_3$, $C_4$, $C_5$ and $C_6$ alkynyl, $C_2$-$C_5$ alkynyl, $C_3$-$C_4$ alkynyl, etc. $C_3$-$C_8$ cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. By way of example only, "$C_1$-6 alkyl" or "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy" or "$C_1$-$C_9$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. By way of example only, "$C_2$-$C_6$ alkenyl" or "$C_{2-6}$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. By way of example only, "$C_{2-6}$ alkynyl" or "$C_2$-$C_6$ alkenyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 6 carbon atoms. The heteroalkyl group may be designated as "$C_{1-6}$ heteroalkyl", "$C_1$-$C_6$ heteroalkyl" or similar designations. The heteroalkyl group may contain one or more heteroatoms. By way of example only, "$C_{4-6}$heteroalkyl" or "$C_4$-$C_6$ heteroalkyl" indicates that there are four to six carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_6$-$C_{10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl", "$C_3$-$C_6$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle [2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(=O)OR" group in which R is selected from the group consisting of hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "sulfino" group refers to a "—S(=O)OH" group.

A "sulfo" group refers to a "—$S(=O)_2$OH" or "—$SO_3$H" group.

A "sulfonate" group refers to a "—$SO_3$" group.

A "sulfate" group refers to "—$SO_4$" group.

A "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—$N(R_A)SO_2R_B$" group in which $R_A$ and Re are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—$C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—$N(R_A)C(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_6$. 10 aryl, 5-10 membered heteroaryl, and 3-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_2$-$C_8$ alkoxyalkyl" and the like.

When a group is described as "optionally substituted" it may be either unsubstituted or substituted. Likewise, when a group is described as being "substituted", the substituent may be selected from one or more of the indicated substituents. As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —$SO_3H$, sulfonate, sulfate, sulfino, —$OSO_2C_1$-$C_4$alkyl, and oxo (=O). Wherever a group is described as "optionally substituted" that group can be substituted with the above substituents. In some embodiments, when an alkyl, alkenyl, alkynyl, aryl, heteroaryl, carbocyclyl or heterocyclyl group is substituted, each is independently substituted with one or more substituents selected from the group consisting of halo, —CN, —$SO_3^-$, —$OSO_3^-$, —$SO_3H$, —$SR^A$, —$OR^A$, —$NR^BR^C$, oxo, —$CONR^BR^C$, —$SO_2NR^BR^C$, —COOH, and —CO-$OR^B$, where $R^A$, $R^B$ and $R^C$ are each independently selected from H, alkyl, substituted alkyl, alkenyl, substituted alkenyl, alkynyl, substituted alkynyl, aryl, and substituted aryl.

As understood by one of ordinary skill in the art, a compound described herein may exist in ionized form, e.g., —$CO_2^-$, —$SO_3^-$ or —O—$SO_3^-$. If a compound contains a positively or negatively charged substituent group, for example, $SO_3^-$, it may also contain a negatively or positively charged counterion such that the compound as a whole is neutral. In other aspects, the compound may exist in a salt form, where the counterion is provided by a conjugate acid or base.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two "adjacent" R groups are said to form a ring "together with the atom to which they are attached," it is meant that the collective unit of the atoms, intervening bonds, and the two R groups are the recited ring. For example, when the following substructure is present:

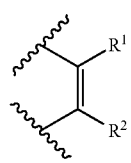

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

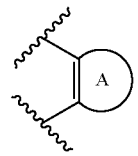

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

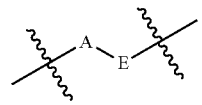

includes the substituent being oriented such that the A is attached at the leftmost attachment point of the molecule as well as the case in which A is attached at the rightmost attachment point of the molecule. In addition, if a group or substituent is depicted as

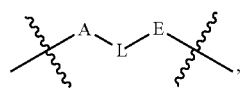

and L is defined an optionally present linker moiety; when L is not present (or absent), such group or substituent is equivalent to

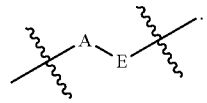

Compounds described herein can be represented as several mesomeric forms. Where a single structure is drawn, any of the relevant mesomeric forms are intended. The coumarin compounds described herein are represented by a single structure but can equally be shown as any of the related mesomeric forms. Exemplary mesomeric structures are shown below for Formula (I) and Formula (IIa) respectively:

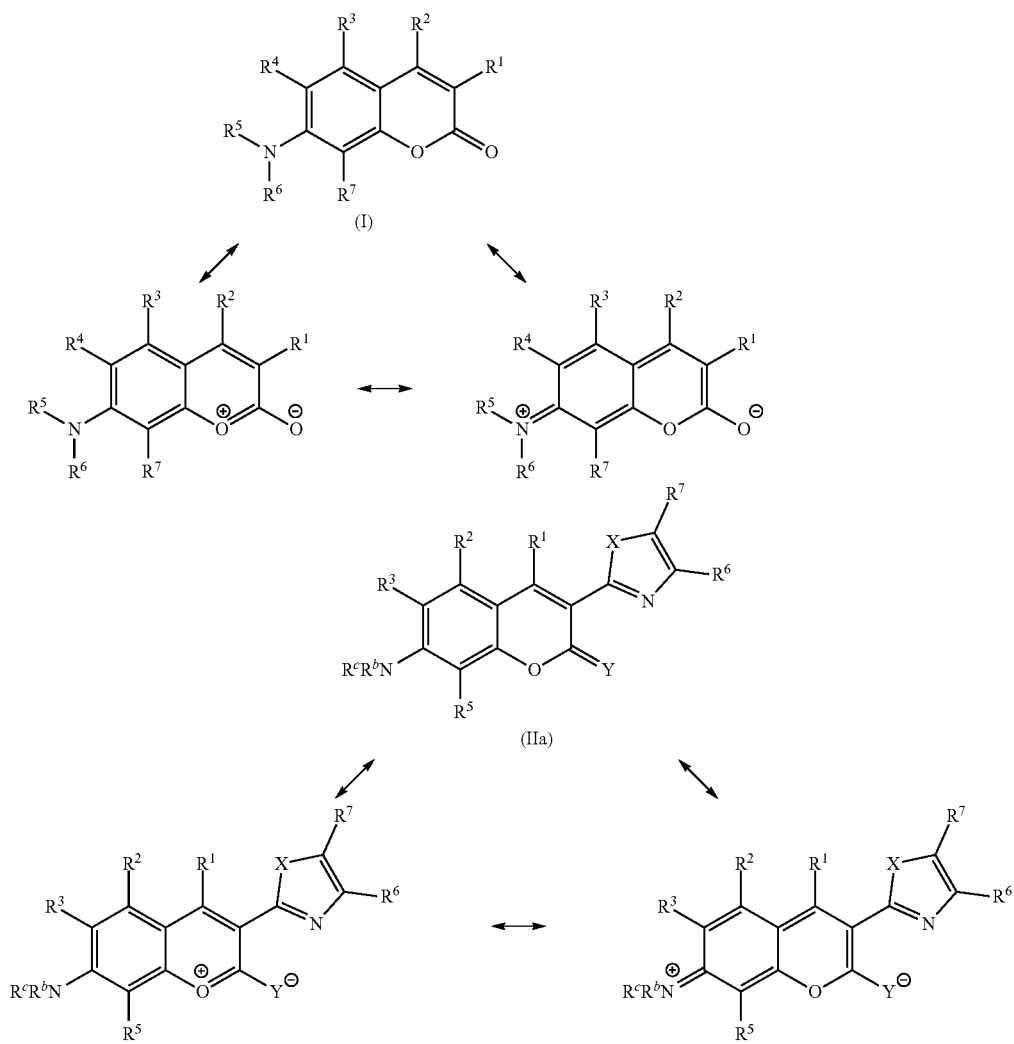

In each instance where a single mesomeric form of a compound described herein is shown, the alternative mesomeric forms are equally contemplated.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as 7-deaza adenine or 7-deaza guanine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, 7-deaza adenine, 7-deaza guanine. hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide or polynucleotide is described as "comprising" a nucleoside or nucleotide described herein, it means that the nucleoside or nucleotide described herein forms a covalent bond with the oligonucleotide or polynucleotide. Similarly, when a nucleoside or nucleotide is described as part of an oligonucleotide or polynucleotide, such as "incorporated into" an oligonucleotide or polynucleotide, it means that the nucleoside or nucleotide described herein forms a covalent bond with the oligonucleotide or polynucleotide. In some such embodiments, the covalent bond is formed between a 3' hydroxy group of the oligonucleotide or polynucleotide with the 5' phosphate group of a nucleotide described herein as a phosphodiester bond between the 3' carbon atom of the oligonucleotide or polynucleotide and the 5' carbon atom of the nucleotide.

As used herein, the term "cleavable linker" is not meant to imply that the whole linker is required to be removed. The cleavage site can be located at a position on the linker that ensures that part of the linker remains attached to the detectable label and/or nucleoside or nucleotide moiety after cleavage.

As used herein, "derivative" or "analog" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

and ).

As used herein, the terms "monophosphate," "diphosphate," and "triphosphate" are used in their ordinary sense as understood by those skilled in the art, and include protonated forms.

As used herein, the term "phasing" refers to a phenomenon in SBS that is caused by incomplete removal of the 3' terminators and fluorophores, and failure to complete the incorporation of a portion of DNA strands within clusters by polymerases at a given sequencing cycle. Pre-phasing is caused by the incorporation of nucleotides without effective 3' terminators, wherein the incorporation event goes 1 cycle ahead due to a termination failure. Phasing and pre-phasing cause the measured signal intensities for a specific cycle to consist of the signal from the current cycle as well as noise from the preceding and following cycles. As the number of cycles increases, the fraction of sequences per cluster affected by phasing and pre-phasing increases, hampering the identification of the correct base. Pre-phasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the discovery of nucleotide analogues which decrease the incidence of pre-phasing is surprising and provides a great advantage in SBS applications over existing nucleotide analogues. For example, the nucleotide analogues provided can result in faster SBS cycle time, lower phasing and pre-phasing values, and longer sequencing read lengths.

Fluorescent Compounds of Formula (I)

Some aspects of the disclosure relate to dyes of Formula (I), and salts and mesomeric forms thereof:

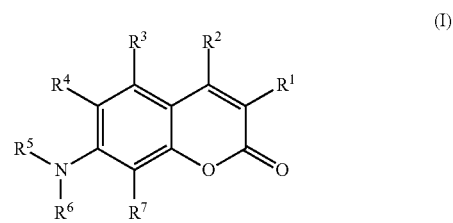

wherein $R^1$ is

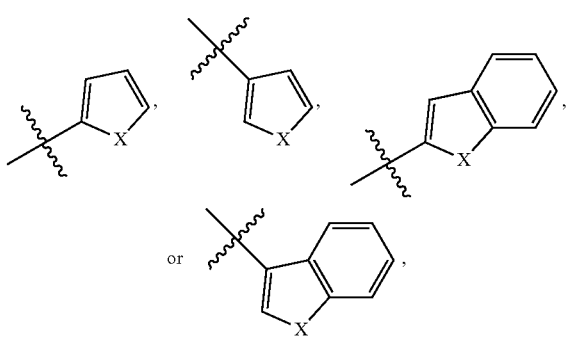

each optionally substituted with one or more substituents independently selected from the group consisting of carboxyl, —C(O)NR$^b$R$^c$, —C(O)OR$^d$, $C_1$-$C_6$ alkyl, substituted $C_1$-$C_6$ alkyl, halo, optionally substituted amino, hydroxy, sulfo, sulfonate, sulfate, N-sulfonamido, and S-sulfonamido;

$R^2$ is H, optionally substituted $C_1$-$C_6$ alkyl, or phenyl optionally substituted with one or more substituents selected from the group consisting of carboxyl, —C(O)NR$^b$R$^c$, —C(O)OR$^d$, optionally substituted $C_1$-$C_6$ alkyl, halo, cyano, nitro, sulfonyl, sulfino, sulfo, sulfonate, optionally substituted amino, and hydroxy;

each $R^3$, $R^4$ and $R^7$ is independently H, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, ($C_1$-$C_6$ alkoxy)($C_1$-$C_6$ alkyl), optionally substituted amino, halo, cyano, hydroxy, nitro, sulfonyl, sulfino, sulfo, sulfonate, S-sulfonamido, N-sulfonamido, optionally substituted $C_3$-$C_{10}$ carbocyclyl, or optionally substituted 3 to 10 membered heterocyclyl;

each $R^5$ and $R^6$ is independently H, $C_1$-$C_6$ alkyl, substituted $C_1$-$C_6$ alkyl, or $R^5$ and $R^6$ together with the nitrogen atom to which they are attached form an optionally substituted 4 to 10 membered heterocyclyl;

X is O, S, or NR$^a$;

$R^a$ is H or $C_1$-$C_6$ alkyl;

each $R^b$ and $R^c$ is independently H, $C_1$-$C_6$ alkyl, or substituted $C_1$-$C_6$ alkyl; and $R^d$ is optionally substituted $C_1$-$C_6$ alkyl or optionally substituted phenyl; provided that at least one of $R^5$ or $R^6$, or the optionally substituted 4 to 10 membered heterocyclyl formed from $R^5$ and $R^6$ and the nitrogen atom to which they are attached, comprises a carboxyl or —C(O)OR$^d$; or R$^1$ comprises a carboxyl or —C(O)OR$^d$.

In some embodiments of the compounds of Formula (I), In some embodiments, X is O. In some other embodiments, X is S. In other embodiments, X is NH. In some further embodiments, R$^1$ is

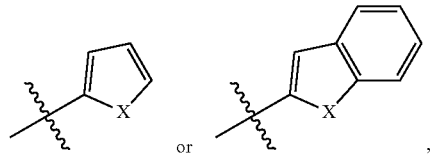

each substituted independently with carboxyl (—COOH), —C(O)NR$^b$R$^c$, or —C(O)OR$^d$. In some further embodiments, R$^1$ is,

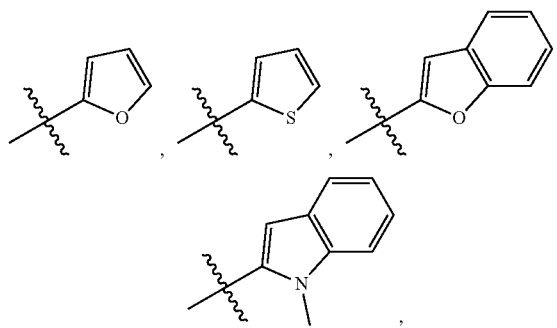

each substituted with carboxyl. In some such embodiments, R$^1$ is

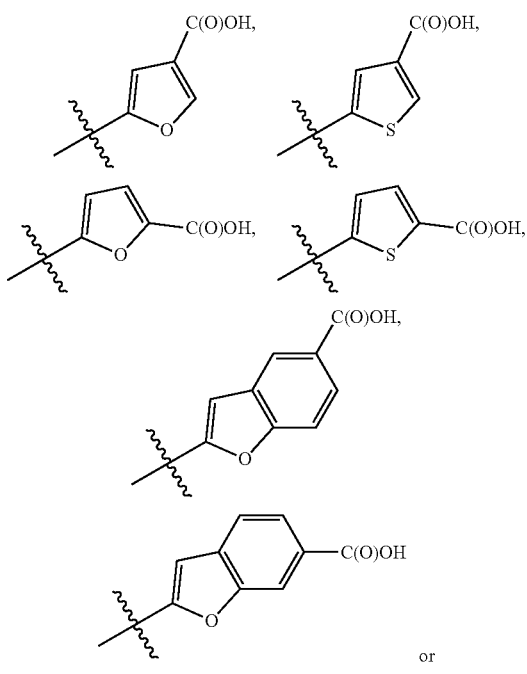

-continued

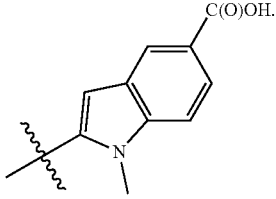

In some such embodiments, each of R$^5$ and R$^6$ is independently a C$_1$-C$_6$ alkyl. In one embodiment, each of R$^5$ and R$^6$ is ethyl. In other embodiments, at least one of R$^5$ and R$^6$ is H. In some such embodiments, R$^5$ is H and R$^6$ is a substituted C$_1$-C$_6$ alkyl. In other embodiments, each of R$^5$ and R$^6$ is a substituted C$_1$-C$_6$ alkyl. In some such embodiments, the C$_1$-C$_6$ alkyl is substituted with one or more substituents such as carboxyl, —C(O)OR$^d$, sulfo (—SO$_3$H), sulfonate (—SO$_3$$^-$), or sulfate (—O—SO$_3$$^-$), or an optionally substituted amino (such as a Boc protected amino group).

In some other embodiments of the compounds of Formula (I), R$^1$ is

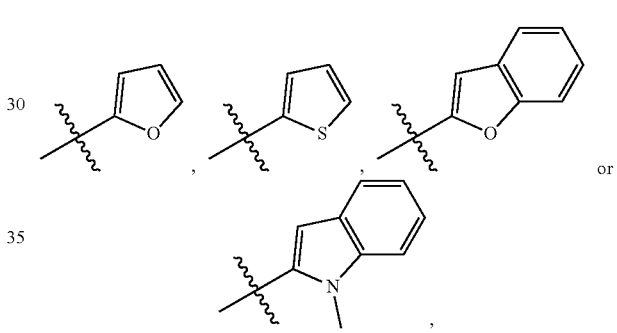

each unsubstituted or substituted with sulfo (—SO$_3$H). In some such embodiments, R$^5$ is H and R$^6$ is C$_1$-C$_6$ alkyl substituted with carboxyl. In other embodiments, each of R$^5$ and R$^6$ is C$_1$-C$_6$ alkyl substituted with carboxyl, —C(O)OR$^d$, sulfo (—SO$_3$H), sulfonate (—SO$_3$$^-$), or sulfate (—O—SO$_3$$^-$) and one of R$^5$ and R$^6$ is substituted with carboxyl. In other embodiments, R$^5$ and R$^6$ and the nitrogen atom to which they are attached form a 4, 5, 6 or 7 membered heterocyclyl comprises or is substituted with carboxyl. The heterocyclyl group may contain one or two heteroatoms. In one embodiment, the heterocyclyl group is piperidyl. In other embodiments, the heterocyclyl group is piperazinyl or morpholinyl. When the heterocyclyl group comprises a carboxyl group, it may be substituted with C$_1$-C$_6$ alkyl and the C$_1$-C$_6$ alkyl is substituted with the carboxyl group.

In some embodiments of the compounds of Formula (I), R$^2$ is H. In other embodiments, R$^2$ is C$_1$-C$_6$ alkyl, such as methyl, ethyl, isopropyl, or t-butyl. In one embodiment, R$^2$ is methyl.

In some embodiments of the compounds of Formula (I), at least one of R$^3$, R$^4$ and R$^7$ is H. In some further embodiments, each of R$^3$, R$^4$ and R$^7$ is H.

In any embodiments of compounds of Formula (I), when the compound is substituted with —C(O)OR$^d$, R$^d$ is C$_1$-C$_6$ alkyl or substituted C$_1$-C$_6$ alkyl. In one embodiment, R$^d$ is ethyl.

Specific embodiments of the compounds of Formula (I) are illustrated in Table 1 below:

TABLE 1

Exemplary Dyes of Formula (I)

| Compd. # | Structure |
|---|---|
| I-1 | |
| I-2 | |
| I-3 | |
| I-4 | |
| I-5 | |
| I-6 | 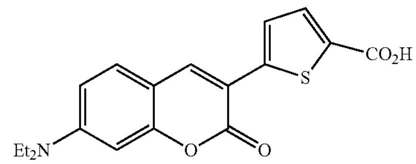 |
| I-7 | 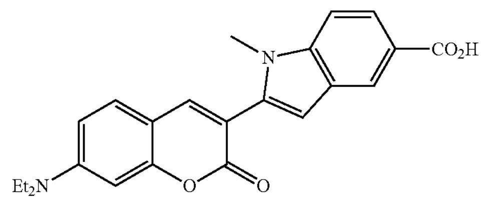 |
| I-8 | 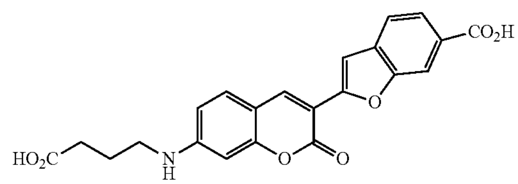 [SMILES: O=C(O)CCCNc1ccc2cc(-c3cc4ccc(C(=O)O)cc4o3)c(=O)oc2c1] |
| I-9 | 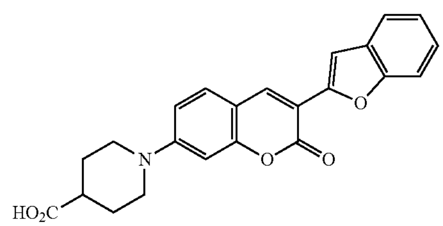 [SMILES: O=C(O)C1CCN(c2ccc3cc(-c4cc5ccccc5o4)c(=O)oc3c2)CC1] |
| I-10 | 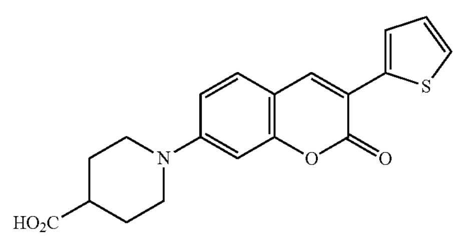 [SMILES: O=C(O)C1CCN(c2ccc3cc(-c4cccs4)c(=O)oc3c2)CC1] |
| I-11 | 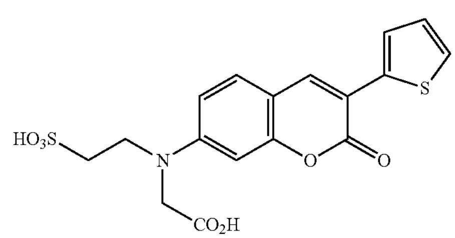 [SMILES: O=C(O)CN(CCS(=O)(=O)O)c1ccc2cc(-c3cccs3)c(=O)oc2c1] |
| I-12 | 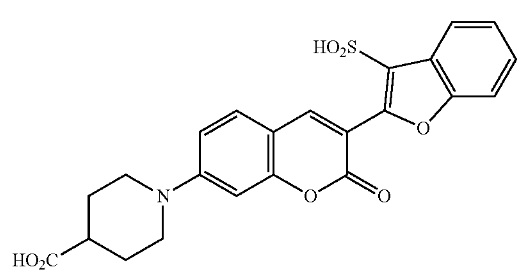 |

TABLE 1-continued

Exemplary Dyes of Formula (I)

Compd. # | Structure

I-13

I-14

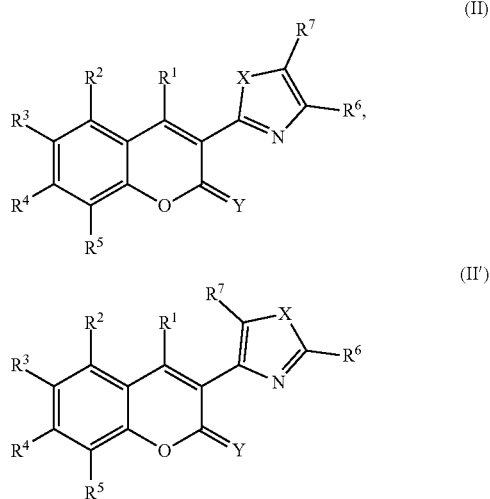

Fluorescent Compounds of Formula (II) or (II')

Some additional aspects of the disclosure relate to dyes of Formula (II) or (II'), and salts and mesomeric forms thereof:

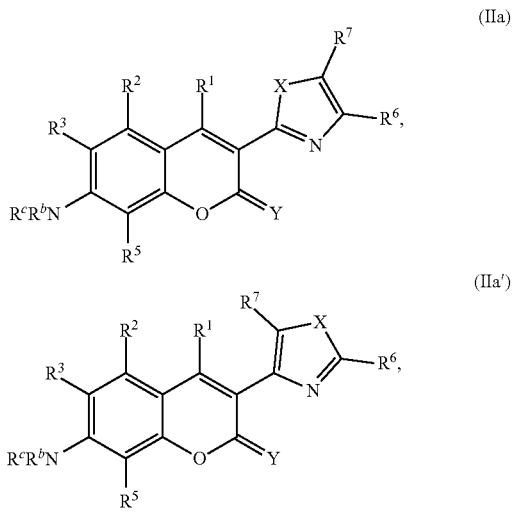

wherein X is S, O, or $NR^a$;
Y is O or NH;
each $R^1$, $R^2$, $R^3$ and $R^5$ is independently H, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, ($C_1$-$C_6$ alkoxy)($C_1$-$C_6$ alkyl), optionally substituted amino, halo, cyano, hydroxy, nitro, sulfonyl, sulfino, sulfo, sulfonate, S-sulfonamido, N-sulfonamido, optionally substituted $C_3$-$C_{10}$ carbocyclyl, optionally substituted $C_6$-$C_{10}$ aryl, optionally substituted 5 to 10 membered heteroaryl, or optionally substituted 3 to 10 membered heterocyclyl;
$R^4$ is —$NR^bR^c$, halo, —$OR^d$ or —$OS(O)_2R^d$;
each of $R^6$ and $R^7$ is independently H, carboxyl, —C(O)$NR^bR^c$, —C(O)$OR^d$, $C_1$-$C_6$ alkyl, substituted $C_1$-$C_6$ alkyl, $C_1$-$C_6$ haloalkyl, halo, optionally substituted amino, N-sulfonamido, sulfonyl, S-sulfonamido, hydroxy, cyano, nitro, optionally substituted phenyl, optionally substituted $C_3$-$C_8$ carbocyclyl, optionally substituted 5 to 10 membered heteroaryl, or optionally substituted 3 to 10 membered heterocyclyl; or $R^6$ and $R^7$ in Formula (II) together with the atoms to which they are attached form an optionally substituted $C_5$-$C_8$ carbocyclyl or an optionally substituted 5 to 8 membered heterocyclyl;
$R^a$ is H or $C_1$-$C_6$ alkyl;
each $R^b$ and $R^c$ is independently H, $C_1$-$C_6$ alkyl, or substituted $C_1$-$C_6$ alkyl; or $R^b$ and $R^c$ together with the nitrogen atom to which they are attached form an optionally substituted 4 to 10 membered heterocyclyl; and
each $R^d$ is independently optionally substituted $C_1$-$C_6$ alkyl or optionally substituted phenyl; provided that
at least one of $R^6$ and $R^7$, or the optionally substituted $C_5$-$C_8$ carbocyclyl or the optionally substituted 5 to 10 membered heteroaryl formed from $R^6$ and $R^7$ and the atoms to which they are attach comprises or is substituted with a carboxyl; or
$R^4$ is —$NR^bR^c$ and at least one of $R^b$ and $R^c$ is a substituted $C_1$-$C_6$ alkyl comprising or is substituted with a carboxyl or —C(O)$OR^d$.

In some embodiments of the compounds of Formula (II) or (II'), $R^4$ is halo (e.g., —F, —Cl or —Br). In some other embodiments, $R^4$ is —$OS(O)_2R^d$. In some such embodiments, $R^d$ is $C_1$-$C_6$ alkyl (e.g., methyl, ethyl, isopropyl or t-butyl) or $C_1$-$C_6$ haloalkyl (e.g., trifluoromethyl). In some other embodiments, $R^4$ is —$NR^bR^c$ and the compounds are also represented by Formula (IIa) or (IIa'):

or salts or mesomeric forms thereof. In some such embodiments, each of $R^b$ and $R^c$ is H, $C_1$-$C_6$ alkyl, or substituted $C_1$-$C_6$ alkyl. In one embodiment, each of $R^b$ and $R^c$ is H. In some embodiments, the substituted $C_1$-$C_6$ alkyl is independently substituted with carboxyl, —C(O)$OR^d$, sulfo (—$SO_3H$), sulfonate (—$SO_3$—), sulfate (—O—$SO_3$—) or —$SO_2NR^eR^f$, and wherein each of $R^e$ and $R^f$ is independently H or $C_1$-$C_6$ alkyl. For example, $R^b$ is H and $R^c$ is $C_1$-$C_6$ alkyl or substituted $C_1$-$C_6$ alkyl. In one such embodiment, $R^b$ is H and $R^c$ is ethyl. In another embodiment, $R^b$ is H and $R^c$ is $C_1$-$C_6$ alkyl (such as $C_3$ or $C_5$ alkyl) substituted with carboxyl, —C(O)OR$^d$, —SO$_3$H, —SO$_3^-$, —O—SO$_3^-$ or —SO$_2$NH$_2$. In other examples, each of R$^b$ and R$^c$ is independently C$_1$-C$_6$ alkyl, each may be substituted with —CO$_2$H, —C(O)OR$^d$, —SO$_3$H, —SO$_3^-$, —O—SO$_3^-$ or —SO$_2$NR$^e$R$^f$. In one embodiment, each of R$^b$ and R$^c$ is ethyl. In additional embodiments, R$^b$ is C$_3$ or C$_5$ alkyl substituted with —SO$_3$H, —SO$_3^-$ or —O—SO$_3^-$ and R$^c$ is C$_3$ or C$_5$ alkyl substituted with —CO$_2$H or —C(O)OR$^d$. In some other embodiments, R$^b$ and R$^c$ together with the nitrogen atom to which they are attached form an optionally substituted 4, 5, 6 or 7 membered heterocyclyl containing one or two heteroatoms in the ring structure (e.g.

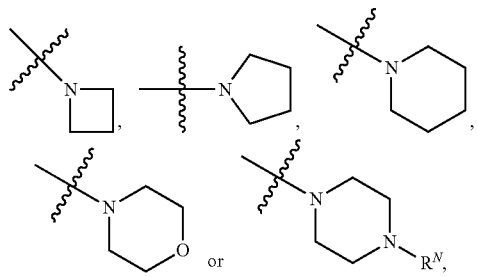

wherein R$^N$ is H, optionally substituted C$_1$-C$_6$ alkyl (such as methyl, C$_3$ or C$_5$ alkyl, each optionally substituted one or more substituents such as carboxyl, —C(O)OR$^d$, sulfo (—SO$_3$H), sulfonate (—SO$_3$—), sulfate (—O—SO$_3$—) or —SO$_2$NR$^e$R$^f$), or an amino protecting group, such as Boc (—C(=O)O$^t$Bu). In further embodiments, such 4, 5, 6 or 7 membered heterocyclyl may be substituted with one or more substituents, such as an unsubstituted or substituted C$_1$-C$_6$ alkyl, —CO$_2$H, —C(O)OR$^d$, —SO$_3$H, —SO$_3^-$, —O—SO$_3^-$ or —SO$_2$NR$^e$R$^f$.

In some embodiments of the compounds of Formula (II), (II'), (IIa) or (IIa'), Y is O. In other embodiments, Y is S. In still other embodiments, Y is NR$^a$, wherein R$^a$ is H, methyl, ethyl, isopropyl or t-butyl. In some such embodiments, X is O. In other embodiments, X is S.

In some embodiments of the compounds of Formula (II), (II'), (IIa) or (IIa'), each of R$^1$, R$^2$, R$^3$ and R$^5$ is independently H or optionally substituted C$_1$-C$_6$ alkyl (e.g., methyl, ethyl, isopropyl or t-butyl). In some such embodiments, R$^1$ is H or C$_1$-C$_6$ alkyl. In some such embodiments, R$^2$ is H. In some such embodiments, R$^3$ is H or C$_1$-C$_6$ alkyl. In some such embodiments, R$^5$ is H.

In some embodiments of the compounds of Formula (II), (II'), (IIa) or (IIa'), each of R$^6$ and R$^7$ is independently H, C$_1$-C$_6$ alkyl, substituted C$_1$-C$_6$ alkyl, optionally substituted phenyl, carboxyl or —C(O)OR$^d$. For example, one of R$^6$ or R$^7$ is H or C$_1$-C$_6$ alkyl, and the other one of R$^6$ or R$^7$ is carboxyl, —C(O)OR$^d$, C$_1$-C$_6$ alkyl, substituted C$_1$-C$_6$ alkyl, or phenyl optionally substituted with carboxyl, —C(O)OR$^d$, —SO$_3$H, —SO$_3^-$, or —O—SO$_3^-$. In some further embodiments, one of R$^6$ or R$^7$ is H or methyl, and the other one of R$^6$ or R$^7$ is carboxyl, —C(O)OR$^d$, methyl, phenyl, phenyl substituted with carboxyl or —C(O)OR$^d$, or C$_1$-C$_6$ alkyl (e.g., methyl or ethyl) substituted with carboxyl or —C(O)OR$^d$. In other embodiments of the compounds of Formula (II) or (IIa), R$^6$ and R$^7$ together with the atoms to which they are attached form an optionally substituted C$_5$, C$_6$, C$_7$ or C$_8$ carbocyclyl. For example, the C$_5$-C$_8$ carbocyclyl may be substituted with carboxyl, —C(O)OR$^d$, —SO$_3$H, —SO$_3^-$, —O—SO$_3^-$ or substituted C$_1$-C$_6$ alkyl (e.g., substituted with carboxyl or —C(O)OR$^d$).

In any embodiments of compounds of Formula (II), (II'), (IIa) or (IIa'), when the compound comprises or is substituted with C(O)OR$^d$, R$^d$ is C$_1$-C$_6$ alkyl or substituted C$_1$-C$_6$ alkyl. In one embodiment, R$^d$ is ethyl.

Specific embodiments of the compounds of Formula (IIa) are illustrated in Table 2A below.

TABLE 2A

Exemplary compounds of Formula (II) or (IIa) (where each of R$^1$, R$^2$ and R$^5$ is H).

| Compd. # | X | Y | R$^3$ | R$^b$ | R$^c$ | R$^6$ | R$^7$ |
|---|---|---|---|---|---|---|---|
| II-1 | S | O | H | H | (CH$_2$)$_3$SO$_3$H | CH$_2$CO$_2$H | H |
| II-1a | S | O | H | H | (CH$_2$)$_3$SO$_3$H | CH$_2$CO$_2$C$_2$H$_5$ | H |
| II-1b | S | NH | H | H | (CH$_2$)$_3$SO$_3$H | CH$_2$CO$_2$C$_2$H$_5$ | H |
| II-1c | S | O | H | H | (CH$_2$)$_2$SO$_3$H | CH$_2$CO$_2$H | H |
| II-1d | S | O | H | H | (CH$_2$)$_4$SO$_3$H | CH$_2$CO$_2$H | H |
| II-1e | S | O | H | (CH$_2$)$_3$SO$_3$H | (CH$_2$)$_3$SO$_3$H | CH$_2$CO$_2$H | H |
| II-1f | S | O | H | (CH$_2$)$_2$SO$_3$H | (CH$_2$)$_2$SO$_3$H | CH$_2$CO$_2$H | H |
| II-1g | S | O | H | (CH$_2$)$_4$SO$_3$H | (CH$_2$)$_4$SO$_3$H | CH$_2$CO$_2$H | H |
| II-2 | S | O | H | C$_2$H$_5$ | C$_2$H$_5$ | CH$_2$CO$_2$H | H |
| II-2a | S | O | H | C$_2$H$_5$ | C$_2$H$_5$ | CH$_2$CO$_2$C$_2$H$_5$ | H |
| II-2b | S | NH | H | C$_2$H$_5$ | C$_2$H$_5$ | CH$_2$CO$_2$C$_2$H$_5$ | H |
| II-3 | S | O | H | H | (CH$_2$)$_3$SO$_3$H | CO$_2$H | H |
| II-3a | S | O | H | H | (CH$_2$)$_3$SO$_3$H | CO$_2$C$_2$H$_5$ | H |
| II-3b | S | NH | H | H | (CH$_2$)$_3$SO$_3$H | CO$_2$C$_2$H$_5$ | H |
| II-4 | S | O | H | C$_2$H$_5$ | C$_2$H$_5$ | CO$_2$H | H |
| II-4a | S | O | H | C$_2$H$_5$ | C$_2$H$_5$ | CO$_2$C$_2$H$_5$ | H |
| II-4b | S | NH | H | C$_2$H$_5$ | C$_2$H$_5$ | CO$_2$C$_2$H$_5$ | H |
| II-5 | S | O | H | C$_2$H$_5$ | C$_2$H$_5$ | p-C$_6$H$_4$CO$_2$H | H |
| II-5a | S | O | H | C$_2$H$_5$ | C$_2$H$_5$ | p-C$_6$H$_4$CO$_2$C$_2$H$_5$ | H |
| II-5b | S | NH | H | C$_2$H$_5$ | C$_2$H$_5$ | p-C$_6$H$_4$CO$_2$C$_2$H$_5$ | H |
| II-6 | S | O | H | C$_2$H$_5$ | C$_2$H$_5$ | H | CO$_2$H |
| II-6a | S | O | H | C$_2$H$_5$ | C$_2$H$_5$ | H | CO$_2$C$_2$H$_5$ |
| II-6b | S | NH | H | C$_2$H$_5$ | C$_2$H$_5$ | H | CO$_2$C$_2$H$_5$ |
| II-7 | S | O | H | H | (CH$_2$)$_3$SO$_3$H | H | CO$_2$H |
| II-7a | S | O | H | H | (CH$_2$)$_3$SO$_3$H | H | CO$_2$C$_2$H$_5$ |
| II-7b | S | NH | H | H | (CH$_2$)$_3$SO$_3$H | H | CO$_2$C$_2$H$_5$ |
| II-8 | S | O | H | H | (CH$_2$)$_3$SO$_3$H | CH$_3$ | CO$_2$H |
| II-8a | S | O | H | H | (CH$_2$)$_3$SO$_3$H | CH$_3$ | CO$_2$C$_2$H$_5$ |

TABLE 2A-continued

Exemplary compounds of Formula (II) or (IIa) (where each of $R^1$, $R^2$ and $R^5$ is H).

| Compd. # | X | Y | $R^3$ | $R^b$ | $R^c$ | $R^6$ | $R^7$ |
|---|---|---|---|---|---|---|---|
| II-8b | S | NH | H | H | $(CH_2)_3SO_3H$ | $CH_3$ | $CO_2C_2H_5$ |
| II-9 | S | O | H | H | $(CH_2)_3SO_3H$ | $CH_3$ | $CH_2CO_2H$ |
| II-9a | S | O | H | H | $(CH_2)_3SO_3H$ | $CH_3$ | $CH2CO_2C_2H_5$ |
| II-9b | S | NH | H | H | $(CH_2)_3SO_3H$ | $CH_3$ | $CH2CO_2C_2H_5$ |
| II-10 | S | O | H | H | $C_2H_5$ | $CH_3$ | $CO_2H$ |
| II-11 | S | O | H | H | $C_2H_5$ | $CO_2H$ | H |
| II-11a | S | O | H | H | $C_2H_5$ | $CH_2CO_2C_2H_5$ | H |
| II-11b | S | O | H | H | $C_4H_9$ | $CH_2CO_2C_2H_5$ | H |
| II-12 | S | O | H | $C_2H_5$ | $C_2H_5$ | $CH_3$ | $CO_2H$ |
| II-12a | S | O | H | $C_2H_5$ | $C_2H_5$ | $CH_3$ | $CO_2C_2H_5$ |
| II-12b | S | NH | H | $C_2H_5$ | $C_2H_5$ | $CH_3$ | $CO_2C_2H_5$ |
| II-13 | S | O | $CH_3$ | H | $C_2H_5$ | $CH_3$ | $CO_2H$ |
| II-13a | S | O | $CH_3$ | H | $C_2H_5$ | $CH_3$ | $CO_2C_2H_5$ |
| II-14 | S | O | $CH_3$ | H | $C_2H_5$ | $CO_2H$ | H |
| II-14a | S | O | $CH_3$ | H | $C_2H_5$ | $CO_2C_2H_5$ | H |
| II-15 | S | O | H | H | $(CH_2)_5SO_3H$ | $CH_3$ | $CO_2H$ |
| II-16 | S | O | H | H | $(CH_2)_5SO_3H$ | $CO_2H$ | H |
| II-17 | S | O | H | H | $(CH_2)_5SO_3H$ | $CH_3$ | $CH_2CO_2H$ |
| II-18 | S | O | H | H | $(CH_2)_5SO_3H$ | $CH_2CO_2H$ | H |
| II-19 | S | O | H | H | $(CH_2)_5SO_2NH_2$ | $CH_3$ | $CO_2H$ |
| II-20 | S | O | H | H | $(CH_2)_5SO_2NH_2$ | $CO_2H$ | H |
| II-21 | S | O | H | H | $(CH_2)_5SO_2NH_2$ | $CH_3$ | $CH_2CO_2H$ |
| II-22 | S | O | H | H | $(CH_2)_5SO_2NH_2$ | $CH_2CO_2H$ | H |
| II-23 | S | O | H | H | $(CH_2)_3SO_2NH_2$ | $CH_3$ | $CH_2CO_2H$ |
| II-24 | S | O | H | H | $(CH_2)_3SO_2NH_2$ | $CH_2CO_2H$ | H |
| II-25 | S | O | H | H | $(CH_2)_3SO_2NH_2$ | $CH_3$ | $CO_2H$ |
| II-26 | S | O | H | H | $(CH_2)_3SO_2NH_2$ | $CO_2H$ | H |
| II-27 | S | O | H | H | H | $CH_3$ | $CO_2H$ |
| II-27a | S | O | H | H | H | $CH_3$ | $CO_2C_2H_5$ |
| II-28 | S | O | H | H | H | $CO_2H$ | H |
| II-29 | S | O | H | H | H | $CH_3$ | $CH_2CO_2H$ |
| II-29a | S | O | H | H | H | $CH_3$ | $CH_2CO_2C_2H_5$ |
| II-30 | S | O | H | H | H | $CH_2CO_2H$ | H |
| II-31 | S | O | H | | 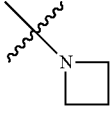<br>(joined with N) | $CO_2H$ | H |
| II-31a | S | O | H | | 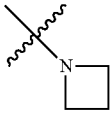<br>(joined with N) | $CO_2C_2H_5$ | H |
| II-32 | S | O | H | | 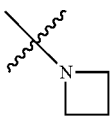<br>(joined with N) | $CH_3$ | $CO_2H$ |
| II-32a | S | O | H | | 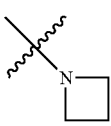<br>(joined with N) | $CH_3$ | $CO_2C_2H_5$ |
| II-33 | S | O | H | | 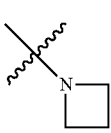<br>(joined with N) | $CH_2CO_2H$ | H |

TABLE 2A-continued

Exemplary compounds of Formula (II) or (IIa) (where each of $R^1$, $R^2$ and $R^5$ is H).

| Compd. # | X | Y | $R^3$ | $R^b$ | $R^c$ | $R^6$ | $R^7$ |
|---|---|---|---|---|---|---|---|
| II-33a | S | O | H | | 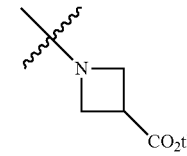 (joined with N) | $CH_2CO_2H$ | H |
| II-34 | S | O | H | $(CH_2)_3CO_2H$ | $(CH_2)_3SO_3H$ | $CH_3$ | $CH_3$ |
| II-34a | S | O | H | $(CH_2)_3CO_2{}^tBu$ | $(CH_2)_5SO_3H$ | $CH_3$ | $CH_3$ |
| II-35 | O | O | H | $(CH_2)_3CO_2H$ | $(CH_2)_3SO_3H$ | $CH_3$ | $CH_3$ |
| II-35a | O | O | H | $(CH_2)_3CO_2{}^tBu$ | $(CH_2)_5SO_3H$ | $CH_3$ | $CH_3$ |
| II-36 | S | O | H | $(CH_2)_3CO_2H$ | $(CH_2)_3SO_3H$ | $CH_3$ | H |
| II-36a | S | O | H | $(CH_2)_3CO_2{}^tBu$ | $(CH_2)_5SO_3H$ | $CH_3$ | H |
| II-37 | O | O | H | $(CH_2)_3CO_2H$ | $(CH_2)_3SO_3H$ | $CH_3$ | H |
| II-37a | O | O | H | $(CH_2)_3CO_2{}^tBu$ | $(CH_2)_5SO_3H$ | $CH_3$ | H |
| II-38 | S | O | H | $(CH_2)_3CO_2H$ | $(CH_2)_3SO_3H$ | H | $CH_3$ |
| II-38a | S | O | H | $(CH_2)_3CO_2{}^tBu$ | $(CH_2)_5SO_3H$ | H | $CH_3$ |
| II-39 | S | O | H | $(CH_2)_3CO_2H$ | $(CH_2)_3SO_3H$ | $C_6H_5$ | H |
| II-39a | S | O | H | $(CH_2)_3CO_2{}^tBu$ | $(CH_2)_5SO_3H$ | $C_6H_5$ | H |
| II-40 | O | O | H | $(CH_2)_3CO_2H$ | $(CH_2)_3SO_3H$ | $C_6H_5$ | H |
| II-40a | O | O | H | $(CH_2)_3CO_2{}^tBu$ | $(CH_2)_5SO_3H$ | $C_6H_5$ | H |
| II-41 | S | O | H | $(CH_2)_3CO_2H$ | $(CH_2)_3SO_3H$ | H | $C_6H_5$ |
| II-41a | S | O | H | $(CH_2)_3CO_2{}^tBu$ | $(CH_2)_5SO_3H$ | H | $C_6H_5$ |
| II-42 | O | O | H | $(CH_2)_3CO_2H$ | $(CH_2)_3SO_3H$ | H | $C_6H_5$ |
| II-42a | O | O | H | $(CH_2)_3CO_2{}^tBu$ | $(CH_2)_5SO_3H$ | H | $C_6H_5$ |
| II-43 | S | O | H | $(CH_2)_3CO_2H$ | $(CH_2)_3SO_3H$ | 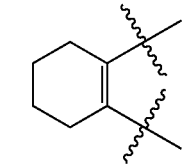 [SMILES: *C1=C(*)CCCC1] (double bond is part of the thiazole ring) | |
| II-43a | S | O | H | $(CH_2)_3CO_2{}^tBu$ | $(CH_2)_5SO_3H$ | 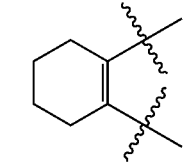 [SMILES: *C1=C(*)CCCC1] | |
| II-43b | S | O | $CH_3$ | H | $C_2H_5$ | 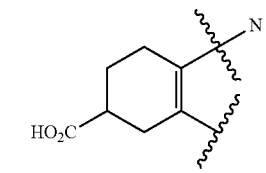 (—$CO_2H$ is para N atom of the thiazole ring) | |
| II-43c | S | O | $CH_3$ | H | $C_2H_5$ | 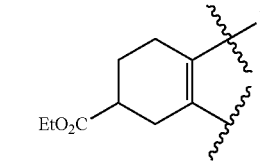 (—$CO_2H$ is para to N atom of the thiazole ring) | |

TABLE 2A-continued

Exemplary compounds of Formula (II) or (IIa) (where each of $R^1$, $R^2$ and $R^5$ is H).

| Compd. # | X | Y | $R^3$ | $R^b$ | $R^c$ | $R^6$ | $R^7$ |
|---|---|---|---|---|---|---|---|
| II-43d | O | O | H | $C_2H_5$ | $C_2H_5$ | | cyclohexene fused with $CO_2H$ ortho to N (—$CO_2H$ is ortho to N atom of th thiazole ring) |
| II-43e | O | O | H | $C_2H_5$ | $C_2H_5$ | | cyclohexene fused with $CO_2Et$ ortho to N (—$CO_2Et$ is ortho to N atom of the thiazole ring) |
| II-44 | O | O | H | $(CH_2)_3CO_2H$ | $(CH_2)_3SO_3H$ | | cyclohexene (double bond is part of the thiazole ring) |
| II-44a | O | O | H | $(CH_2)_3CO_2{}^tBu$ | $(CH_2)_5SO_3H$ | | cyclohexene |
| II-45 | S | O | H | $(CH_2)_3CO_2H$ | $(CH_2)_3SO_3H$ | | cyclopentene (double bond is part of the thiazole ring) |
| II-45a | S | O | H | $(CH_2)_3CO_2{}^tBu$ | $(CH_2)_5SO_3H$ | | cyclopentene |
| II-46 | O | O | H | $(CH_2)_3CO_2H$ | $(CH_2)_3SO_3H$ | | cyclopentene (double bond is part of the thiazole ring) |

TABLE 2A-continued

Exemplary compounds of Formula (II) or (IIa) (where each of $R^1$, $R^2$ and $R^5$ is H).

| Compd. # | X | Y | $R^3$ | $R^b$ | $R^c$ | $R^6$ | $R^7$ |
|---|---|---|---|---|---|---|---|
| II-46a | O | O | H | $(CH_2)_3CO_2{}^tBu$ | $(CH_2)_5SO_3H$ | | |
| II-47 | S | O | H | (piperazinyl-N-CH$_3$, joint with N) | | $CH_2CO_2H$ | H |
| II-47a | S | O | H | (piperazinyl-N-CH$_3$, joint with N) | | $CH_2CO_2C_2H_5$ | H |
| II-48 | S | O | H | (N-methylpiperazinium with propyl-SO$_3^{\ominus}$, joint with N) | | $CH_2CO_2H$ | H |
| II-48a | S | O | H | (N-methylpiperazinium with propyl-SO$_3^{\ominus}$, joint with N) | | $CH_2CO_2C_2H_5$ | H |
| II-48b | S | O | H | (N-methylpiperazinium with propyl-OSO$_3^{\ominus}$, joint with N) | | $CH_2CO_2H$ | H |
| II-48c | S | O | H | (N-methylpiperazinium with propyl-OSO$_3^{\ominus}$, joint with N) | | $CH_2CO_2C_2H_5$ | H |
| II-49 | S | O | H | (N-methylpiperazinium with (CH$_2$)$_3$-COO$^{\ominus}$, joint with N) | | $CH_2CO_2H$ | H |

TABLE 2A-continued

Exemplary compounds of Formula (II) or (IIa) (where each of $R^1$, $R^2$ and $R^5$ is H).

| Compd. # | X | Y | $R^3$ | $R^b$ | $R^c$ | $R^6$ | $R^7$ |
|---|---|---|---|---|---|---|---|
| II-49a | S | O | H | 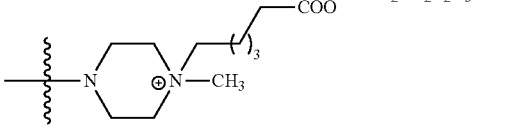 (joint with N) | | $CH_2CO_2C_2H_5$ | H |
| II-50 | S | O | H |  (joint with N) | | $CH_2CO_2H$ | H |
| II-50a | S | O | H | 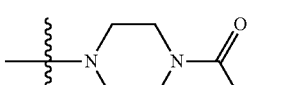 (joint with N) | | $CH_2CO_2C_2H_5$ | H |

TABLE 2B

Additional exemplary compounds of Formula (II) (where each of $R^1$, $R^2$, and $R^5$ is H).

| Compd. # | X | Y | $R^3$ | $R^4$ | $R^6$ | $R^7$ |
|---|---|---|---|---|---|---|
| II-51 | S | O | H | F | $CH_2CO_2H$ | H |
| II-51a | S | O | H | F | $CH_2CO_2C_2H_5$ | H |
| II-51b | S | NH | H | F | $CH_2CO_2C_2H_5$ | H |
| II-51c | S | O | H | Br | $CH_2CO_2H$ | H |
| II-51d | S | O | H | Br | $CH_2CO_2C_2H_5$ | H |
| II-51e | S | NH | H | Br | $CH_2CO_2C_2H_5$ | H |
| II-52 | S | O | H | F | $CO_2H$ | H |
| II-52a | S | O | H | F | $CO_2C_2H_5$ | H |
| II-52b | S | NH | H | F | $CO_2C_2H_5$ | H |
| II-52c | S | O | H | Br | $CO_2H$ | H |
| II-52d | S | O | H | Br | $CO_2C_2H_5$ | H |
| II-53 | S | O | H | F | H | $CO_2H$ |
| II-53a | S | O | H | F | H | $CO_2C_2H_5$ |
| II-53b | S | NH | H | F | H | $CO_2C_2H_5$ |
| II-54 | S | O | H | F | $CH_3$ | $CO_2H$ |
| II-54a | S | O | H | F | $CH_3$ | $CO_2C_2H_5$ |
| II-54b | S | NH | H | F | $CH_3$ | $CO_2C_2H_5$ |
| II-54c | S | O | H | Br | $CH_3$ | $CO_2H$ |
| II-54d | S | O | H | Br | $CH_3$ | $CO_2C_2H_5$ |
| II-54e | S | NH | H | Br | $CH_3$ | $CO_2C_2H_5$ |
| II-55 | S | O | H | F | $CH_3$ | $CH_2CO_2H$ |
| II-55a | S | O | H | F | $CH_3$ | $CH_2CO_2C_2H_5$ |
| II-55b | S | NH | H | F | $CH_3$ | $CH_2CO_2C_2H_5$ |
| II-56 | S | O | H | $OSO_2CF_3$ | $CH_3$ | $CO_2H$ |
| II-56a | S | O | H | $OSO_2CF_3$ | $CH_3$ | $CO_2C_2H_5$ |
| II-57 | S | O | H | $OSO_2CF_3$ | $CO_2H$ | H |
| II-57a | S | O | H | $OSO_2CF_3$ | $CO_2C_2H_5$ | H |
| II-58 | S | O | H | $OSO_2CF_3$ | $CH_3$ | $CH_2CO_2H$ |
| II-58a | S | O | H | $OSO_2CF_3$ | $CH_3$ | $CH_2CO_2C_2H_5$ |
| II-59 | S | O | H | $OSO_2CF_3$ | $CH_2CO_2H$ | H |
| II-59a | S | O | H | $OSO_2CF_3$ | $CH_2CO_2C_2H_5$ | H |
| II-60 | S | O | F | H | $CH_2CO_2H$ | H |
| II-60a | S | O | F | H | $CH_2CO_2C_2H_5$ | H |

Specific embodiments of the compounds of Formula (IIa') are illustrated in Table 2C below.

TABLE 2C

Exemplary compounds of Formula (II') or (IIa') (where each of $R^1$, $R^2$, $R^3$ and $R^5$ is H).

| Compd. # | X | Y | $R^b$ | $R^c$ | $R^6$ | $R^7$ |
|---|---|---|---|---|---|---|
| II-1' | S | O | $C_2H_5$ | $C_2H_5$ | $CH_2CO_2H$ | H |
| II-1a' | S | O | $C_2H_5$ | $C_2H_5$ | $CH_2CO_2C_2H_5$ | H |
| II-1b' | S | NH | $C_2H_5$ | $C_2H_5$ | $CH_2CO_2C_2H_5$ | H |
| II-2' | S | O | H | $(CH_2)_3SO_3H$ | $CH_2CO_2H$ | H |
| II-2a' | S | O | H | $(CH_2)_3SO_3H$ | $CH_2CO_2C_2H_5$ | H |
| II-2b' | S | NH | H | $(CH_2)_3SO_3H$ | $CH_2CO_2C_2H_5$ | H |

Non-limiting exemplary compounds of Formula (IIa) include the following:

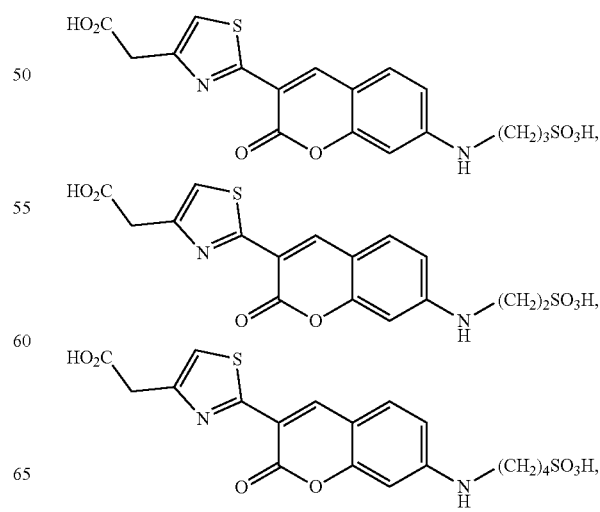

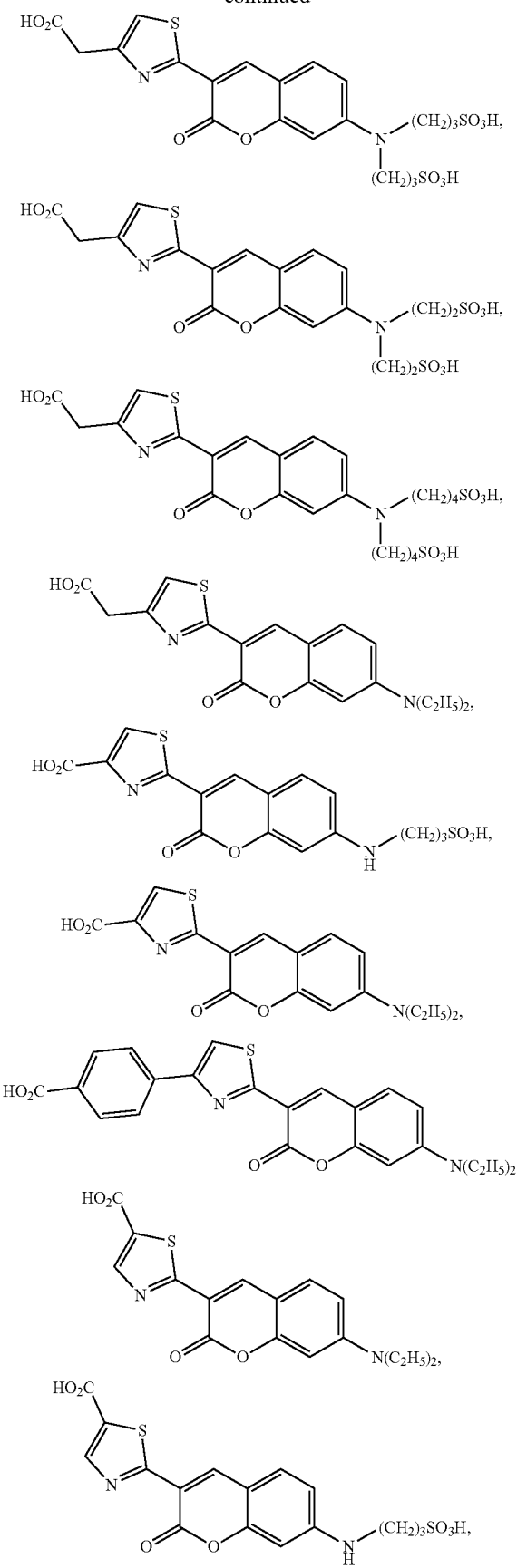
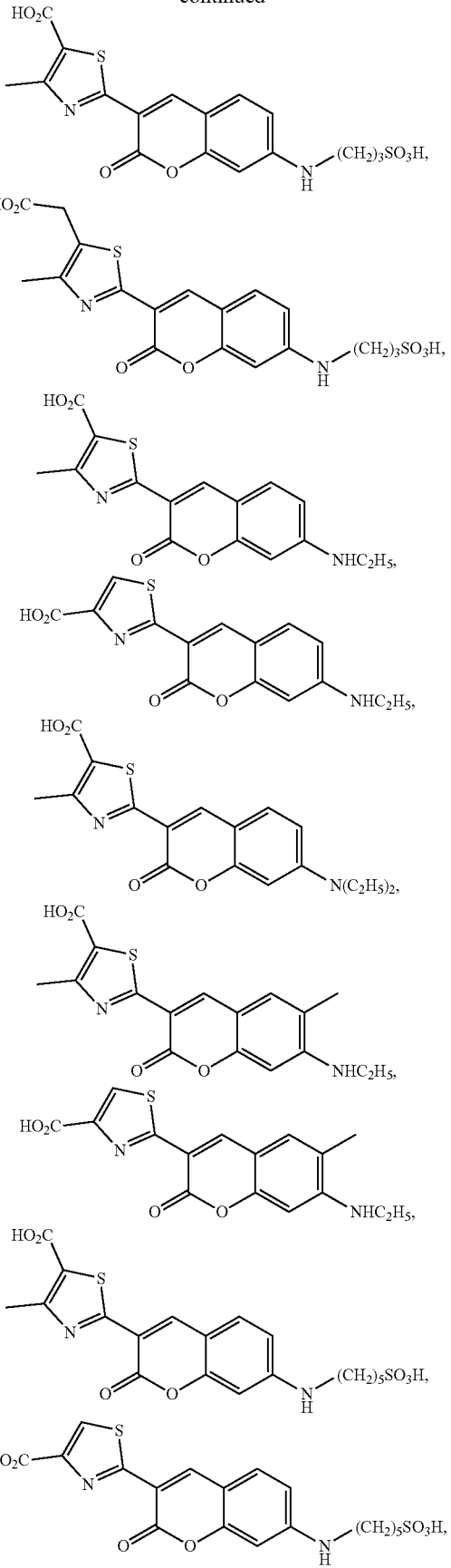

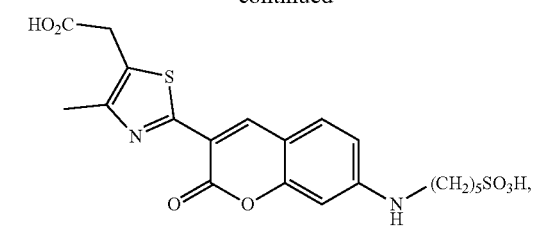
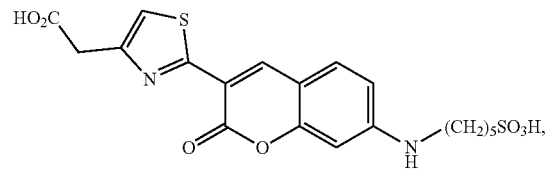
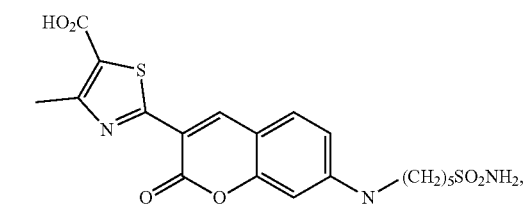
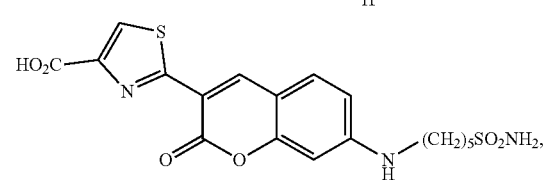
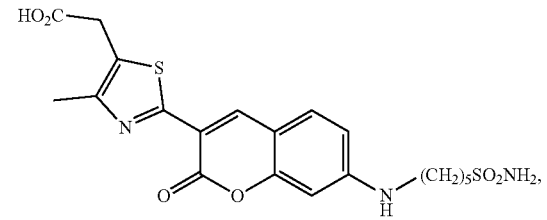
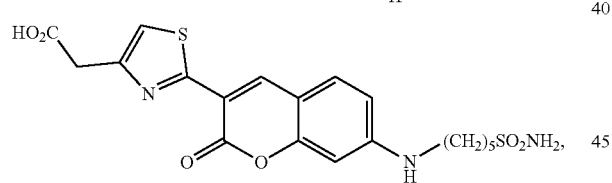
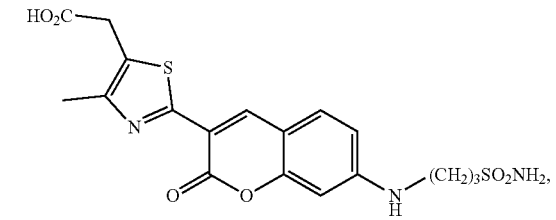
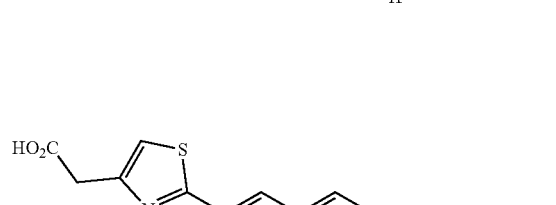
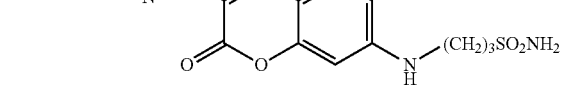
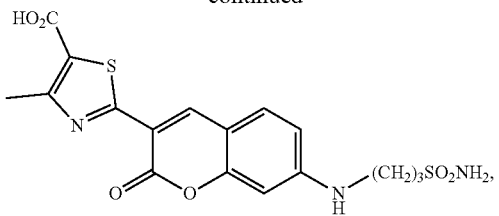
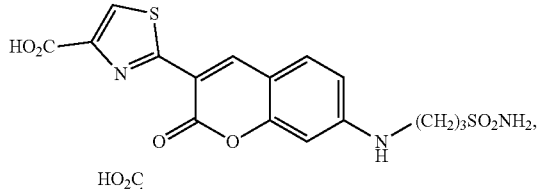
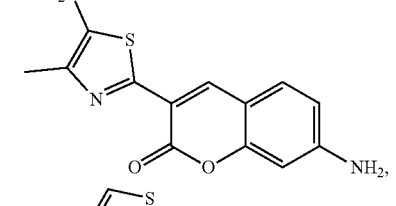
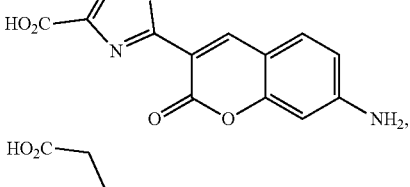
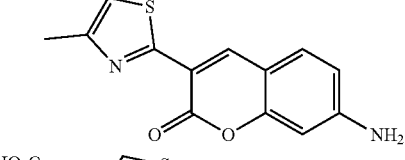
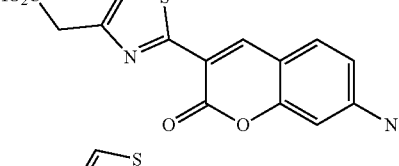
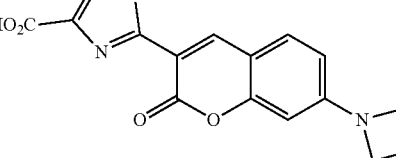
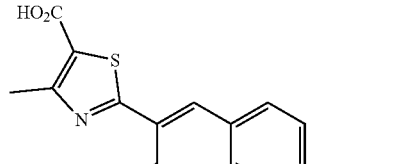
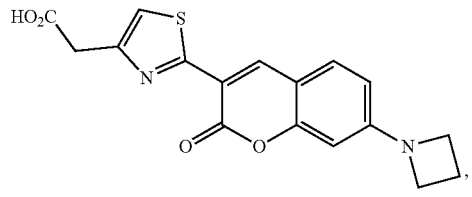

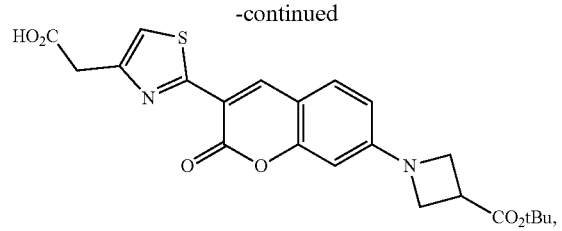
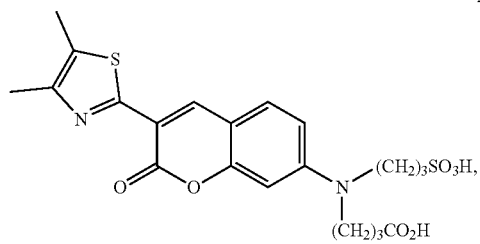
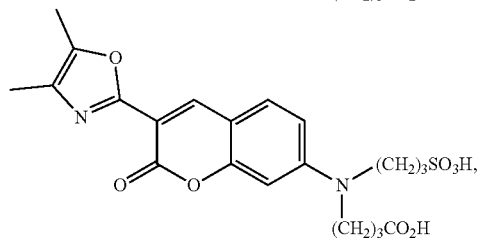
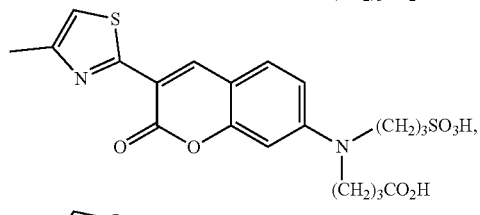
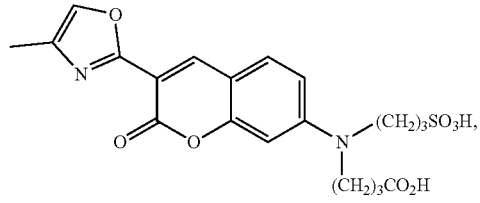
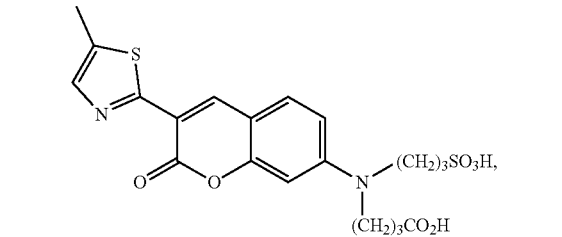
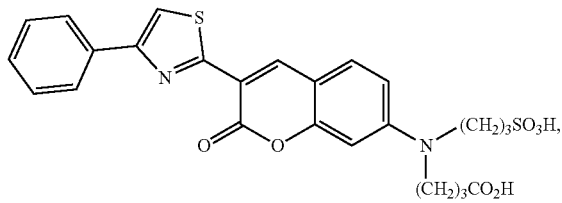
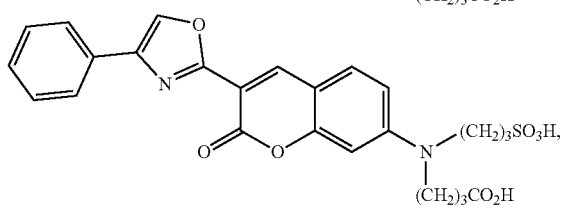
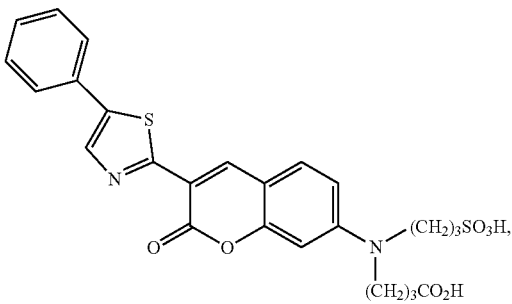
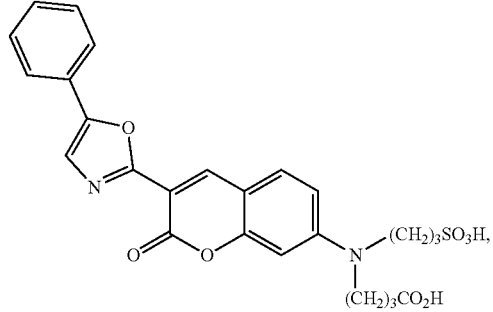
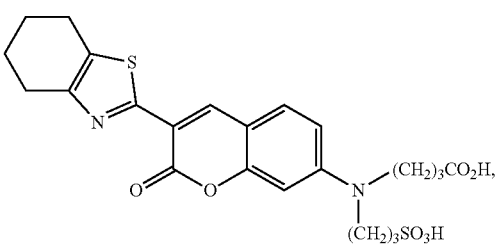
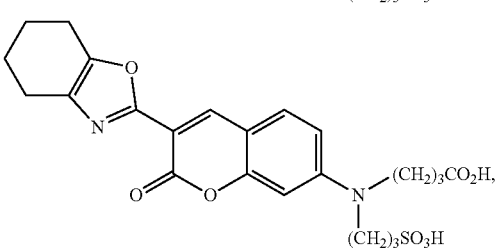
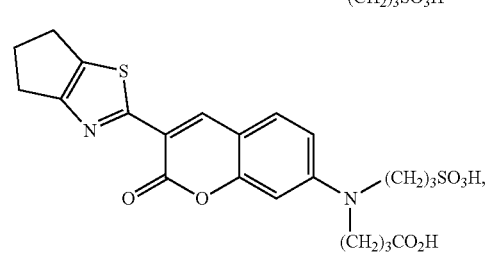
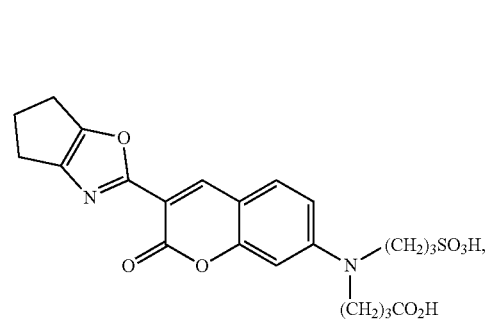

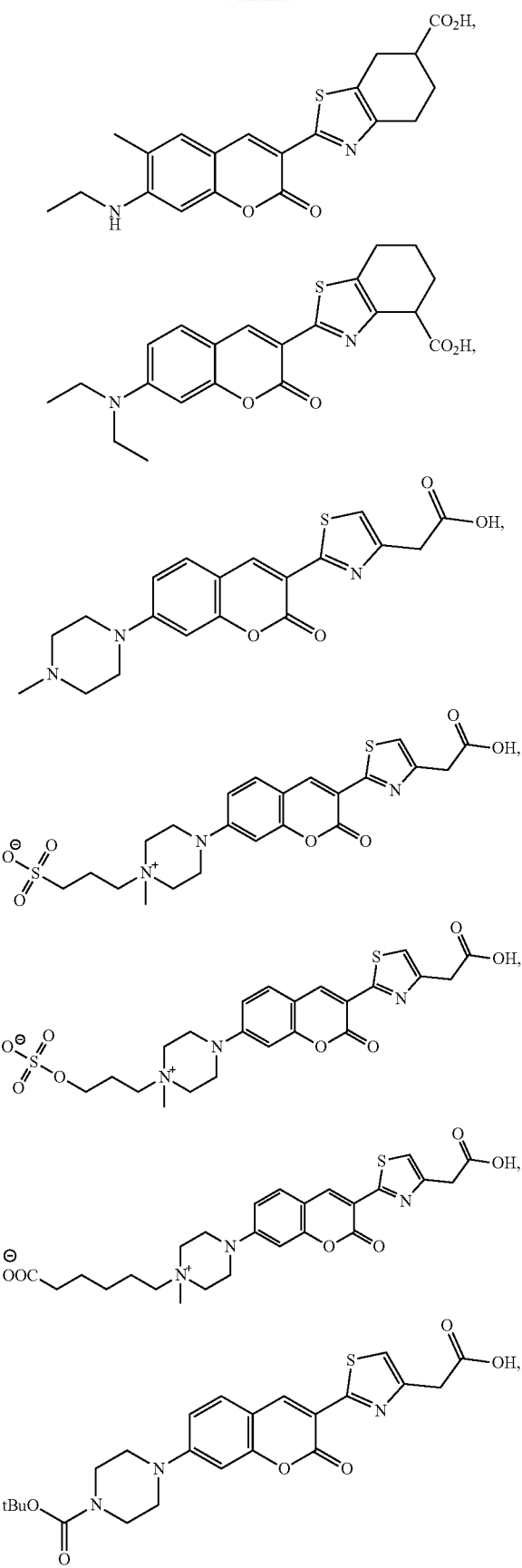

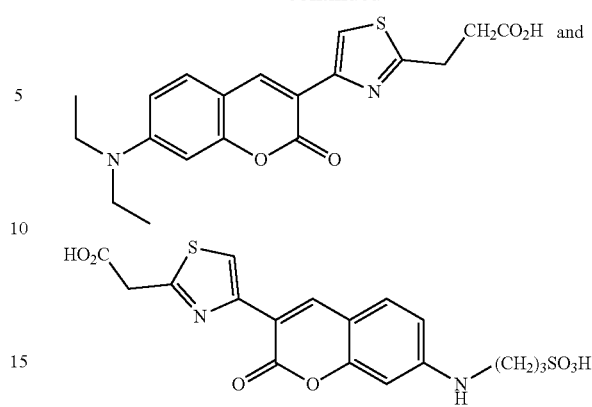

Non-limiting examples also include: corresponding $C_1$-$C_6$ alkyl carboxylic esters (such as methyl esters, ethyl esters isopropyl esters, and t-butyl esters formed from the carboxylic group of the compounds); corresponding imine analogs (where the coumarin core Y position of Formula (IIa) is NH instead of O); corresponding oxazole analog (where the X position of Formula (IIa) is O instead of S); salts and mesomeric forms thereof.

Additional examples of the compounds of Formula (II) or (II') including the following:

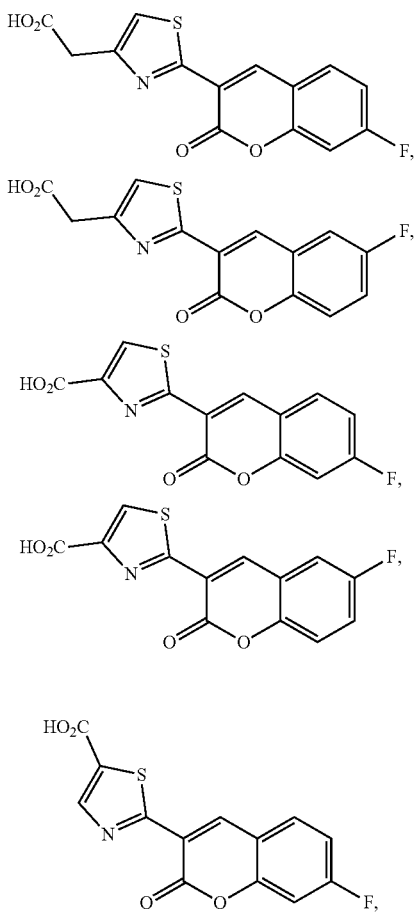

-continued

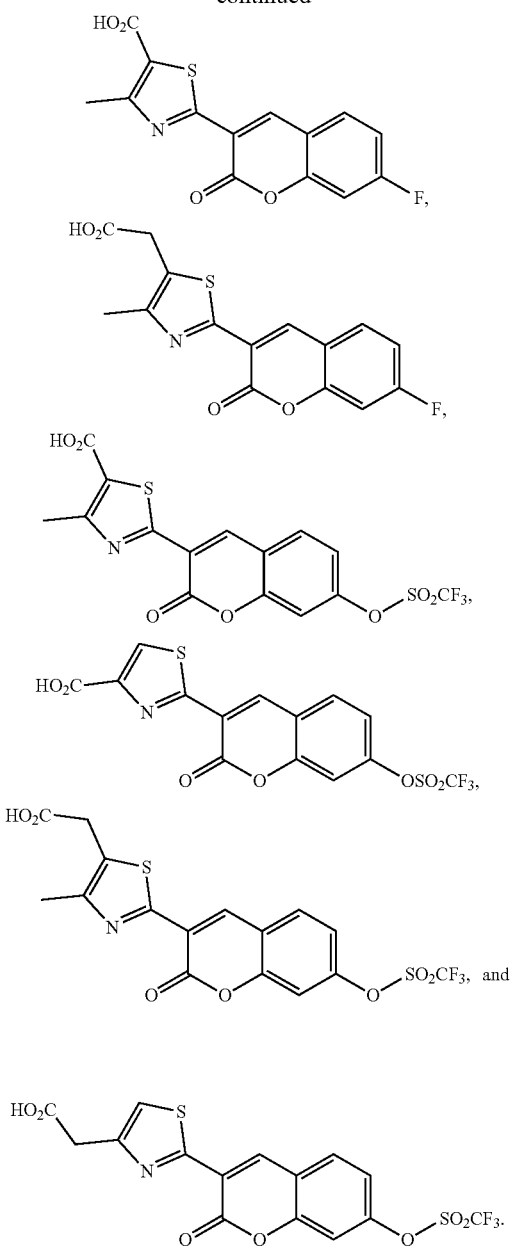

Non-limiting examples also include: corresponding $C_1$-$C_6$ alkyl carboxylic esters (such as methyl esters, ethyl esters isopropyl esters, and t-butyl esters formed from the carboxylic group of the compounds); corresponding bromide analogs (where $R^4$ of Formula (II) or (II') is —Br instead of —F); corresponding imine analogs (where the coumarin core Y position of Formula (II) or (II') is NH instead of O); corresponding oxazole analog (where the X position of Formula (II) or (II') is O instead of S); salts and mesomeric forms thereof.

Cyclooctatetraene (COT) Photo-Protecting Moieties

In some embodiments, the fluorescent compounds described herein (Formula (I), (II) or (II')) may be further modified to introduce a photo-protecting moiety covalently bonded thereto, for example, a cyclooctatetraene moiety comprises the structure:

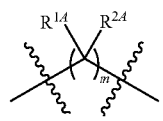

wherein
each of $R^{1A}$ and $R^{2A}$ is independently H, hydroxyl, halogen, azido, thiol, nitro, cyano, optionally substituted amino, carboxyl, —C(O)OR$^{5A}$, —C(O)NR$^{5A}$R$^{6A}$, optionally substituted $C_{1-6}$ alkyl, optionally substituted $C_{1-6}$ alkoxy, optionally substituted $C_{1-6}$ haloalkyl, optionally substituted $C_{1-6}$ haloalkoxy, optionally substituted $C_{2-6}$ alkenyl, optionally substituted $C_{2-6}$ alkynyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

$X^1$ and $Y^1$ are each independently a bond, —O—, —S—, —NR$^{3A}$—, —C(=O)—, —C(=O)—O—, —C(=O)—NR$^{4A}$, —S(O)$_2$—, —NR$^{3A}$—C(=O)—NR$^{4A}$, —NR$^{3A}$—C(=S)—NR$^{4A}$—, optionally substituted $C_{1-6}$ alkylene, or optionally substituted heteroalkylene where at least one carbon atom is replaced with O, S, or N;

$Z^1$ is absent, optionally substituted $C_{2-6}$ alkenylene, or optionally substituted $C_{2-6}$ alkynylene;

each of $R^{3A}$ and $R^{4A}$ is independently H, optionally substituted $C_{1-6}$ alkyl, or optionally substituted $C_{6-10}$ aryl;

each of $R^{5A}$ and $R^{6A}$ is independently H, optionally substituted $C_{1-6}$ alkyl, optionally substituted $C_{6-10}$ aryl, optionally substituted $C_{7-14}$ aralkyl, optionally substituted $C_{3-7}$ carbocyclyl, optionally substituted 5 to 10 membered heteroaryl, or optionally substituted 3 to 10 membered heterocyclyl;

the carbon atom to which $R^{1A}$ and $R^{2A}$ are attached in is optionally replaced with O, S, or N, provided that when said carbon atom is replaced with O or S, then $R^{1A}$ and $R^{2A}$ are both absent; when said carbon atom is replaced with N, then $R^{2A}$ is absent; and m is an integral number between 0 and 10.

In some embodiments of the fluorescent compounds described herein, $X^1$ is —C(=O)— or —C(=O)NR$^{4A}$—. In some such embodiments of $X^1$, $R^{4A}$ is H. In some other embodiments of $X^1$, $R^{4A}$ is $C_{1-6}$ alkyl (e.g., methyl, ethyl, isopropyl or tert-butyl). In some embodiments, $Y^1$ is —C(=O)O—, —NR$^{3A}$— or —S(O)$_2$—. In some such embodiments of $Y^1$, $R^{3A}$ is H, $C_{1-6}$ alkyl or substituted $C_{1-6}$ alkyl (e.g., $C_{1-6}$ alkyl substituted with —CO$_2$H, —NH$_2$, —SO$_3$H, —SO$_3^-$ or —O—SO$_3^-$). In some such embodiments of $Y^1$, $R^{3A}$ is H, $C_{1-6}$ alkyl or substituted $C_{1-6}$ alkyl (e.g., $C_{1-6}$ alkyl substituted with —CO$_2$H, —NH$_2$, —SO$_3$H, —SO$_3^-$ or —O—SO$_3^-$). In some embodiments, $X^1$ and $Y^1$ cannot both be a bond, for example, when $X^1$ is a bond, $Y^1$ is not a bond. In some embodiments, Z is absent. In other embodiments, Z is $C_{2-6}$ alkenylene.

In some embodiments, the cyclooctatetraene moiety comprises the structure:

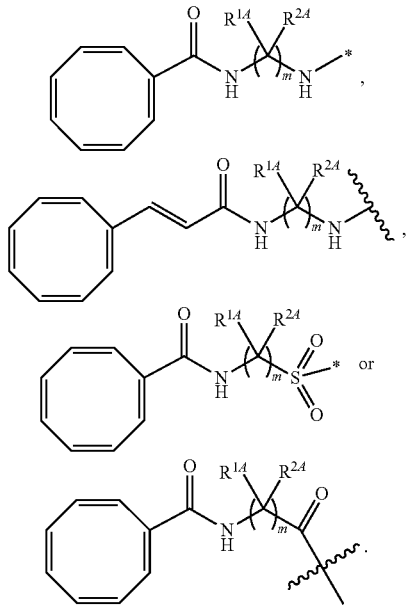

In some such embodiments, at least one of $R^{1A}$ and $R^{2A}$ is hydrogen. In some further embodiments, both $R^{1A}$ and $R^{2A}$ are hydrogen. In some other embodiments, $R^{1A}$ is H and $R^{2A}$ is an optionally substituted amino, carboxyl or —C(O)NR$^{5A}$R$^{6A}$. In some embodiments, m is 1, 2, 3, 4, 5, or 6, and each of $R^{1A}$ and $R^{2A}$ is independently hydrogen, optionally substituted amino, carboxyl, —C(O)NR$^{5A}$R$^{6A}$, or combinations thereof. In some further embodiments, when m is 2, 3, 4, 5, or 6, one $R^{1A}$ is amino, carboxyl, or —C(O)NR$^{5A}$R$^{6A}$, and the remaining $R^{1A}$ and $R^{2A}$ are hydrogen. In some embodiments, at least one carbon atom to which $R^{1A}$ and $R^{2A}$ are attached in

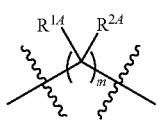

is replaced with O, S, or N. In some such embodiments, one carbon atom in

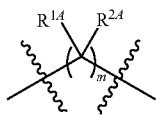

is replaced by an oxygen atom, and both $R^{1A}$ and $R^{2A}$ attached to said replaced carbon atom are absent. In some other embodiments, when one carbon atom in

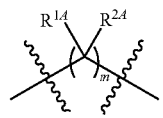

is replaced by an nitrogen atom, $R^{2A}$ attached to said replaced carbon atom is absent, and $R^{1A}$ attached to said replaced carbon atom is hydrogen, or $C_{1-6}$ alkyl. In any embodiments of $R^{1A}$ and $R^{2A}$, when $R^{1A}$ or $R^{2A}$ is —C(O)NR$^{5A}$R$^{6A}$, $R^{5A}$ and $R^{6A}$ may be independently H, $C_{1-6}$ alkyl or substituted $C_{1-6}$ alkyl (e.g., $C_{1-6}$ alkyl substituted with —CO$_2$H, —NH$_2$, —SO$_3$H, or —SO$_3^-$).

In some further embodiments, the fluorescent compounds described herein comprises a cyclooctatetraene moiety of the following structures:

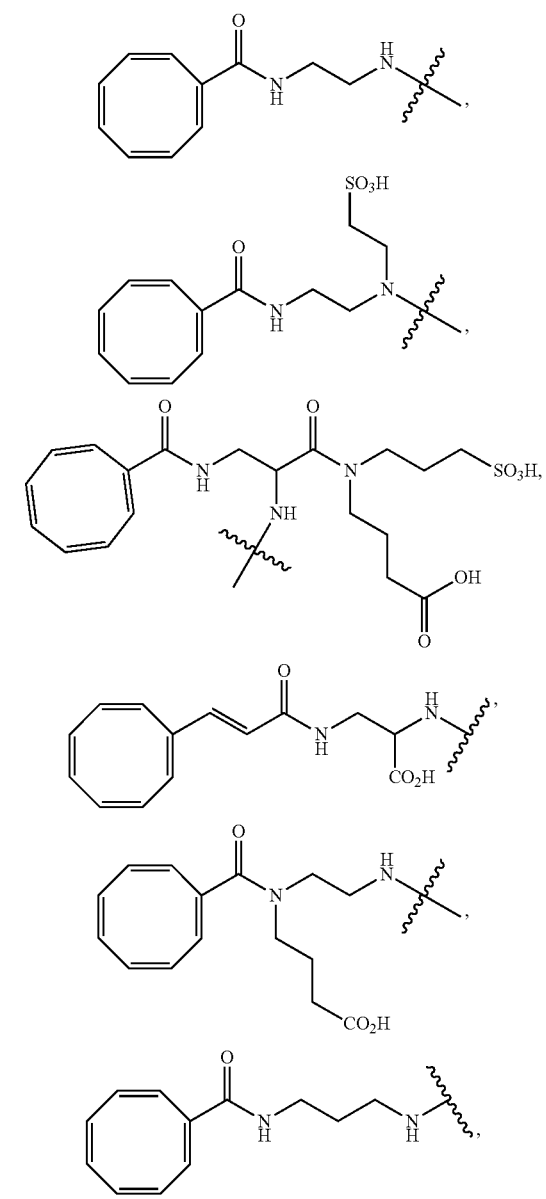

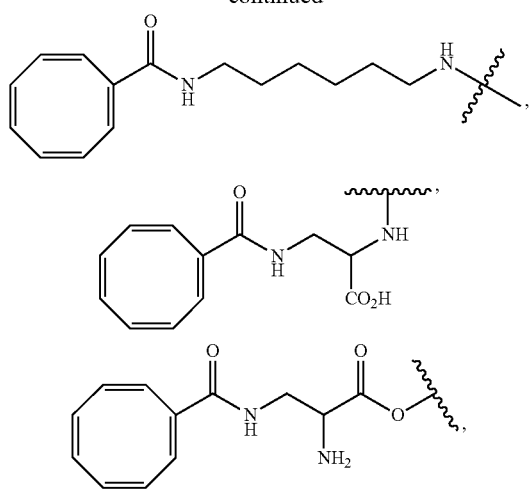
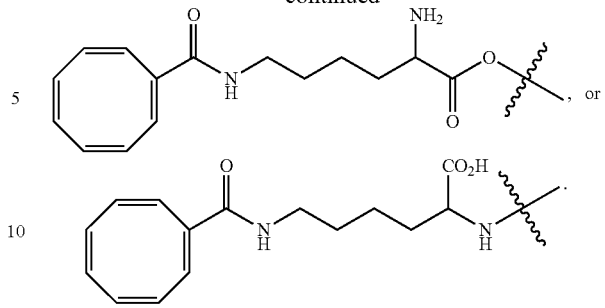
The COT moiety described herein may result from the reaction between a functional group of the fluorescent dye described herein (e.g., a carboxyl group) and an amino group of a COT derivative to form an amide bond (where the carbonyl group of the amide bond is not shown).
Non-limiting examples of COT protected compound of Formula (I) includes:
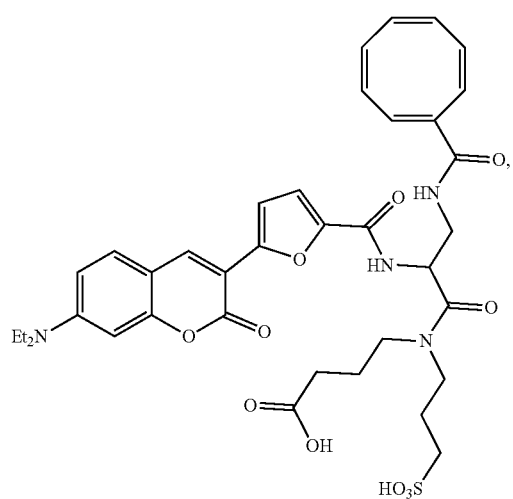
(I-3a)
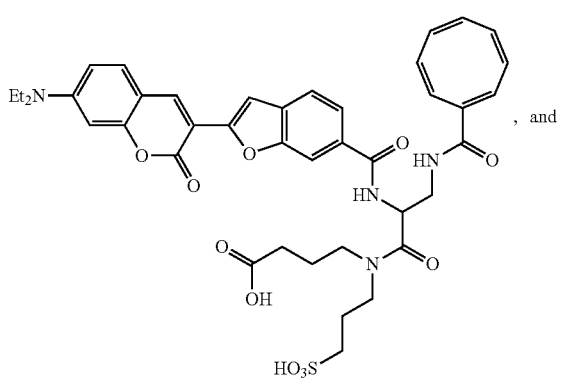
(I-4a), and
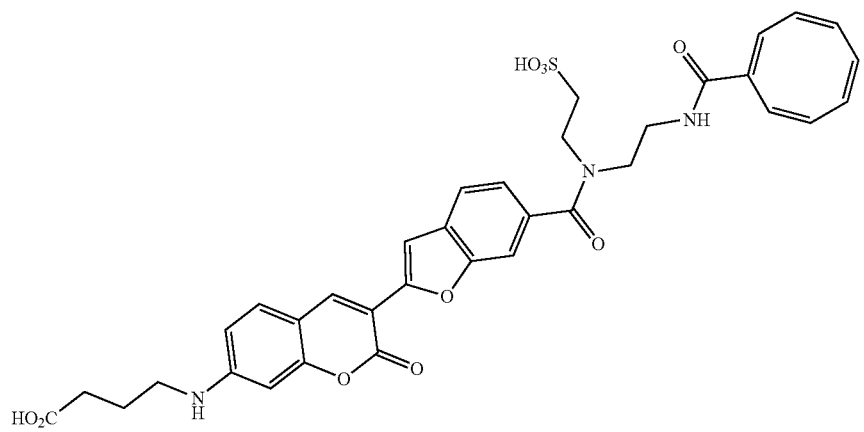
(I-8a)

Labeled Nucleotides or Oligonucleotides

According to an aspect of the disclosure, dye compounds described herein are suitable for attachment to substrate moieties, particularly comprising linker groups to enable attachment to substrate moieties. Substrate moieties can be virtually any molecule or substance to which the dyes of the disclosure can be conjugated, and, by way of non-limiting example, may include nucleosides, nucleotides, polynucleotides, carbohydrates, ligands, particles, solid surfaces, organic and inorganic polymers, chromosomes, nuclei, living cells, and combinations or assemblages thereof. The dyes can be conjugated by an optional linker by a variety of means including hydrophobic attraction, ionic attraction, and covalent attachment. In some aspect, the dyes are conjugated to the substrate by covalent attachment. More particularly, the covalent attachment is by means of a linker group. In some instances, such labeled nucleotides are also referred to as "modified nucleotides."

Some aspects of the present disclosure relate to a nucleotide or oligonucleotide labeled with a dye of Formula (I), (II), (II'), (IIa) or (IIa') as described herein, or a derivative thereof containing a photo-protecting moiety described herein. The labeled nucleotide or oligonucleotide may be attached to the dye compound disclosed herein via a carboxyl (—$CO_2H$) or an alkyl-carboxyl group to form an amide or alkyl-amide bond. In some further embodiments, the carboxyl group may be in the form of an activated form of carboxyl group, for example, an amide or ester, which may be used for attachment to an amino or hydroxyl group of the nucleotide or oligonucleotide The term "activated ester" as used herein, refers to a carboxyl group derivative which is capable of reacting in mild conditions, for example, with a compound containing an amino group. Non-limiting examples of activated esters include but not limited to p-nitrophenyl, pentafluorophenyl and succinimido esters.

For example, the dye compound of Formula (I) may be attached to the nucleotide or oligonucleotide via $R^1$ or one of $R^5/R^6$ of Formula (I). In some such embodiments, $R^1$ of Formula (I) comprises a —$CO_2H$ or —$(CH_2)_{1-6}$—$CO_2H$ and the attachment forms an amide moiety between the carboxyl functional group of $R^1$ and the amino functional group of a nucleotide or a nucleotide linker. As such, the labeled nucleotide or oligonucleotide may comprise the dye moiety of the following structure:

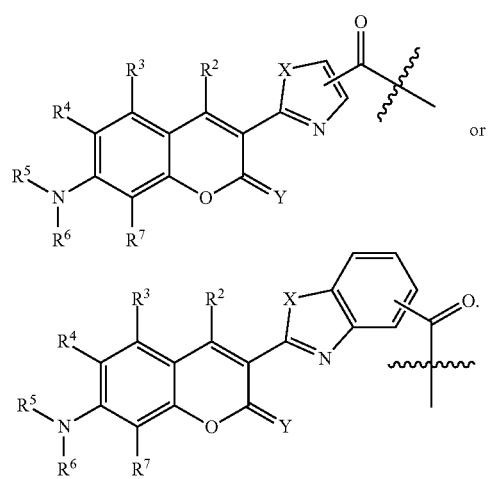

In other embodiments, $R^5$ or $R^6$ of Formula (I) comprises a —$CO_2H$ or —$(CH_2)_{1-6}$—$CO_2H$ and the attachment forms an amide using the —$CO_2H$ group.

Furthermore, the dye compound of Formula (II) or (II') may be attached to the nucleotide or oligonucleotide via $R^6$ or $R^7$ of Formula (II)/(II')/(IIa)/(IIa'); or $R^b$ or $R^c$ of Formula (IIa)/(IIa'). In some such embodiments, $R^6$ or $R^7$ of Formula (II)/(II')/(IIa)/(IIa') comprises a —$CO_2H$ or —$(CH_2)_{1-6}$—$CO_2H$ and the attachment forms an amide moiety between the carboxyl functional group of $R^6$ or $R^7$ and an amino functional group of a nucleotide or a nucleotide linker. As such, the labeled nucleotide or oligonucleotide may comprise the dye moiety of the following structure:

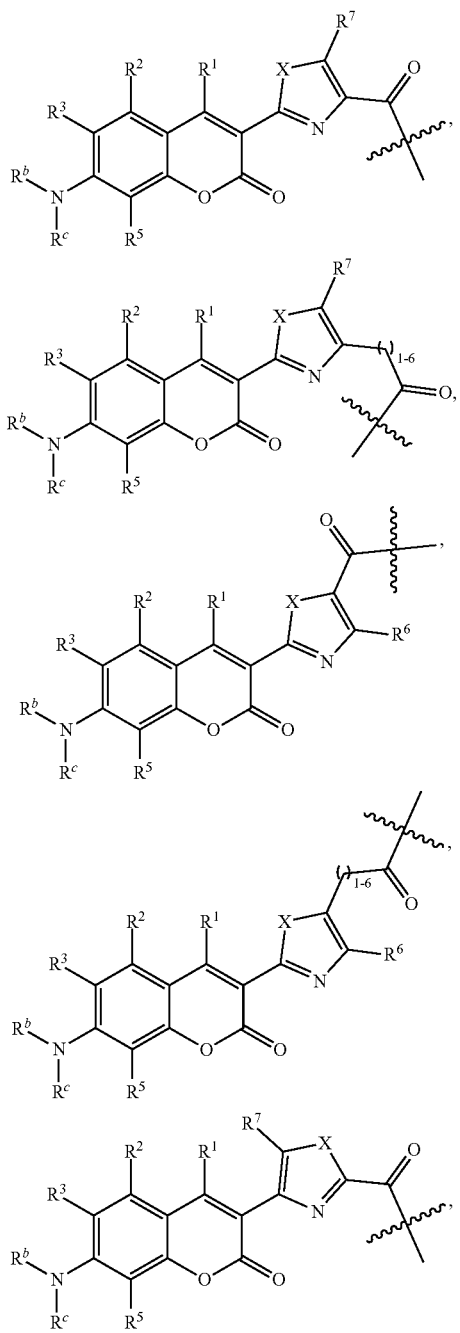

-continued

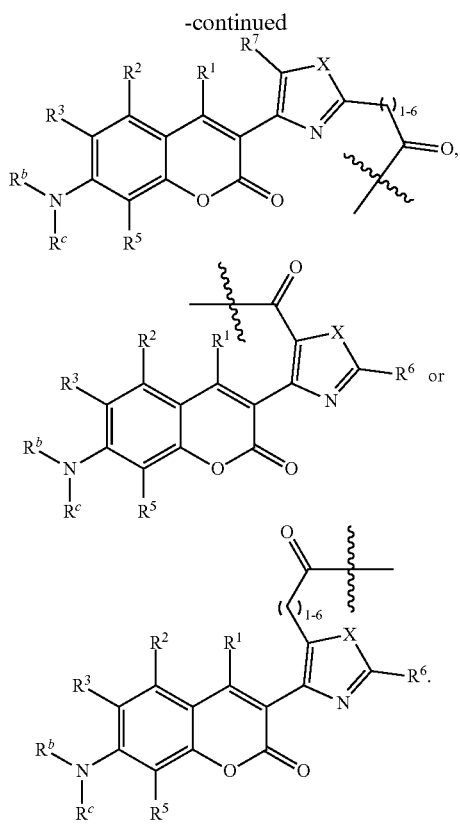

In other embodiments, $R^b$ or $R^c$ of Formula (IIa)/(IIa') comprises a —$CO_2H$ or —$(CH_2)_{1-6}$—$CO_2H$ and the attachment forms an amide using the —$CO_2H$ group.

In some embodiments, the dye compounds may be covalently attached to oligonucleotides or nucleotides via the nucleotide base. In some such embodiments, the labeled nucleotide or oligonucleotide may have the dye attached to the C5 position of a pyrimidine base or the C7 position of a 7-deaza purine base, optionally through a linker moiety. For example, the nucleobase may be 7-deaza adenine and the dye is attached to the 7-deaza adenine at the C7 position, optionally through a linker. The nucleobase may be 7-deaza guanine and the dye is attached to the 7-deaza guanine at the C7 position, optionally through a linker. The nucleobase may be cytosine and the dye is attached to the cytosine at the C5 position, optionally through a linker. As another example, the nucleobase may be thymine or uracil and the dye is attached to the thymine or uracil at the C5 position, optionally through a linker.

3' OH Blocking Groups

The labeled nucleotide or oligonucleotide may also have a blocking group covalently attached to the ribose or deoxyribose sugar of the nucleotide. The blocking group may be attached at any position on the ribose or deoxyribose sugar. In particular embodiments, the blocking group is at the 3' OH position of the ribose or deoxyribose sugar of the nucleotide. Various 3' OH blocking group are disclosed in WO2004/018497 and WO2014/139596, which are hereby incorporated by references. For example, the blocking group may be azidomethyl (—$CH_2N_3$) or substituted azidomethyl (e.g., —$CH(CHF_2)N_3$ or $CH(CH_2F)N_3$), or allyl connecting to the 3' oxygen atom of the ribose or deoxyribose moiety. In some embodiments, the 3' blocking group is azidomethyl, forming 3'-$OCH_2N_3$ with the 3' carbon of the ribose or deoxyribose.

In some other embodiments, the 3' blocking group and the 3' oxygen atoms form an acetal group of the structure

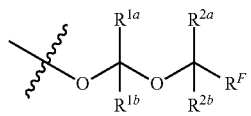

covalent attached to the 3' carbon of the ribose or deoxyribose, wherein:
each $R^{1a}$ and $R^{1b}$ is independently H, $C_1$-$C_6$ alkyl, $C_1$-$C_6$ haloalkyl, $C_1$-$C_6$ alkoxy, $C_1$-$C_6$ haloalkoxy, cyano, halogen, optionally substituted phenyl, or optionally substituted aralkyl;
each $R^{2a}$ and $R^{2b}$ is independently H, $C_1$-$C_6$ alkyl, $C_1$-$C_6$ haloalkyl, cyano, or halogen;
alternatively, $R^{1a}$ and $R^{2a}$ together with the atoms to which they are attached form an optionally substituted five to eight membered heterocyclyl group;
$R^F$ is H, optionally substituted $C_2$-$C_6$ alkenyl, optionally substituted $C_3$-$C_7$ cycloalkenyl, optionally substituted $C_2$-$C_6$ alkynyl, or optionally substituted ($C_1$-$C_6$ alkylene)Si($R^{3a}$)$_3$; and each $R^{3a}$ is independently H, $C_1$-$C_6$ alkyl, or optionally substituted $C_6$-$C_{10}$ aryl.

Additional 3' OH blocking groups are disclosed in U.S. Publication No. 2020/0216891 A1, which is incorporated by reference in its entirety. Non-limiting examples of the acetal blocking group (AOM)

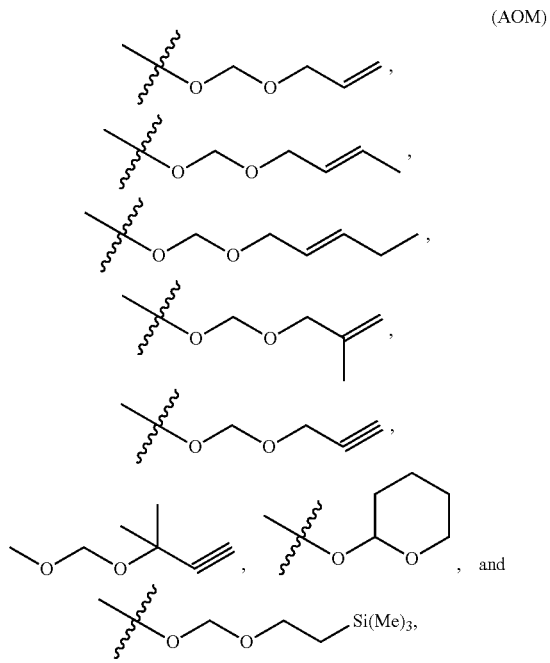

each covalently attached to the 3' carbon of the ribose or deoxyribose.

Linkers

The dye compounds as disclosed herein may include a reactive linker group at one of the substituent positions for covalent attachment of the compound to a substrate or another molecule. Reactive linking groups are moieties capable of forming a bond (e.g., a covalent or non-covalent bond), in particular a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

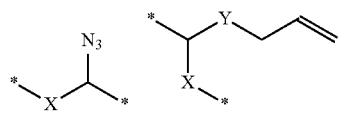

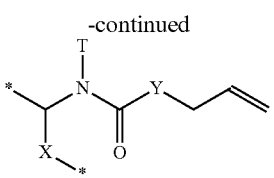

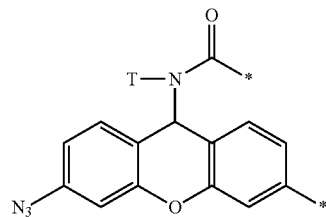

(wherein X is selected from the group comprising O, S, NH and NQ wherein Q is a C1-10 substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide or nucleoside). In some aspect, the linkers connect the bases of nucleotides to labels such as, for example, the dye compounds described herein.

Additional examples of linkers include those disclosed in U.S. Publication No. 2016/0040225 (herein incorporated by reference), such as those include moieties of the formulae:

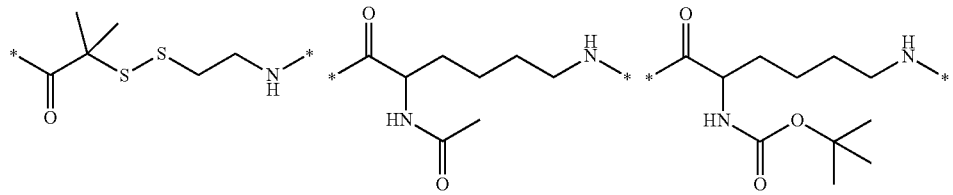

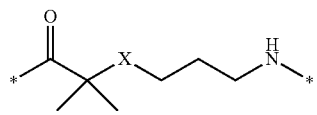

X = $CH_2$, O, S,

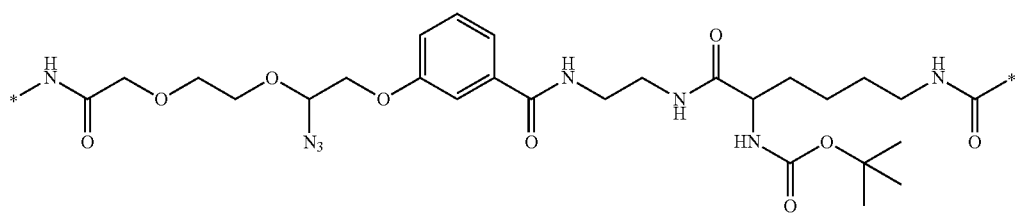

(wherein * indicates where the moiety is connected to the remainder of the nucleotide or nucleoside). The linker moieties illustrated herein may comprise the whole or partial linker structure between the nucleotides/nucleosides and the labels. The linker moieties illustrated herein may comprise the whole or partial linker structure between the nucleotides/nucleosides and the labels.

Additional examples of linkers include moieties of the formula:

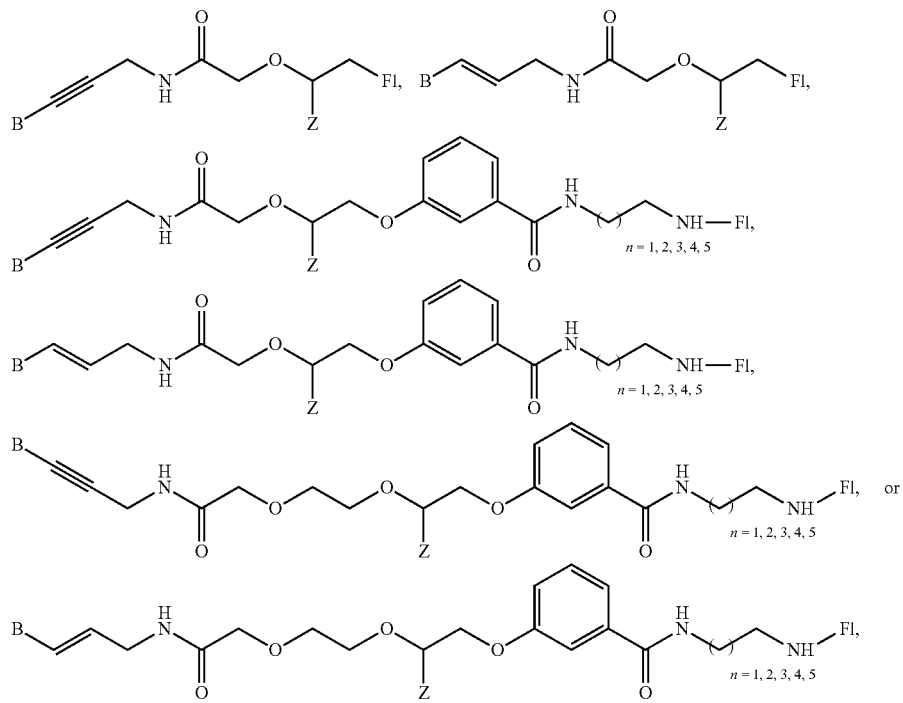

wherein B is a nucleobase; Z is —$N_3$ (azido), —O—$C_1$-$C_6$ alkyl, —O—$C_2$-$C_6$ alkenyl, or —O—$C_2$-$C_6$ alkynyl; and Fl comprises a dye moiety, which may contain additional linker structure. One of ordinary skill in the art understands that the dye compound described herein is covalently bounded to the linker by reacting a functional group of the dye compound (e.g., carboxyl) with a functional group of the linker (e.g., amino). In one embodiment, the cleavable linker comprises

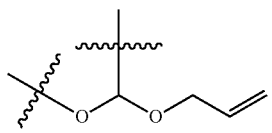

("AOL" linker moiety) where Z is —O-allyl.

In particular embodiments, the length of the linker between a fluorescent dye (fluorophore) and a guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference). The design of linkers, and especially their increased length, can allow improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —(($CH_2$)$_2$O)$_n$—, wherein n is an integer between 2 and 50, as described in WO 2007/020457.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxy group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxy group attached to the C-3 or C-5 of the sugar. Nucleotides are usually mono-, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

A dye may be attached to any position on the nucleotide base, for example, through a linker. In particular embodiments, Watson-Crick base pairing can still be carried out for the resulting analog. Particular nucleobase labeling sites include the C5 position of a pyrimidine base or the C7 position of a 7-deaza purine base. As described above a linker group may be used to covalently attach a dye to the nucleoside or nucleotide.

In particular embodiments the labeled nucleotide or oligonucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the dyes described herein may have the formula:

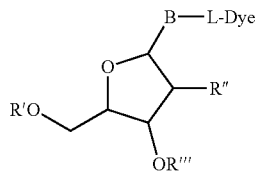

where Dye is a dye compound (label) moiety described herein (after covalent bonding between a functional group of the dye and a functional group of the linker "L"); B is a nucleobase, such as, for example uracil, thymine, cytosine, adenine, 7-deaza adenine, guanine, 7-deaza guanine, and the like; L is an optional linker which may or may not be present; R' can be H, or —OR' is monophosphate, diphosphate, triphosphate, thiophosphate, a phosphate ester analog, —O— attached to a reactive phosphorous containing group, or —O— protected by a blocking group; R" is H or OH; and R'" is H, a phosphoramidite, or a 3' OH blocking group described herein. Where R'" is phosphoramidite, R' is an acid-cleavable hydroxyl protecting group which allows subsequent monomer coupling under automated synthesis conditions. In some further embodiments, B comprises

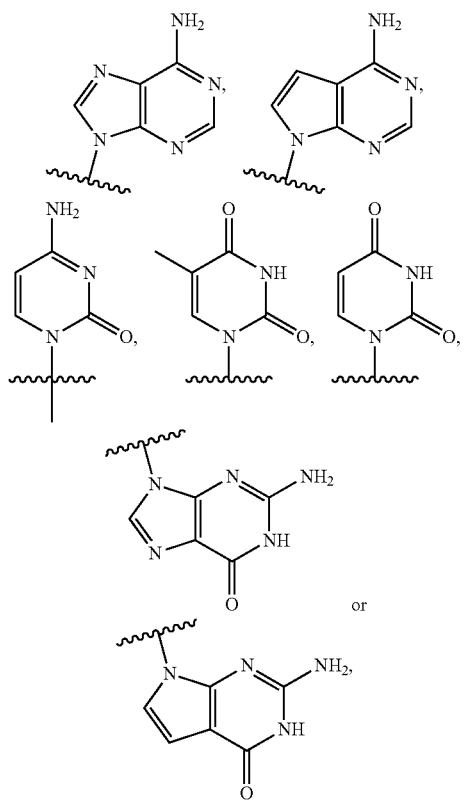

or optionally substituted derivatives and analogs thereof. In some further embodiments, the labeled nucleobase comprises the structure

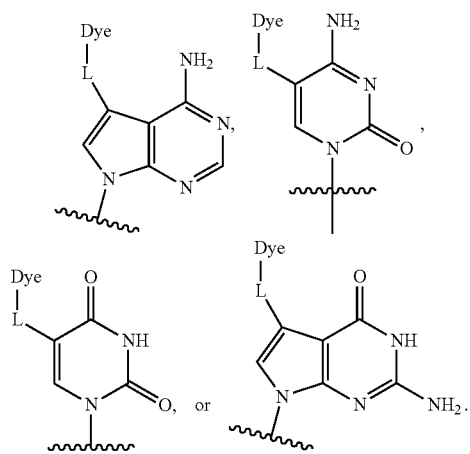

In a particular embodiment, the blocking group is separate and independent of the dye compound, i.e., not attached to it. Alternatively, the dye may comprise all or part of the 3' OH blocking group. Thus R"" can be a 3' OH blocking group which may or may not comprise the dye compound.

In yet another alternative embodiment, there is no blocking group on the 3' carbon of the pentose sugar and the dye (or dye and linker construct) attached to the base, for example, can be of a size or structure sufficient to act as a block to the incorporation of a further nucleotide. Thus, the block can be due to steric hindrance or can be due to a combination of size, charge and structure, whether or not the dye is attached to the 3' position of the sugar.

In still yet another alternative embodiment, the blocking group is present on the 2' or 4' carbon of the pentose sugar and can be of a size or structure sufficient to act as a block to the incorporation of a further nucleotide.

The use of a blocking group allows polymerization to be controlled, such as by stopping extension when a labeled nucleotide is incorporated. If the blocking effect is reversible, for example, by way of non-limiting example by changing chemical conditions or by removal of a chemical block, extension can be stopped at certain points and then allowed to continue.

In a particular embodiment, the linker (between dye and nucleotide) and blocking group are both present and are separate moieties. In particular embodiments, the linker and blocking group are both cleavable under the same or substantially similar conditions. Thus, deprotection and deblocking processes may be more efficient because only a single treatment will be required to remove both the dye compound and the blocking group. However, in some embodiments a linker and blocking group need not be cleavable under similar conditions, instead being individually cleavable under distinct conditions.

The disclosure also encompasses polynucleotides incorporating dye compounds. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one modified nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

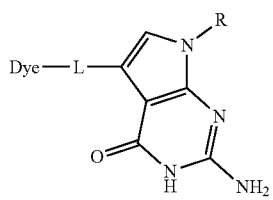
A

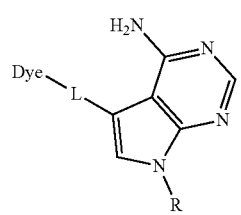
C

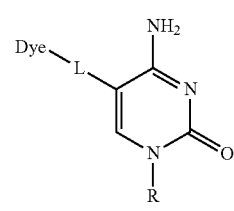
T

-continued

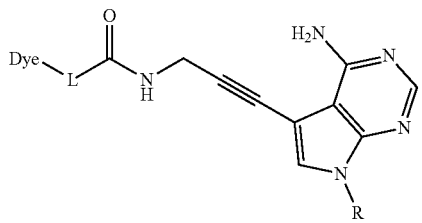
G

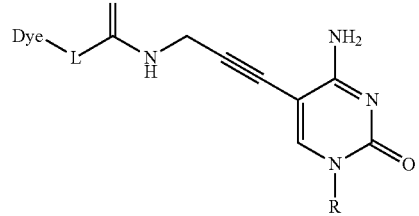
A

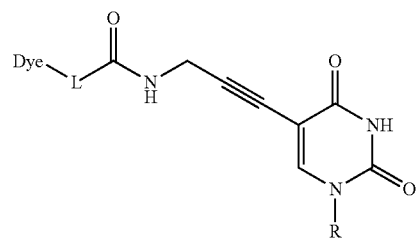
C

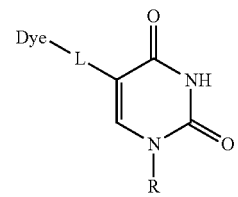
T

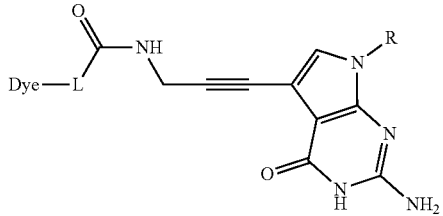
G

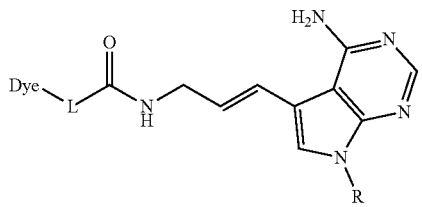
A

C
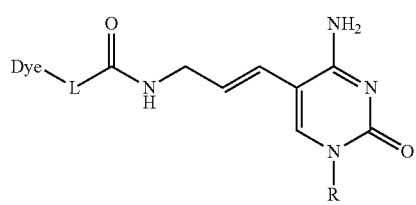
T
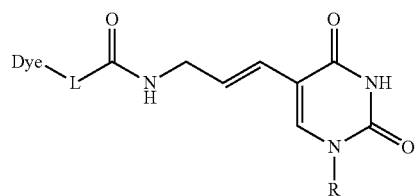
G
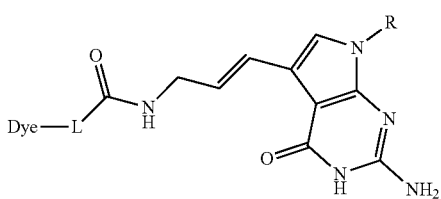
wherein L represents a linker and R represents a ribose or deoxyribose moiety as described above, or a ribose or deoxyribose moiety with the 5' position substituted with mono-, di- or tri-phosphates.
In some embodiments, non-limiting exemplary fluorescent dye conjugates are shown below:
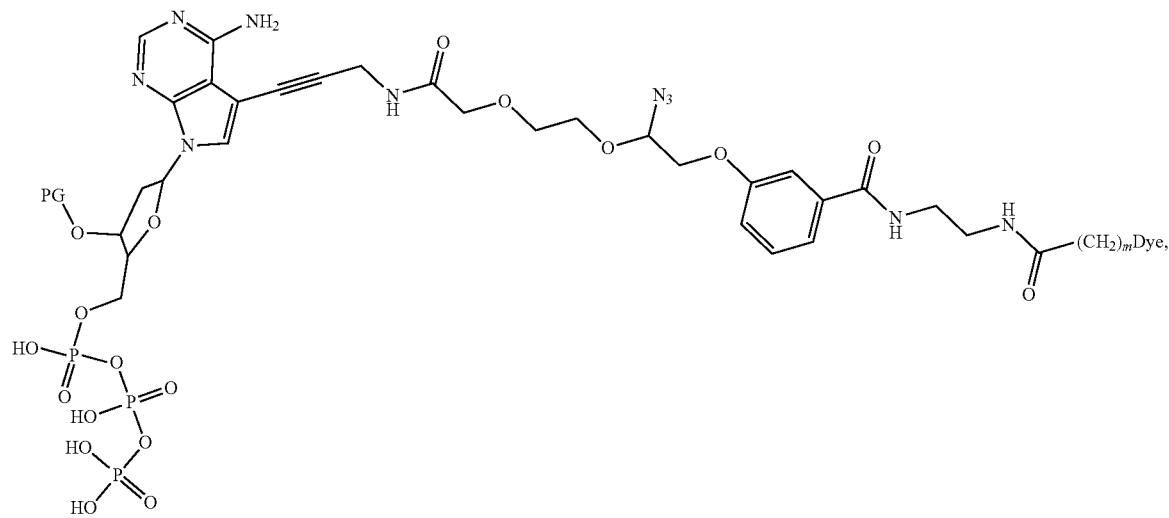
ffA-LN3-Dye
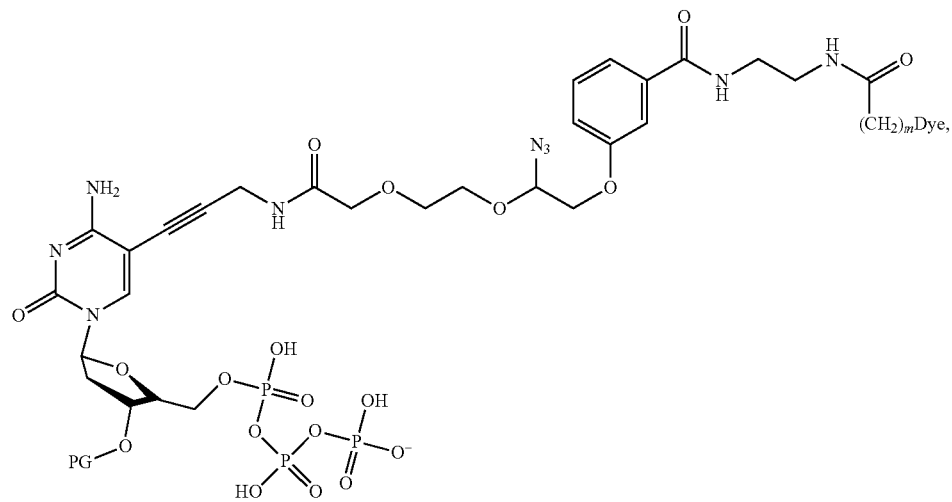
ffC-LN3-Dye

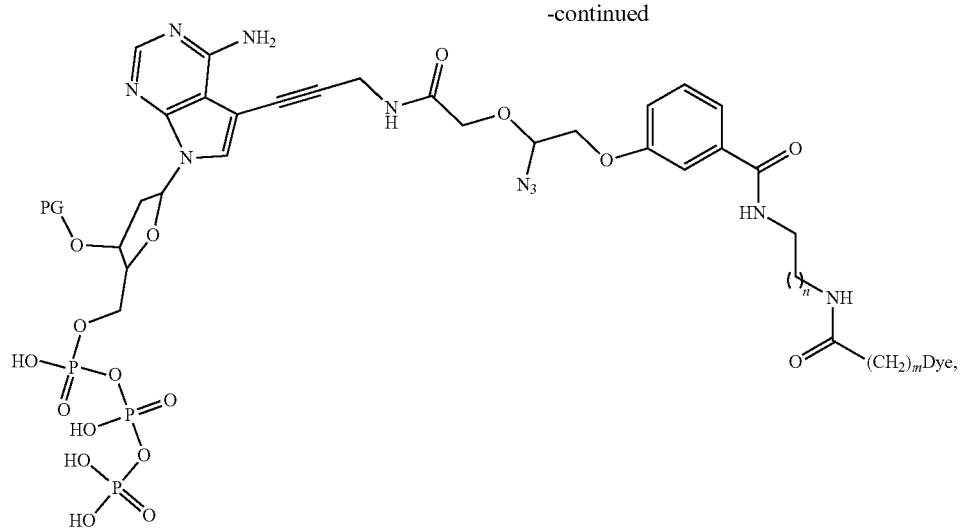
ffA-sPA-LN3-Dye
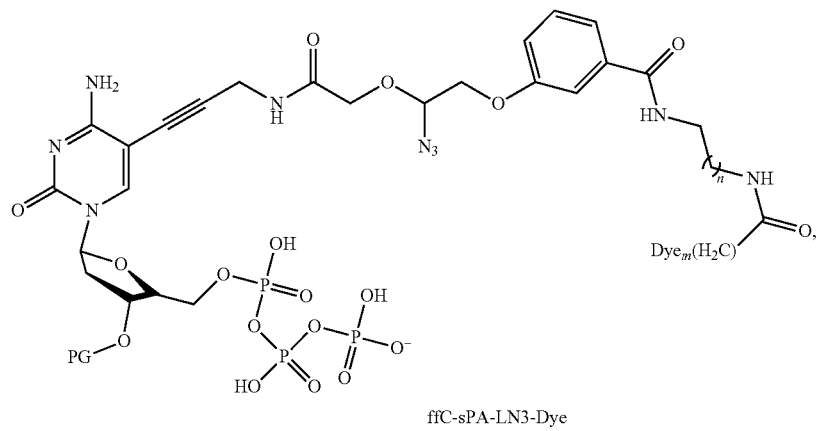
ffC-sPA-LN3-Dye
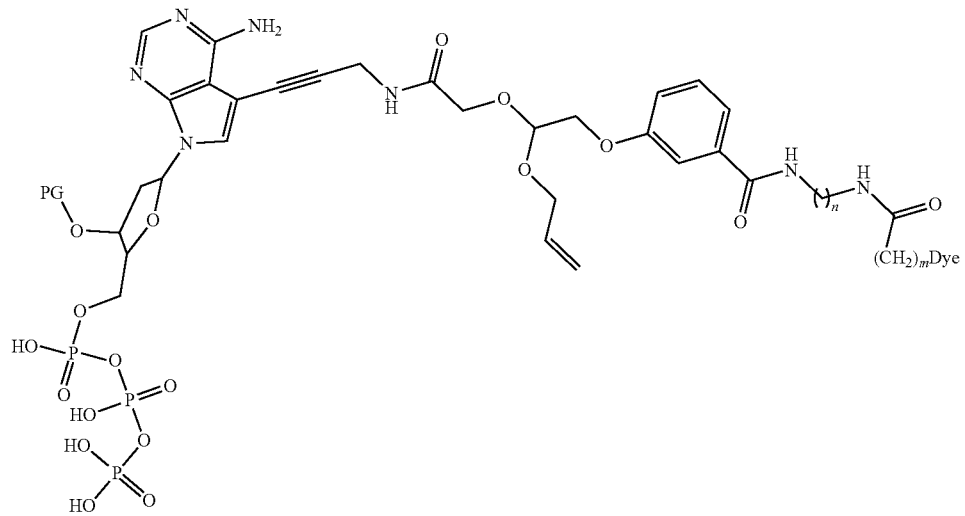
ffA-AOL-Dye

-continued
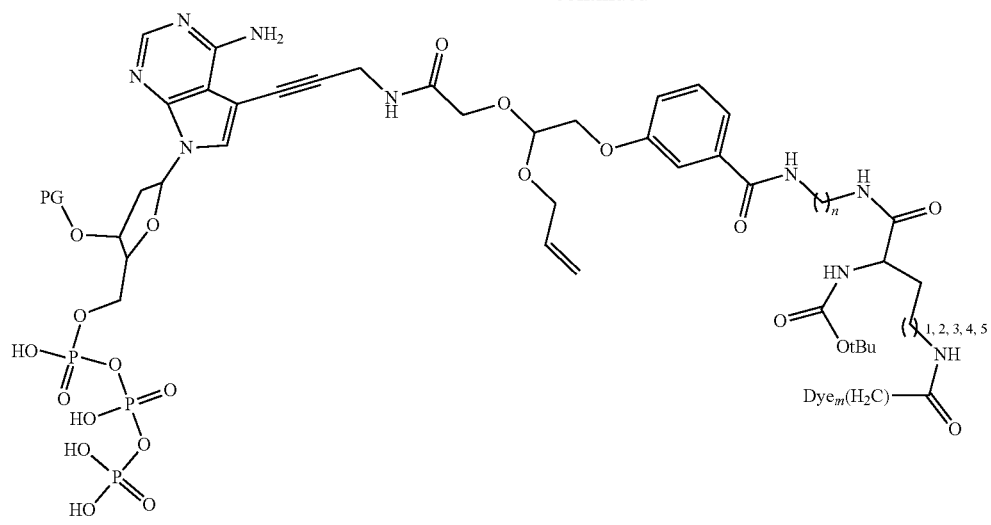
ffA-AOL-BL-Dye
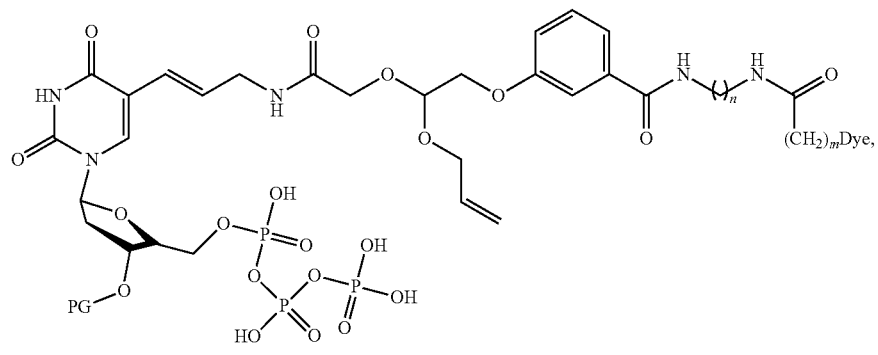
ffT-DB-AOL-Dye
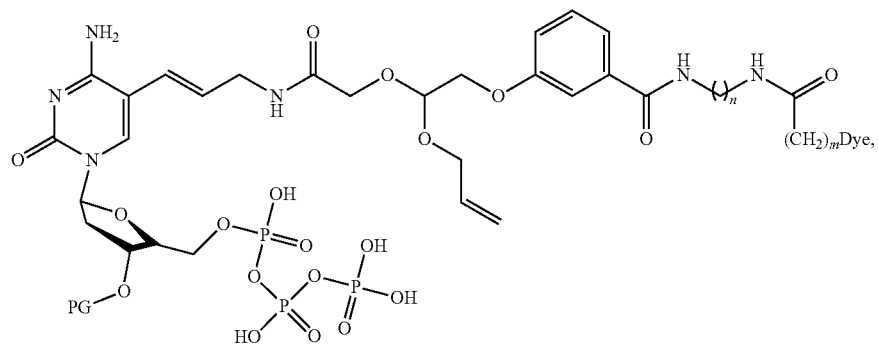
ffC-DB-AOL-Dye

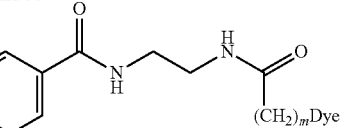
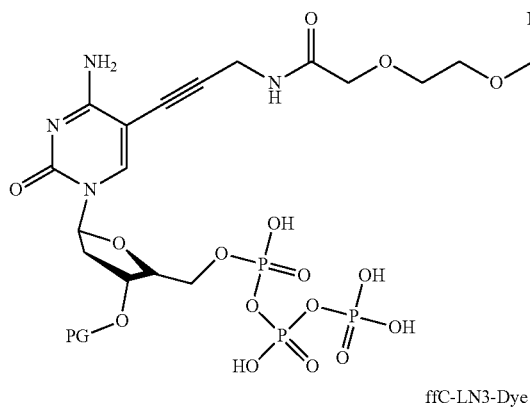

ffC-LN3-Dye wherein PG stands for the 3' OH blocking groups described herein; n is an integer of 1, 2, 3, 4, 5, 6, 7, 8, 9, or 10; and m is 0, 1, 2, 3, 4, or 5. In one embodiment, —O—PG is AOM. In another embodiment, —O—PG is —O-azidomethyl. In one embodiment, n is 5.

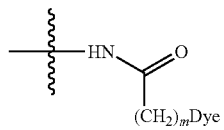

refers to the connection point of the Dye with the cleavable linker as a result of a reaction between an amino group of the linker moiety and the carboxyl group of the Dye. In any embodiments of the labeled nucleotide described herein, the nucleotide is a nucleotide triphosphate.

Additional aspects of the present disclosure relate to an oligonucleotide comprising a labeled nucleotide described herein. In some embodiments, the oligonucleotide is hybridized to at least a portion of a target polynucleotide. In some embodiments, the target polynucleotide is immobilized on a solid support. In some further embodiments, the solid support comprises an array of a plurality of immobilized target polynucleotides.

Kits

Provided herein are kits including one or more nucleotides wherein at least one nucleotide is a nucleotide labeled with a compound of the present disclosure. In some embodiments, the kit comprises a second type of nucleotide and the second type of nucleotide is labeled with a different compound than the first type of labeled nucleotide. In some embodiments, the first and second types of labeled nucleotides are excitable using a single laser wavelength. The kit may include two or more labeled nucleotides. The nucleotides may be labeled with two or more fluorescent labels. Two or more of the labels may be excited using a single excitation source, which may be a laser. For example, the excitation bands for the two or more labels may be at least partially overlapping such that excitation in the overlap region of the spectrum causes both labels to emit fluorescence. In particular embodiments, the emission from the two or more labels will occur in different regions of the spectrum such that presence of at least one of the labels can be determined by optically distinguishing the emission. further comprising a third nucleotide and a fourth nucleotide, wherein each of the second, third, and fourth nucleotides is labeled with a different compound, wherein each label has a distinct absorbance maximum that is distinguishable from the other labels.

In some aspect, the kit may contain four types of labeled nucleotides (A, C, G and T or U, for example, dATP, dCTP, dGTP and dTTP or dUTP), where the first type of four nucleotides is labeled with a compound as disclosed herein. In such a kit, each of the four types nucleotides can be labeled with a compound that is the same or different from the label on the other three nucleotides. Alternatively, a first type of nucleotide is a labeled nucleotide describe herein, a second type of nucleotide is labeled with a second label, a third type of nucleotide is labeled with a third label, and a fourth type of nucleotide is unlabeled (dark). As another example, a first type of nucleotide is a labeled nucleotide described herein, a second type of nucleotide is labeled with a second label, a third type of nucleotide is labeled with a mixture of two labels (i.e., a compound disclosed herein, and the second label), and a fourth type of nucleotide is unlabeled (dark). When one type of nucleotide is labeled with a mixture of two labels, a portion of such type of nucleotide may be labeled with one label (e.g., a compound described herein), and another portion of such type of nucleotide may be labeled with the second label. Thus, one or more of the label compounds can have a distinct absorbance maximum and/or emission maximum such that the compound(s) is(are) distinguishable from other compounds. For example, each compound can have a distinct absorbance maximum and/or emission maximum such that each of the compounds is distinguishable from the other three compounds. It will be understood that parts of the absorbance spectrum and/or emission spectrum other than the maxima can differ and these differences can be exploited to distinguish the compounds. The kit may be such that two or more of the compounds have a distinct absorbance maximum. The compounds of the invention typically absorb light in the region below 500 nm.

The compounds, nucleotides, or kits that are set forth herein may be used to detect, measure, or identify a biological system (including, for example, processes or components thereof). Exemplary techniques that can employ the compounds, nucleotides or kits include sequencing, expression analysis, hybridization analysis, genetic analysis, RNA analysis, cellular assay (e.g., cell binding or cell function analysis), or protein assay (e.g., protein binding assay or protein activity assay). The use may be on an automated instrument for carrying out a particular technique, such as an automated sequencing instrument. The sequencing instrument may contain two lasers operating at different wavelengths.

In a particular embodiment, the labeled nucleotide(s) described herein may be supplied in combination with unlabeled or native nucleotides, or any combination thereof. Combinations of nucleotides may be provided as separate individual components (e.g., one nucleotide type per vessel or tube) or as nucleotide mixtures (e.g., two or more nucleotides mixed in the same vessel or tube).

Where kits comprise a plurality, particularly two, or three, or more particularly four, nucleotides, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary-based DNA sequencing platform) when two or more such dyes are present in one sample. When two nucleotides labeled with fluorescent dye compounds are supplied in kit form, it is a feature of some embodiments that the spectrally distinguishable fluorescent dyes can be excited at the same wavelength, such as, for example by the same laser. When four nucleotides labeled with fluorescent dye compounds are supplied in kit form, it is a feature of some embodiments that two of the spectrally distinguishable fluorescent dyes can both be excited at one wavelength and the other two spectrally distinguishable dyes can both be excited at another wavelength. Particular excitation wavelengths for the dyes are between 450-460 nm, 488 nm, or 532 nm.

In one embodiment, a kit includes a first nucleotide labeled with a compound of the present disclosure and a second nucleotide labeled with a second dye wherein the dyes have a difference in absorbance maximum of at least 10 nm, particularly 20 nm to 50 nm. More particularly, the two dye compounds have Stokes shifts of between 15-40 nm where "Stokes shift" is the distance between the peak absorption and peak emission wavelengths.

In a further embodiment, a kit can further include two other nucleotides labeled with fluorescent dyes wherein the dyes are excited by the same laser at 532 nm. The dyes can have a difference in absorbance maximum of at least 10 nm, particularly 20 nm to 50 nm. More particularly the two dye compounds can have Stokes shifts of between 20-40 nm. Particular dyes which are spectrally distinguishable from dyes of the present disclosure and which meet the above criteria are polymethine analogues as described in U.S. Pat. No. 5,268,486 (for example Cy3) or WO 0226891 (Alexa 532; Molecular Probes A20106) or unsymmetrical polymethines as disclosed in U.S. Pat. No. 6,924,372, each of which is incorporated herein by reference. Alternative dyes include rhodamine analogues, for example tetramethyl rhodamine and analogues thereof.

In an alternative embodiment, the kits of the disclosure may contain nucleotides where the same base is labeled with two different compounds. A first nucleotide may be labeled with a compound of the disclosure. A second nucleotide may be labeled with a spectrally distinct compound, for example a 'green' dye absorbing at less than 600 nm. A third nucleotide may be labeled as a mixture of the compound of the disclosure and the spectrally distinct compound, and the fourth nucleotide may be 'dark' and contain no label. In simple terms, therefore, the nucleotides 1-4 may be labeled 'blue', 'green', 'blue/green', and dark. To simplify the instrumentation further, four nucleotides can be labeled with two dyes excited with a single laser, and thus the labeling of nucleotides 1-4 may be 'blue 1', 'blue 2', 'blue 1/blue 2', and dark.

Nucleotides may contain two dyes of the present disclosure. A kit may contain two or more nucleotides labeled with dyes of the disclosure. Kits may contain a further nucleotide where the nucleotide is labeled with a dye that absorbs in the region of 520 nm to 560 nm. Kits may further contain an unlabeled nucleotide.

Although kits are exemplified herein in regard to configurations having different nucleotides that are labeled with different dye compounds, it will be understood that kits can include 2, 3, 4 or more different nucleotides that have the same dye compound.

In addition to the labeled nucleotides, the kit may comprise together at least one further component. The further component(s) may be one or more of the components identified in a method set forth herein or in the Examples section below. Some non-limiting examples of components that can be combined into a kit of the present disclosure are set forth below. In some embodiments, the kit further comprises a DNA polymerase (such as a mutant DNA polymerase) and one or more buffer compositions. One buffer composition may comprise antioxidants such as ascorbic acid or sodium ascorbate, which can be used to protect the dye compounds from photo damage during detection. Additional buffer composition may comprise a reagent can may be used to cleave the 3' blocking group and/or the cleavable linker. For example, a water-soluble phosphines or water-soluble transition metal catalysts formed from a transition metal and at least partially water-soluble ligands, such as a palladium complex. Various components of the kit may be provided in a concentrated form to be diluted prior to use. In such embodiments a suitable dilution buffer may also be included. Again, one or more of the components identified in a method set forth herein can be included in a kit of the present disclosure.

Methods of Preparation

Disclosed herein are methods of synthesizing compounds of the disclosure. Dyes according to the present disclosure may be synthesized from a variety of different suitable starting materials. For example, compounds of Formula (IIa) may be prepared by reacting a compound of Formula (III) with an amine of formula $NHR^bR^c$:

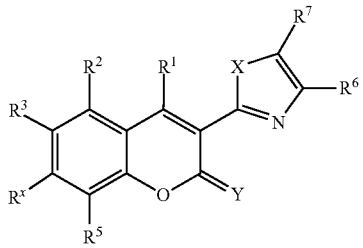

(III)

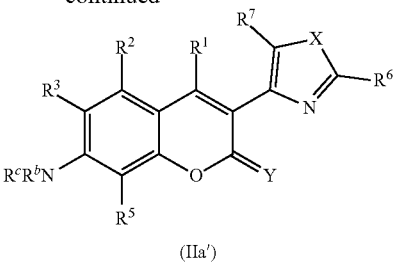

(IIa')

wherein X is S, O, or NR$^a$;
Y is O or NH;
each R$^1$, R$^2$, R$^3$ and R$^5$ is independently H, optionally substituted C$_1$-C$_6$ alkyl, C$_1$-C$_6$ alkoxy, C$_2$-C$_6$ alkenyl, C$_2$-C$_6$ alkynyl, C$_1$-C$_6$ haloalkyl, C$_1$-C$_6$ haloalkoxy, C$_1$-C$_6$ hydroxyalkyl, (C$_1$-C$_6$ alkoxy)(C$_1$-C$_6$ alkyl), optionally substituted amino, halo, cyano, hydroxy, nitro, sulfonyl, sulfino, sulfo, sulfonate, S-sulfonamido, N-sulfonamido, optionally substituted C$_3$-C$_{10}$ carbocyclyl, optionally substituted C$_6$-C$_{10}$ aryl, optionally substituted 5 to 10 membered heteroaryl, or optionally substituted 3 to 10 membered heterocyclyl;
each of R$^6$ and R$^7$ is independently H, carboxyl, —C(O)NR$^b$R$^c$, —C(O)OR$^d$, C$_1$-C$_6$ alkyl, substituted C$_1$-C$_6$ alkyl, C$_1$-C$_6$ haloalkyl, halo, optionally substituted amino, N-sulfonamido, sulfonyl, S-sulfonamido, hydroxy, cyano, nitro, optionally substituted phenyl, optionally substituted C$_3$-C$_8$ carbocyclyl, optionally substituted 5 to 10 membered heteroaryl, or optionally substituted 3 to 10 membered heterocyclyl; or R$^6$ and R$^7$ together with the atoms to which they are attached form an optionally substituted C$_5$-C$_8$ carbocyclyl or an optionally substituted 5 to 8 membered heterocyclyl;
each of R$^6$ and R$^7$ is independently H, carboxyl, —C(O)NR$^b$R$^c$, —C(O)OR$^d$, C$_1$-C$_6$ alkyl, substituted C$_1$-C$_6$ alkyl, halo, optionally substituted amino, hydroxy, or optionally substituted phenyl; or R$^6$ and R$^7$ together with the atoms to which they are attached form an optionally substituted C$_5$-C$_8$ carbocyclyl;
R$^x$ is halo, —OR$^d$ or —OS(O)$_2$R$^d$;
R$^a$ is H or C$_1$-C$_6$ alkyl;
each R$^b$ and R$^c$ is independently H, C$_1$-C$_6$ alkyl, or substituted C$_1$-C$_6$ alkyl; or R$^b$ and R' together with the nitrogen atom to which they are attached form an optionally substituted 4 to 10 membered heterocyclyl; and
each R$^d$ is independently optionally substituted C$_1$-C$_6$ alkyl or optionally substituted phenyl.

The reaction may be conducted in organic solvents at ambient or elevated temperature. Similarly, compounds of Formula (IIa') may be prepared by reacting a compound of Formula (III') with an amine of formula NHR$^b$R$^c$, where the variables in the structures are defined herein.

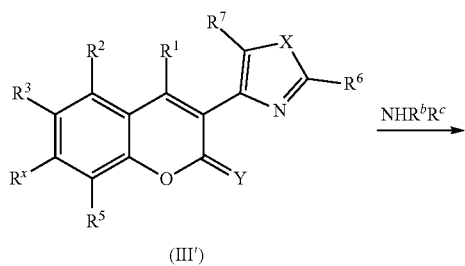

(III')

Methods of Sequencing

Nucleotides comprising a dye compound according to the present disclosure may be used in any method of analysis such as method that include detection of a fluorescent label attached to such nucleotide, whether on its own or incorporated into or associated with a larger molecular structure or conjugate. In this context the term "incorporated into a polynucleotide" can mean that the 5' phosphate is joined in phosphodiester linkage to the 3' hydroxyl group of a second nucleotide, which may itself form part of a longer polynucleotide chain. The 3' end of a nucleotide set forth herein may or may not be joined in phosphodiester linkage to the 5' phosphate of a further nucleotide. Thus, in one non-limiting embodiment, the disclosure provides a method of detecting a labeled nucleotide incorporated into a polynucleotide which comprises: (a) incorporating at least one labeled nucleotide of the disclosure into a polynucleotide and (b) determining the identity of the nucleotide(s) incorporated into the polynucleotide by detecting the fluorescent signal from the dye compound attached to said nucleotide(s).

This method can include: a synthetic step (a) in which one or more labeled nucleotides according to the disclosure are incorporated into a polynucleotide and a detection step (b) in which one or more labeled nucleotide(s) incorporated into the polynucleotide are detected by detecting or quantitatively measuring their fluorescence.

Some embodiments of the present application are directed to a method of determining the sequence of a single-stranded target polynucleotide, comprising: (a) contacting a primer polynucleotide/target polynucleotide complex with one or more labeled nucleotides (such as nucleoside triphosphates A, G, C and T), wherein at least one of said labeled nucleotide is a labeled nucleotide described herein, and wherein the primer polynucleotide is complementary to at least a portion of the target polynucleotide; (b) incorporating a labeled nucleotide into the primer polynucleotide; and (c) performing one or more fluorescent measurements to determine the identity of the incorporated nucleotide. In some such embodiments, the primer polynucleotide/target polynucleotide complex is formed by contacting the target polynucleotide with a single-stranded primer polynucleotide complementary to at least a portion of the target polynucleotide. In some embodiments, the method further comprises (d) removing the label moiety and the 3' blocking group from the nucleotide incorporated into the primer polynucleotide. In some further embodiments, the method may also comprise (e) washing the removed label moiety and the 3' blocking group away from the primer polynucleotide strand. In some embodiments, steps (a) through (d) or steps (a) through (e) are repeated until a sequence of at least a portion of the target polynucleotide strand is determined. In some instances, steps (a) through (d) or steps (a) through (e) are repeated at least 50, 60, 70, 80, 90, 100, 110, 120, 130, 140, 150, 160, 170, 180, 190 or 200 times. In some embodiments, the label moiety and the 3' blocking group from the nucleotide incorporated into the primer polynucleotide strand are removed in a single chemical reaction. In some further embodiments, the method is performed on an automated sequencing instrument, and wherein the automated sequencing instrument comprises two light sources operating at different wavelengths.

In one embodiment, at least one nucleotide is incorporated into a polynucleotide (such as a single stranded primer polynucleotide described herein) in the synthetic step by the action of a polymerase enzyme. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template or target polynucleotide strand with a reaction mixture comprising fluorescently labeled nucleotides of the disclosure. A polymerase can also be provided under conditions which permit formation of a phosphodiester linkage between a free 3' hydroxyl group on a polynucleotide strand annealed to the template or target polynucleotide strand and a 5' phosphate group on the labeled nucleotide. Thus, a synthetic step can include formation of a polynucleotide strand as directed by complementary base-pairing of nucleotides to a template/target strand.

In all embodiments of the methods, the detection step may be carried out while the polynucleotide strand into which the labeled nucleotides are incorporated is annealed to a template/target strand, or after a denaturation step in which the two strands are separated. Further steps, for example chemical or enzymatic reaction steps or purification steps, may be included between the synthetic step and the detection step. In particular, the polynucleotide strand incorporating the labeled nucleotide(s) may be isolated or purified and then processed further or used in a subsequent analysis. By way of example, polynucleotide strand incorporating the labeled nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including the labeled nucleotides as described herein, to form an extended polynucleotide strand (primer polynucleotide strand) complementary to the template/target strand in the presence of a suitable polymerase enzyme. In other embodiments, the synthetic step may itself form part of an amplification reaction producing a labeled double stranded amplification product comprised of annealed complementary strands derived from copying of the primer and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of the labeled nucleotides as set forth herein. A variety of naturally occurring or mutant/modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the labeled nucleotides according to the disclosure include those described in WO 2005/024010 or WO06120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the modified nucleotide or nucleoside labeled with dyes set forth herein when incorporated into a polynucleotide.

In a particular embodiment the disclosure provides use of labeled nucleotides comprising dye moiety according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template/target nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the nucleotides labeled with dyes set forth herein for determination of the identity of a single base may be useful, for example, in the scoring of single nucleotide polymorphisms, and such single base extension reactions are within the scope of this disclosure.

In an embodiment of the present disclosure, the sequence of a template/target polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template/target polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3' blocking group and fluorescent dye compounds can then be removed (deprotected) (simultaneously or sequentially) to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group that serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments, sequencing may proceed by strand displacement. In certain embodiments, a primer bearing the free 3' hydroxyl group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO0157248 and WO2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to a support (for example, silica-based supports such as those disclosed in WO00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO2005/047301 (incorporated herein by reference). A still further example of solid-supported template polynucleotides is where the template polynucleotides are attached to hydrogel supported upon silica-based or other solid supports, for example, as described in WO00/31148, WO01/01143, WO02/12566, WO03/014392, U.S. Pat. No. 6,465,178 and WO00/53812, each of which is incorporated herein by reference.

A particular surface to which template polynucleotides may be immobilized is a polyacrylamide hydrogel. Polyacrylamide hydrogels are described in the references cited above and in WO2005/065814, which is incorporated herein by reference. Specific hydrogels that may be used include those described in WO2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in Nature, 437, 376-380 (2005); Science, 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high-density arrays, including single-molecule arrays, clustered arrays, and bead arrays. Nucleotides labeled with dye compounds of the present disclosure may be used for sequencing templates on essentially any type of array, including but not limited to those formed by immobilization of nucleic acid molecules on a solid support.

However, nucleotides labeled with dye compounds of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using nucleotides labeled with dye compounds of the disclosure.

Nucleotides labeled with dye compounds of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO 00/06770 and WO 01/57248, each of which is incorporated herein by reference. Although one use of the labeled nucleotides of the disclosure is in sequencing-by-synthesis reactions, the utility of the such nucleotides is not limited to such methods. In fact, the labeled nucleotides described herein may be used advantageously in any sequencing methodology which requires detection of fluorescent labels attached to nucleotides incorporated into a polynucleotide.

In particular, nucleotides labeled with dye compounds of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses nucleotides labeled with dye compounds which are dideoxynucleotides lacking hydroxyl groups at both of the 3' and 2' positions, such modified dideoxynucleotides being suitable for use in Sanger type sequencing methods and the like.

Nucleotides labeled with dye compounds of the present disclosure incorporating 3' blocking groups, it will be recognized, may also be of utility in Sanger methods and related protocols since the same effect achieved by using dideoxy nucleotides may be achieved by using nucleotides having 3' OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

Alternatively, the sequencing methods described herein may also be carried out using unlabeled nucleotides and affinity reagents containing a fluorescent dye described herein. For example, one, two, three or each of the four different types of nucleotides (e.g., dATP, dCTP, dGTP and dTTP or dUTP) in the incorporation mixture of step (a) may be unlabeled. Each of the four types of nucleotides (e.g., dNTPs) has a 3' hydroxy blocking group to ensure that only a single base can be added by a polymerase to the 3' end of the primer polynucleotide. After incorporation of an unlabeled nucleotide in step (b), the remaining unincorporated nucleotides are washed away. An affinity reagent is then introduced that specifically recognizes and binds to the incorporated dNTP to provide a labeled extension product comprising the incorporated dNTP. Uses of unlabeled nucleotides and affinity reagents in sequencing by synthesis have been disclosed in WO 2018/129214 and WO 2020/097607. A modified sequencing method of the present disclosure using unlabeled nucleotides may include the following steps:

(a') contacting a primer polynucleotide/target polynucleotide complex with one or more unlabeled nucleotides (e.g., dATP, dCTP, dGTP, and dTTP or dUTP), wherein the primer polynucleotide is complementary to at least a portion of the target polynucleotide;

(b') incorporating a nucleotide into the primer polynucleotide to produce an extended primer polynucleotide;

(c') contacting the extended primer polynucleotide with a set of affinity reagents under conditions wherein one affinity reagent binds specifically to the incorporated unlabeled nucleotide to provide a labeled extended primer polynucleotide/target polynucleotide complex;

(d') performing one or more fluorescent measurements of the labeled extended primer polynucleotide/target polynucleotide complex to determine the identity of the incorporated nucleotide.

In some embodiments of the modified sequencing method described herein, each of the unlabeled nucleotides in the incorporation mixture contains a 3' hydroxy blocking group. In further embodiments, the 3' hydroxy blocking group of the incorporated nucleotide is removed prior to the next incorporation cycle. In still further embodiments, the method further comprises removing the affinity reagent from the incorporated nucleotide. In still further embodiments, the 3' hydroxy blocking group and the affinity reagent are removed in the same reaction. In some embodiments, the set of affinity reagents may comprise a first affinity reagent that binds specifically to the first type of nucleotide, a second affinity reagent that binds specifically to the second type of nucleotide, and a third affinity reagent that binds specifically to the third type of nucleotide. In some further embodiments, each of the first, second and the third affinity reagents comprises one or more detectable labels that are spectrally distinguishable. In some embodiments, the affinity reagents may include protein tags, antibodies (including but not limited to binding fragments of antibodies, single chain antibodies, bispecific antibodies, and the like), aptamers, knottins, affimers, or any other known agent that binds an incorporated nucleotide with a suitable specificity and affinity. In one embodiment, at least one affinity reagent is an antibody or a protein tag. In another embodiment, at least one of the first type, the second type and the third type of affinity reagents is an antibody or a protein tag comprising one or more detectable labels (e.g., multiple copies of the same detectable label), wherein the detectable label is or comprises a bis-boron dye moiety described herein.

EXAMPLES

Additional embodiments are disclosed in further detail in the following examples, which are not in any way intended to limit the scope of the claims.

Example 1. Synthesis of Compounds of Formula (I)

Synthesis of Starting Material SM1:

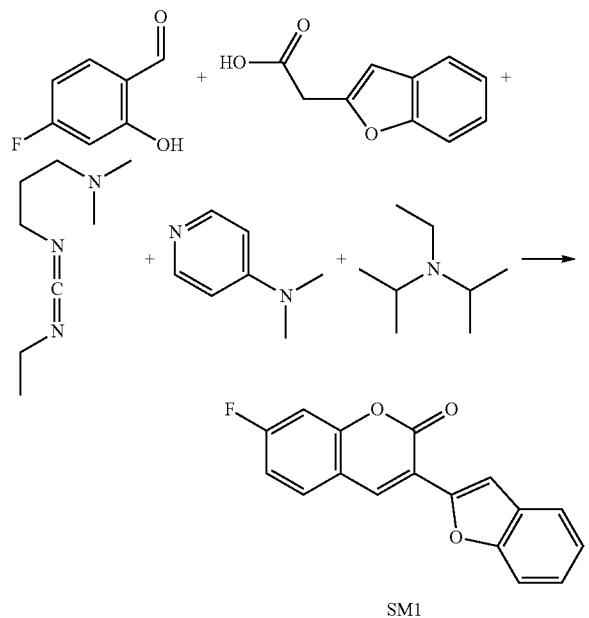

(Benzofynan-2-yl)acetic acid (0.75 g) was mixed with 4-fluoro-2-hydroxybenzaldehyde (1.04 g) in dichloromethane (20 mL). N-(3-dimethylaminopropyl)-N'-ethyl carbodiimide hydrochloride (1.1 g), 4-(dimethylamino)pyridine (980 mg) and diisopropylethylamine (1.38 g) were added. The reaction mixture was stirred at RT. After 1 h, the mixture was concentrated in vacuum. The residue was suspended in acetonitrile, precipitate was collected by vacuum filtration, washed with acetonitrile and dried to give the product as a yellow solid. Yield 780 mg (52%). $^{19}$F NMR (376 MHz, DMSO) δ −105.29.

Synthesis of Starting Material SM2:

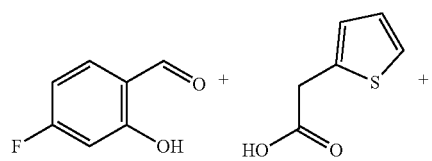

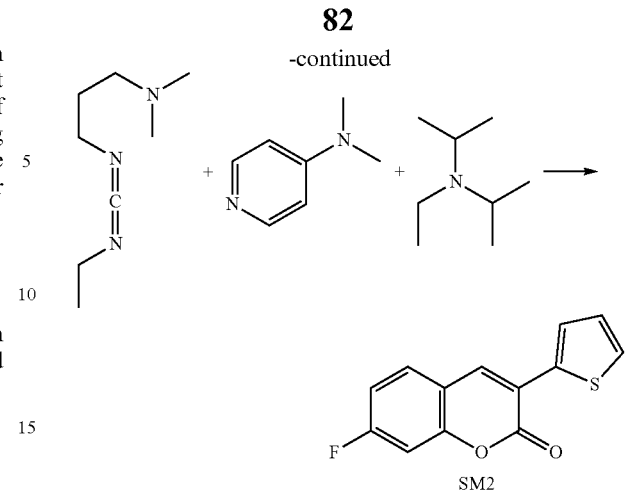

A mixture of (thiophene-2-yl)acetic acid (0.84 g, 5.9 mmol), 4-fluoro-2-hydroxybenzaldehyde (0.75 g, 5.35 mmol), N-(3-dimethylaminopropyl)-N'-ethylcarbodiimide hydrochloride (1.23 g, 6.4 mmol), 4-(dimethylamino)pyridine (981 mg, 8 mmol) and ethyldiisopropylamine (1.38 g, 11 mmol) in dichloromethene (20 mL) was heated with stirring at 50° C. Yellow precipitate was formed in about 5 min. Strong fluorescence under UV. After 1 h, the mixture was concentrated in vacuum. The residue was suspended in acetonitrile, precipitate was collected by vacuum filtration, washed with acetonitrile and dried. Yield 1.1 g (77%).

General Synthetic Procedure (Suzuki Cross-Coupling)

An appropriate 3-halo-coumarin (1 eq) and aryl/hetaryl boronic acid or ester (1.1 eq) in mixture of dimethylformamide and water were treated with catalytic amount of PdCl$_2$(PPh$_3$)$_2$ in presence of base (sodium carbonate). The reaction mixture was heated at 90° C. for 16 h and subsequently cooled to RT. For the product isolation this reaction mixture was diluted with water, acidified with HCl (1M) and the product extracted with ethyl acetate. Combined organic fractions were washed with brine, dried over anhydrous sodium sulfate and concentrated in vacuo. The crude usually semi-solid residue was triturated with organic solvent (for example DCM) and the produce isolated by filtering.

Compound: I-2: 2-(7-(Diethylamino)-4-methyl-2-oxo-2H-chromen-3-yl)furan-4-carboxylic acid

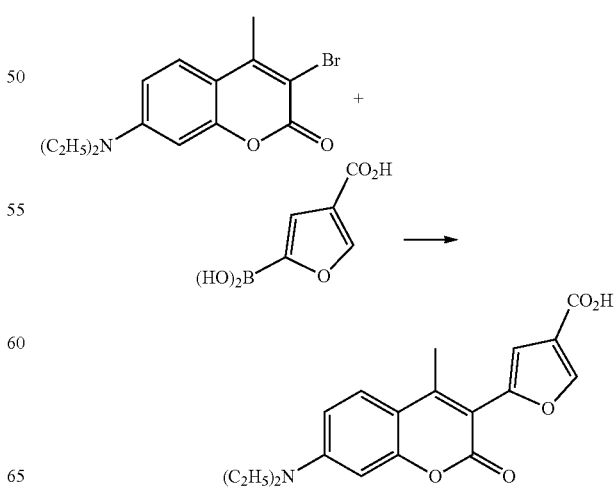

3-Bromo-7-diethylamino-4-methyl-coumarin (50 mg, 0.22 mmol) and 2-boranofuran-4-carboxylic acid (51 mg, 0.22 mmol) in dimethylformamide (1.6 mL) and water (0.4 mL) were treated with 1,1'-bis(diphenylphosphino)ferrocene]dichloropalladium (II), complex with dichloromethane ($PdCl_2$(dppf).DCM, 2.6 mg, 3.2 μmol, 1.5 mol %) and $Na_2CO_3$ (59 mg, 0.56 mmol). The reaction mixture was heated at 90° C. for 6 h and subsequently cooled to RT. The mixture was diluted with $H_2O$, acidified with HCl (1M) and the product extracted with ethyl acetate. The combined organics were washed with brine, dried ($Na_2SO_4$) and concentrated in vacuo. Crude residue purified by preparative HPLC. Yield 7%. LC-MS (−): m/z 340 (M−1)⁻; (+): 342 (M+1)⁺, 683 (2M+1)⁺. Absorption maximum in EtOH 395 nm. Emission maximum in EtOH 485 nm (excitation @ 400 nm).

Compound I-3: 5-(7-(Diethylamino)-2-oxo-2H-chromen-3-yl)furan-2-carboxylic acid

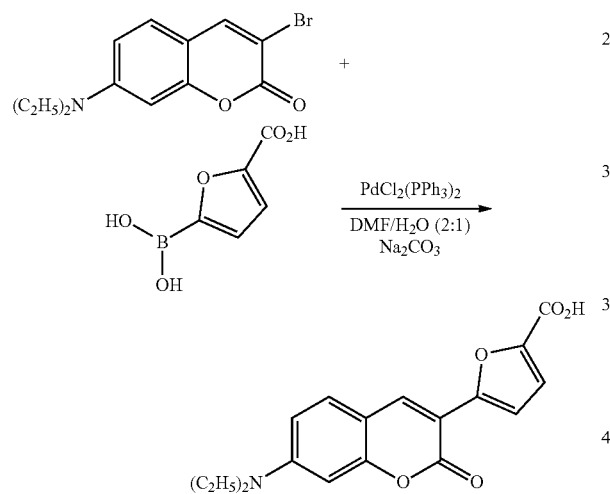

Compound I-3 was prepared according to the general coupling procedure described above. Yield 46%. LC-MS (−) m/z 326 (M−1)⁻. Compound I-1 was prepared according to similar procedure as Compound I-3 using 2-boronofuran-4-carboxylic acid instead.

Compound I-4: 2-(7-(Diethylamino)-2-oxo-2H-chromen-3-yl)benzofuran-6-carboxylic acid

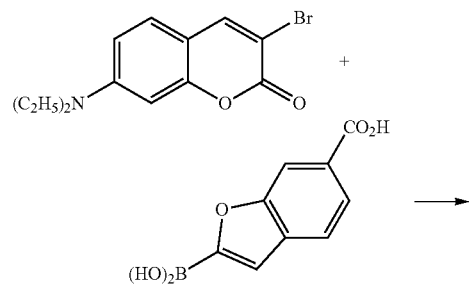

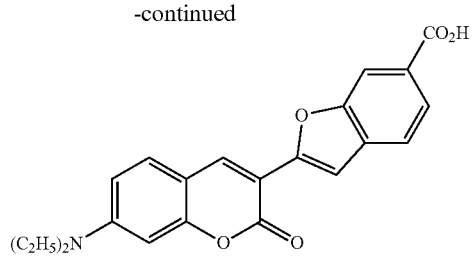

3-Bromo-7-diethylamino coumarin (135 mg, 0.40 mmol) and 2-boronobenzofuran-6-carboxylic acid (113 mg, 0.55 mmol) in dimethylformamide (10 mL) and water (5 mL) were treated with $PdCl_2(PPh_3)_2$ (11 mg, 16 μmol, 5 mol %) and $Na_2CO_3$ (68 mg, 0.64 mmol). The reaction mixture was heated at 90° C. for 16 h and subsequently cooled to RT. The mixture was diluted with $H_2O$, acidified with HCl (1M) and extracted with ethyl acetate. The combined organics were washed with brine, dried ($Na_2SO_4$) and concentrated in vacuo. The crude residue was triturated in dichloromethane and the produce isolated by filtering under vacuum. Yield 76 mg (50%). LC-MS (−) m/z 376 (M−1)⁻.

Compound I-5: 2-(7-(Diethylamino)-2-oxo-2H-chromen-3-yl)benzofuran-5-carboxylic acid

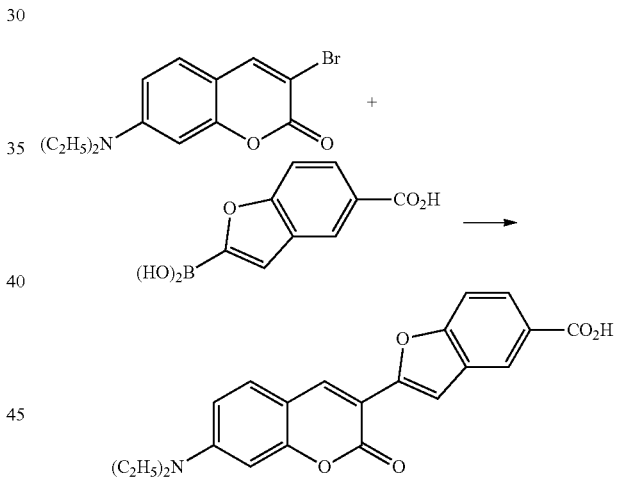

Compound I-5 was prepared according to the general coupling procedure described above. Yield (36%). LC-MS (−): m/z 376 (M−1)⁻; (+): 378 (M+1)⁺, 755 (2M+1)⁺.

Compound I-6: 2-(7-(Diethylamino)-2-oxo-2H-chromen-3-yl)thiophen-5-carboxylic acid

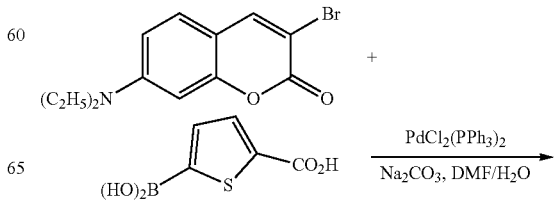

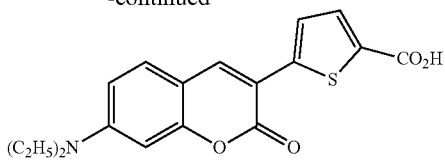

Compound I-6 was prepared according to the general coupling procedure described above. Yield 78%. LC-MS (−): m/z 342 (M−1)⁻; (+): 344 (M+1)⁺, 687 (2M+1)⁺. Absorption maximum in EtOH 432 nm. Emission maximum in EtOH 506 nm (excitation @ 450 nm).

Compound I-7: 2-(7-(Diethylamino)-2-oxo-2H-chromen-3-yl)-1-methyl-1H-indol-5-carboxylic acid

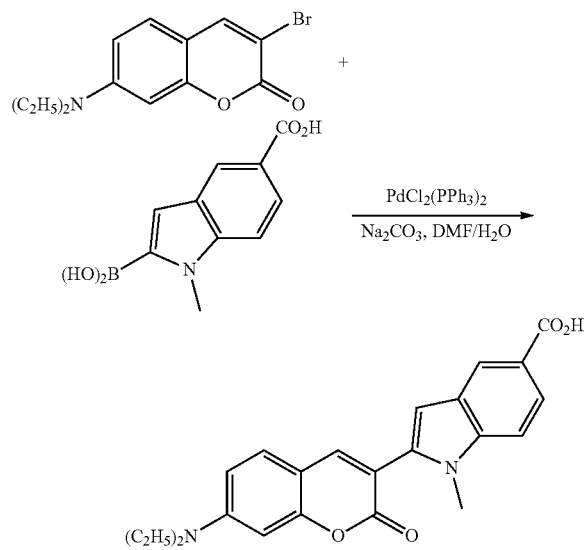

Compound I-7 was prepared according to the general coupling procedure described above. Yield 80%. LC-MS (−): m/z 389 (M−1)⁻; (+): 391 (M+1)⁺. Absorption maximum in EtOH 407 nm.

Compound I-8a: 3-(N-(3-(Cycloocta-1,3,5,7-tetraene-1-carboxamido)propyl)-2-(7-fluoro-2-oxo-2H-chromen-3-yl)benzofuran-6-carboxamido)propane-1-sulfonic acid

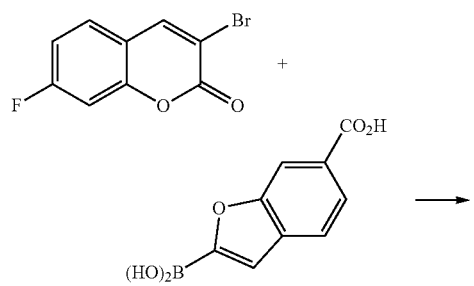

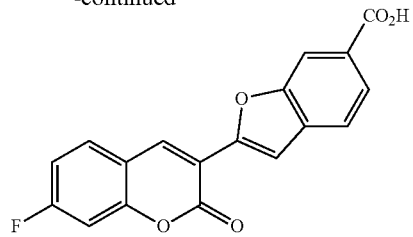

2-(7-Fluoro-2-oxo-2H-chromen-3-yl)benzofuran-6-carboxylic acid was prepared in according with general coupling procedure from 3-bromo-7-fluoro-coumarin and 2-boronobenzofuran-6-carboxylic acid in dimethylformamide-water mixture (2:1). After solvents evaporation the crude residue was triturated with diisopropylether and the produce isolated by filtering. Yield 57%. LC-MS (−) m/z 323 (M−1)⁻.

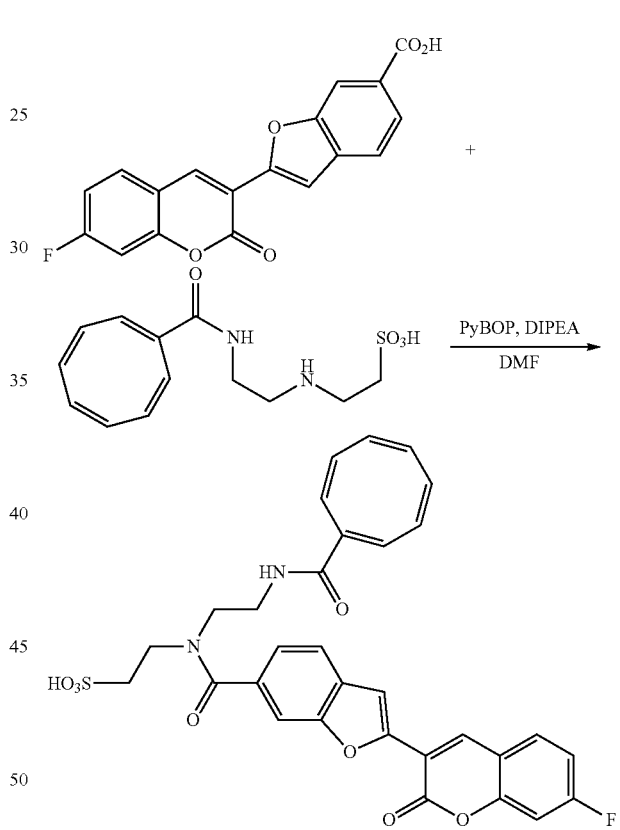

2-(7-Fluoro-2-oxo-2H-chromen-3-yl)benzofuran-6-carboxylic acid (100 mg, 0.31 mmol) in dimethylacetamide (5 mL) treated with benzotriazole-1-yl-oxy-tris-pyrrolidino-phosphonium hexafluorophosphate (PyBOP, 193 mg, 0.37 mmol) and diisopropylethylamine (DIPEA, 1 mL). The reaction mixture was stirred at RT for 10 min and then 3-((3-(cycloocta-1,3,5,7-tetraene-1-carboxamido)propyl) amino)propane-1-sulfonic acid (COT-S, 110 mg, 0.37 mmol) in dimethylacetamide (3 mL) added. The reaction mixture was stirred for 18 h and acidified with 2 M HCl. The resulting precipitate was isolated by filtration and washed with acetonitrile then purified by preparative HPLC to afford 2-(N-(2-(Cycloocta-1,3,5,7-tetraene-1-carboxamido)ethyl)-2-(7-fluoro-2-oxo-2H-chromen-3-yl)benzofuran-6-carboxamido)ethane-1-sulfonic acid (Compound I-8b). Yield: 33 mg (18%). LC-MS (−) m/z 603 (M−1)⁻.

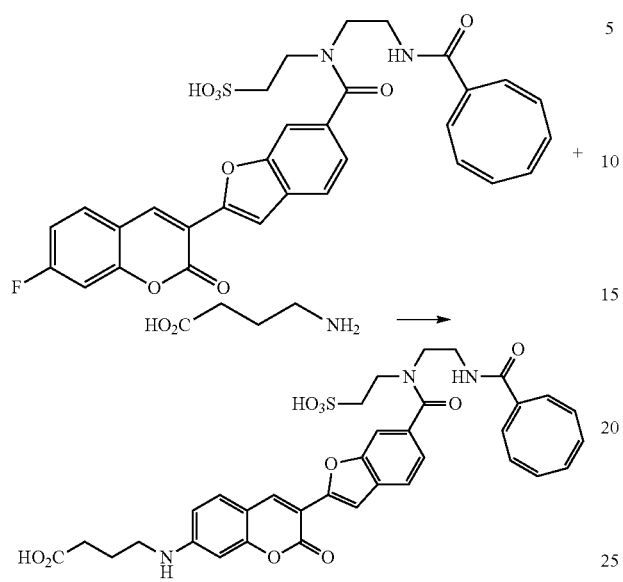

Compound I-8b (33 mg, 55 μmol), triethylamine (15 μL, 110 μmol) and 4-aminobutanoic acid (11 mg, 110 μmol). in DMSO (3 mL) were stirred at 80° C. for 2 h, and then additional amount of 4-aminobutanoic acid (1 eq) and triethylamine (2 eq) were added. The reaction mixture heated at 110° C. for 24 h. Cooled to RT and diluted with acetonitrile and TEAB (0.1M). The final product was isolated and purified by preparative HPLC. Yield 42%. LC-MS (−) m/z 686 (M−1)⁻, 343(M−1)²⁻. Absorption maximum in EtOH 426 nm. Emission maximum in EtOH 482 nm (excitation @ 430 nm).

Compound I-9: 1-(3-(Benzofuran-2-yl)-2-oxo-2H-chromen-7-yl)piperidine-4-carboxylic acid

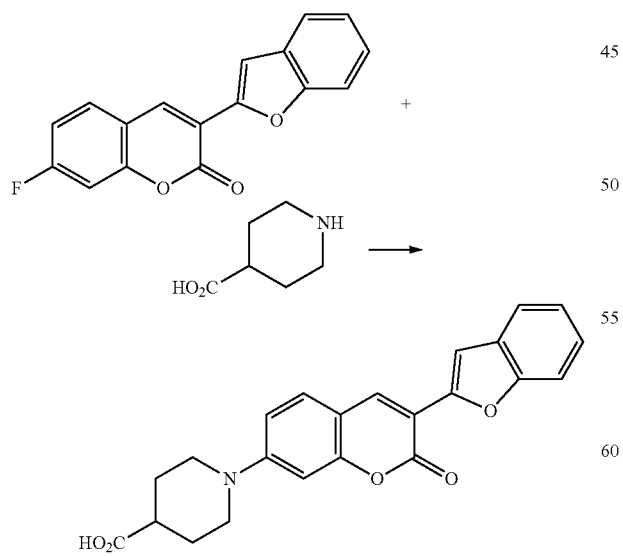

3-(Benzofuran-2-yl)-7-fluoro-2H-chromen-2-one (280 mg), diisopropylethylamine (0.1 mL) and isonipecotic acid (129 mg) were stirred in DMSO (2 mL) at 120° C. for 4 h. Then the reaction mixture was diluted with acetonitrile (3 mL) and water (2 mL). Solid precipitate was filtered off, washed with water. Yield 170 mg (~44%). ¹H NMR (400 MHz, DMSO) δ 8.49 (s, 1H), 7.74-7.68 (m, 2H), 7.60 (dd, J=8.1, 1.0 Hz, 1H), 7.50 (d, J=1.0 Hz, 1H), 7.34 (ddd, J=8.3, 7.2, 1.4 Hz, 1H), 7.27 (td, J=7.5, 1.1 Hz, 1H), 7.06 (dd, J=9.0, 2.5 Hz, 1H), 6.91 (d, J=2.4 Hz, 1H), 4.02-3.88 (m, 2H), 3.07 (td, J=13.4, 12.7, 3.1 Hz, 2H), 1.95-1.84 (m, 2H), 1.67-1.54 (m, 2H).

Compound I-10: 1-[2-Oxo-3-(thiophen-2-yl)-2H-chromen-7-yl)piperidine-4-carboxylic acid

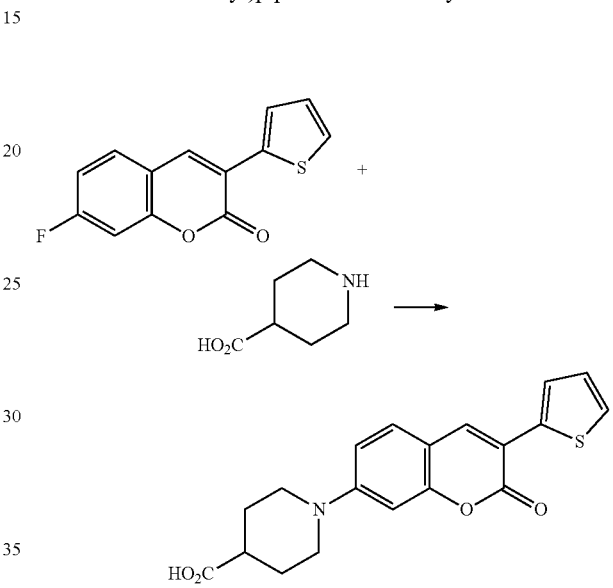

3-(Thiophen-2-yl)-7-fluoro-2H-chromen-2-one (280 mg), diisopropylethylamine (0.1 mL) and isonipecotic acid (147 mg) were stirred in DMSO (2 mL) at 110° C. for 6 h. Then the reaction mixture was diluted with acetonitrile (3 mL) and water (2 mL). Solid precipitate was filtered off, washed with water. Yield 135 mg (~33%). ¹H NMR (400 MHz, DMSO) δ 12.26 (s, 1H), 8.42 (s, 1H), 7.73 (dd, J=3.7, 1.2 Hz, 1H), 7.58 (d, J=0.9 Hz, 1H), 7.58-7.55 (m, 1H), 7.15 (dd, J=5.1, 3.7 Hz, 1H), 7.04 (dd, J=8.9, 2.5 Hz, 1H), 6.90 (d, J=2.4 Hz, 1H), 3.97-3.87 (m, 2H), 3.04 (ddd, J=14.0, 11.6, 3.0 Hz, 2H), 1.90 (dd, J=13.8, 3.4 Hz, 2H), 1.68-1.52 (m, 3H).

Compound I-11: N-[2-Oxo-3-(thiophen-2-yl)-2H-chromen-7-yl]-N-(2-sulfoethyl)glycine

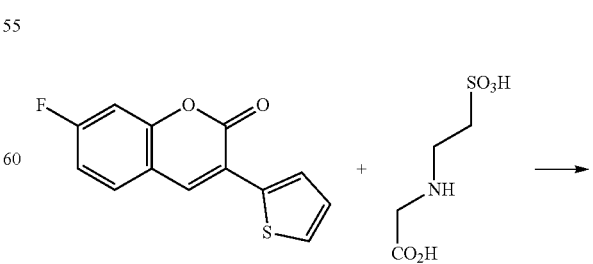

-continued

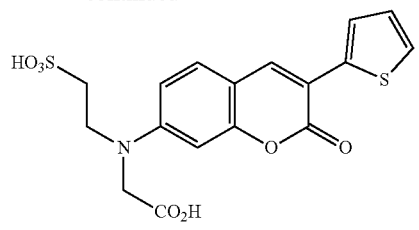

Compound I-11 was prepared following similar procedure described herein from 3-(thiophen-2-yl)-7-fluoro-2H-chromen-2-one and N-(2-sulfoethyl)glycine. Yield 28%.

Compound I-12: 1-[3-(3-Sulfo-benzofuran-2-yl)-2-oxo-2H-chromen-7-yl]piperidine-4-carboxylic acid

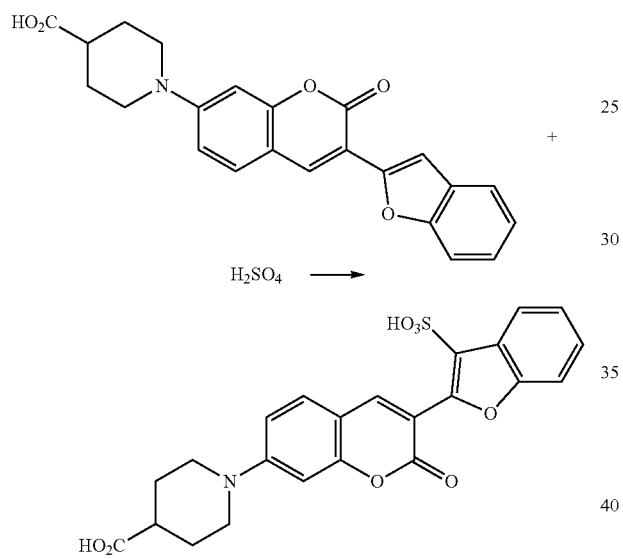

Compound I-9 (390 mg) was added to chilled sulfuric acid (1 g) and was stirred at RT for 3 h. The reaction mixture was triturated was anhydrous diethyl ether and. Crystalline product was collected by filtration and washed with ethanol and ether mixture (1:1, 5 mL). Yield 290 mg (62%). LC-MS m/z (−) 468 (M−1)⁻.

Compound I-13: 1-[3-(5-Sulfo-thiopen-2-yl)-2-oxo-2H-chromen-7-yl]piperidine-4-carboxylic acid

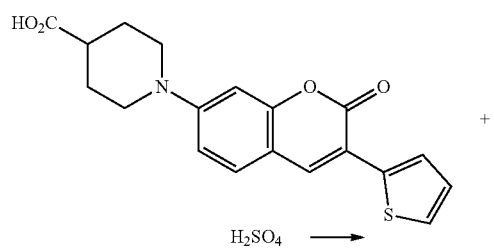

-continued

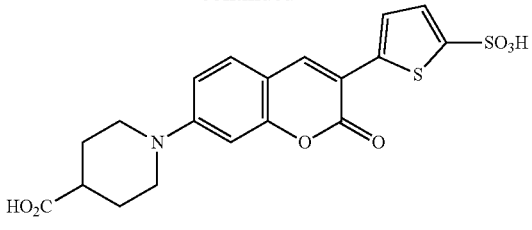

Compound I-10 (710 mg) was added to chilled sulfuric acid (1 g) and was stirred at RT for 1 h and additionally at 50° C. for 1 h. The reaction mixture was triturated was anhydrous diethyl ether and acetonitrile. Product was collected by filtration and washed with ethanol and ether mixture (1:1, 2×5 mL). Yield 720 mg (83%). LC-MS m/z (−) 434 (M−1)⁻.

Compound I-14: 1-(3-(Benzofuran-2-yl)-2-oxo-2H-chromen-7-yl)piperidine-2-carboxylic acid

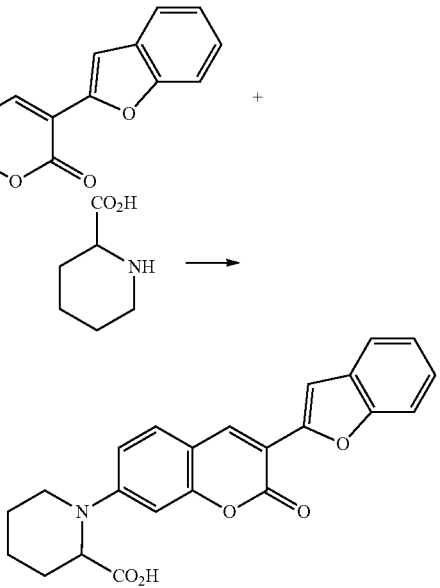

3-(Benzofuran-2-yl)-7-fluoro-2H-chromen-2-one (example I-1, 280 mg), diisopropyl ethylamine (0.1 mL) and piperidine-2-carboxylic acid (155 mg) were stirred in DMSO (2 mL) at 110° C. for 6 h. Then the reaction mixture was diluted with acetonitrile (3 mL) and water (2 mL). Solid precipitate was filtered off, washed with water. Yield 125 mg (32%).

Example 2. Comparison of Chemical Stability of Dyes of Formula (I)

Three ffCs labeled with Dye I-1, Dye I-2 and a reference Dye A respectively were kept in an incorporation buffer at 37° C. in the dark. Then, the fluorescent signal intensities were examined during 48 h and showed normalized in FIG. 1. The results demonstrate that ffC labeled with the new dyes of Formula (I) are chemically more stable than the ffC labeled with Reference Dye A.

Figure 2:
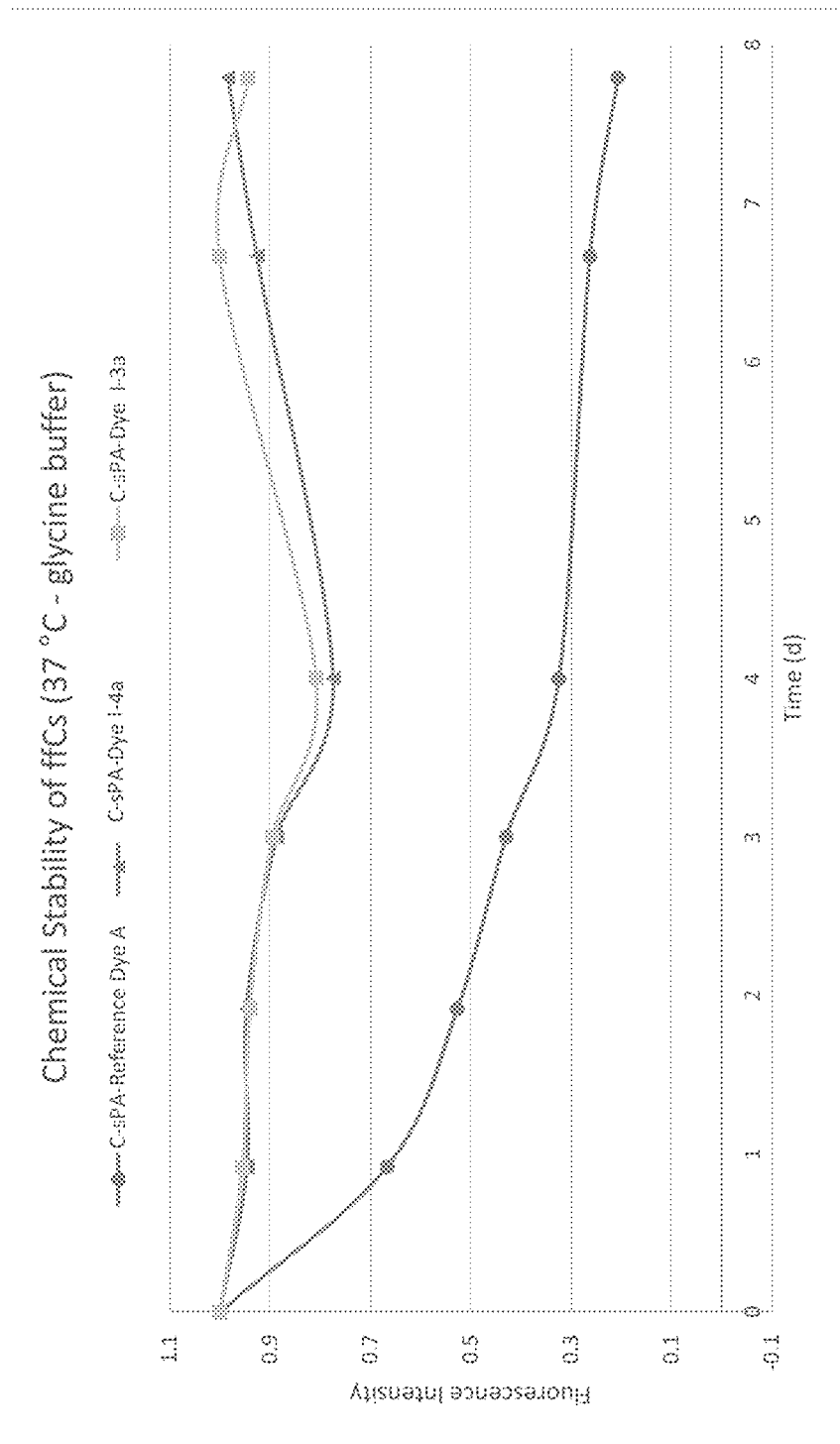
FIG. 2 is a line chart illustrating the fluorescent intensity of a fully functionalized C nucleotide (ffC) labeled with reference Dye A as compared to the same ffC labeled with Dye I-3 or Dye I-4 in a buffer solution at 37° C.

In another experiment, three ffCs labeled with Dye I-3a, I-4a, and a reference Dye A were kept in a glycine buffer at 37° C. for 8 days. Then, the remaining fluorescent signal intensity were examined and showed in FIG. 2. It was observed that the fluorescent intensity decreased overtime after heating in the glycine buffer. Both Dye I-3a and Dye I-4a have demonstrated improved chemical stability than Dye A.

Furthermore, the spectral property of a labelled ffC with Dye I-8a was measured in a scan mix at RT (excitation at 460 nm). The excitation/emission spectral (Ex/Em) is 434/494 nm.

The structures of the ffCs labeled with the compound of Formula (I) and Reference Dye A are shown below:

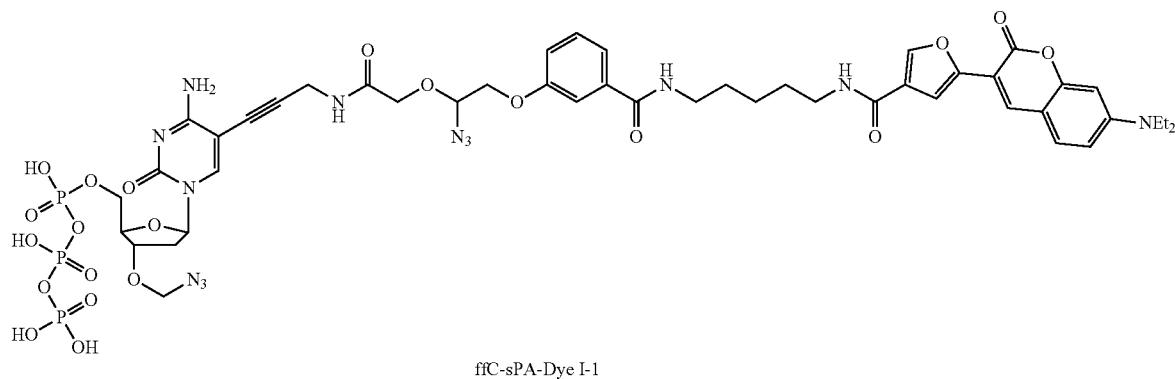

ffC-sPA-Dye I-1

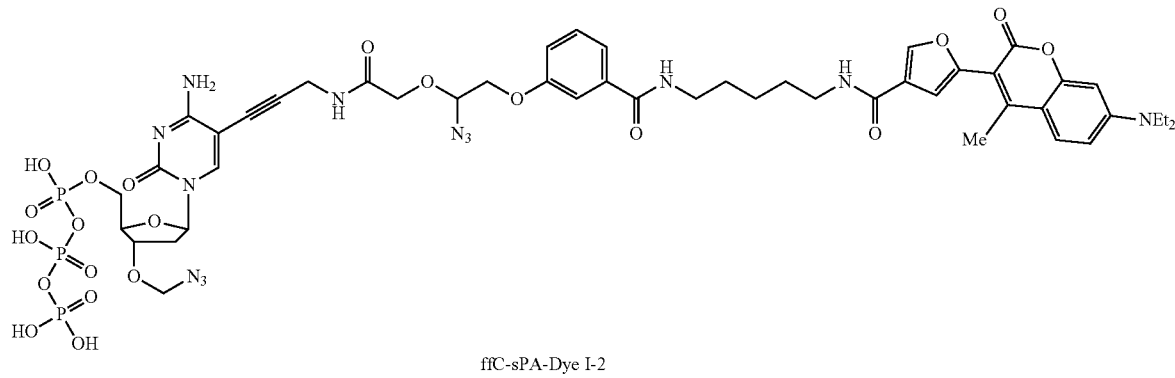

ffC-sPA-Dye I-2

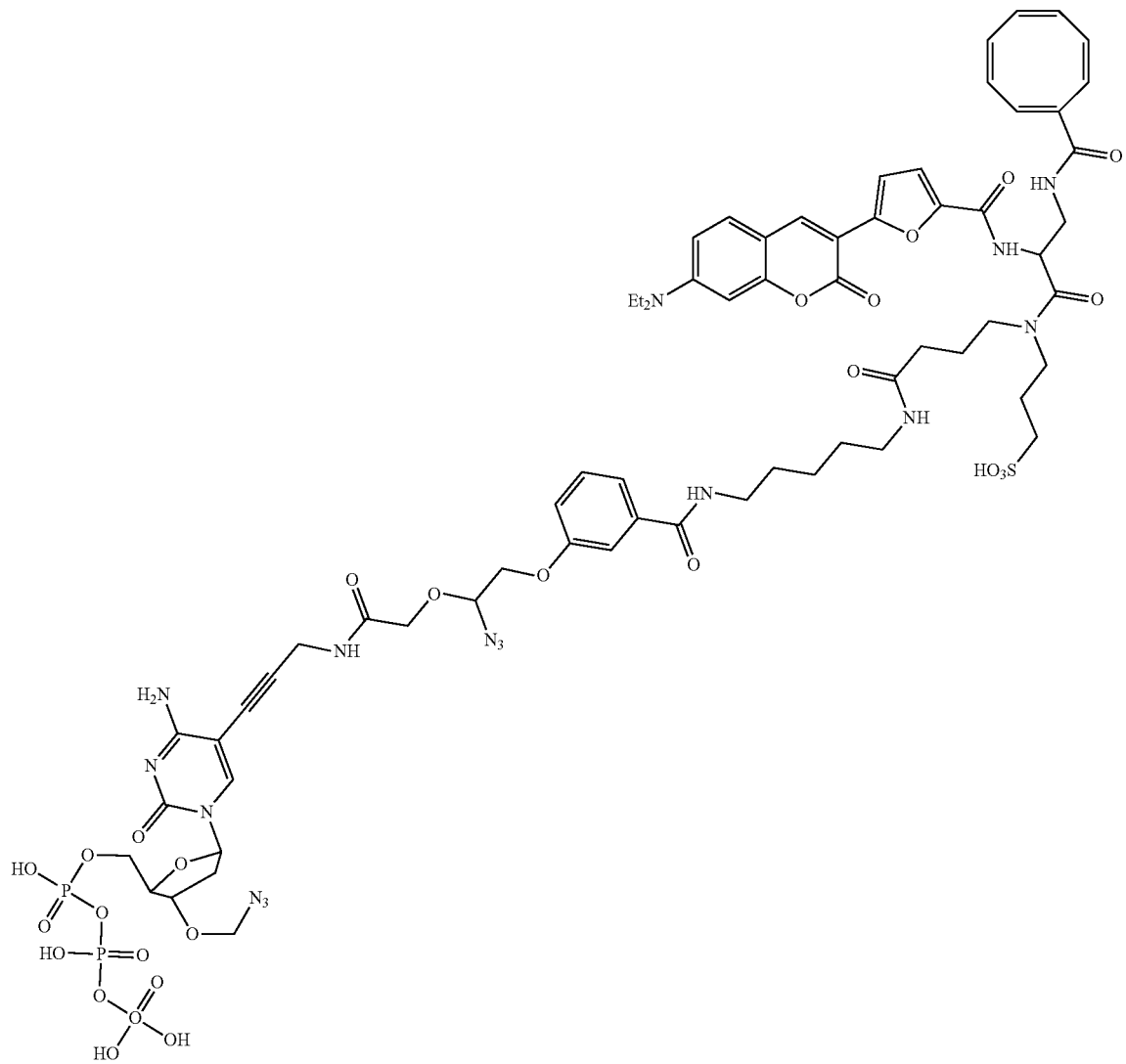
ffC-sPA-Dye I-3a

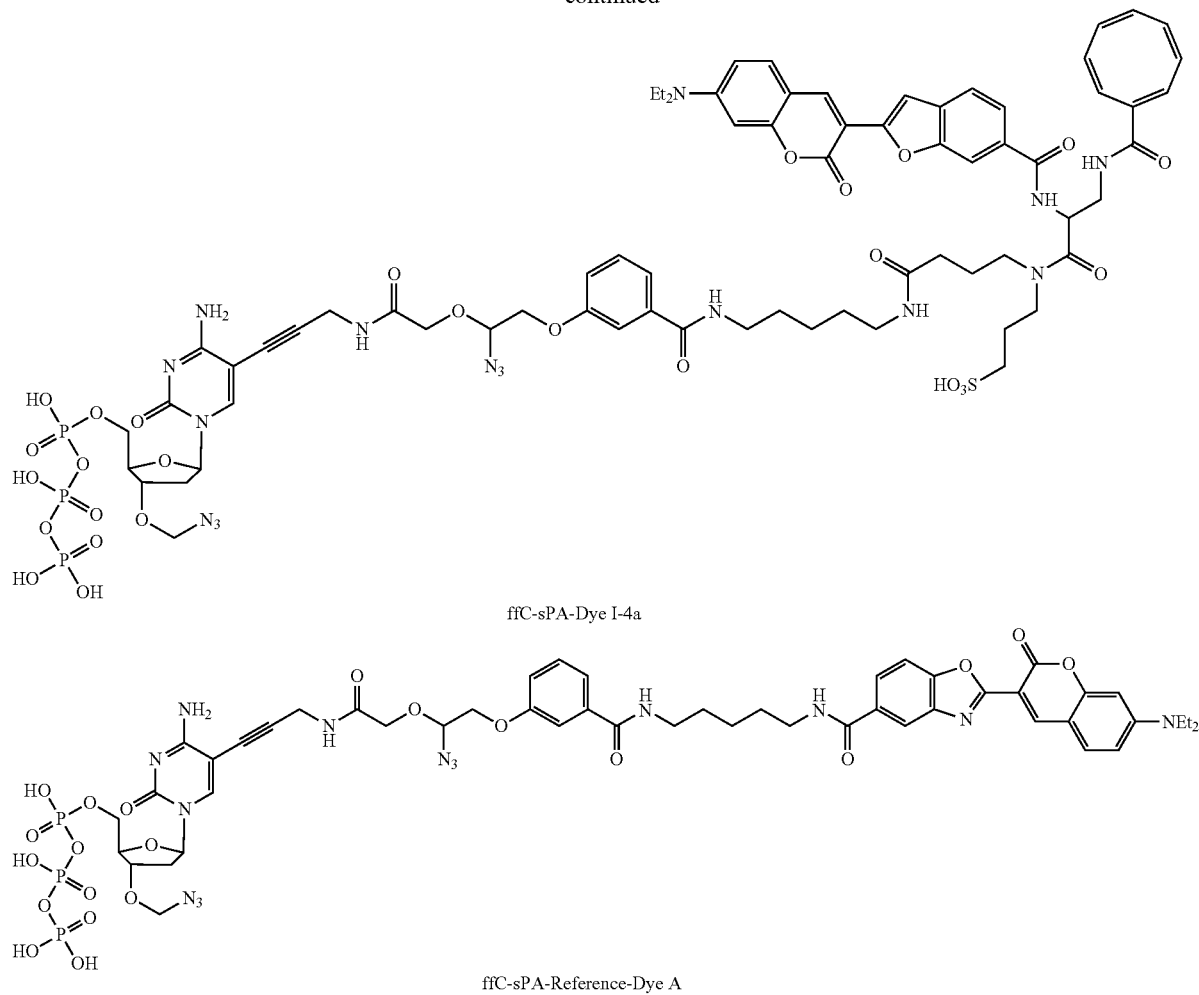
ffC-sPA-Dye I-4a
ffC-sPA-Reference-Dye A
Example 3. Synthesis of Compounds of Formula (II) or (II')
General Synthetic Scheme
Compounds of Formula (II) may be prepared by the following general reaction schemes (where Y is O or NH):
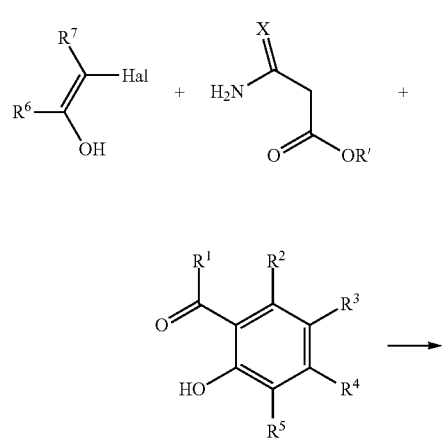
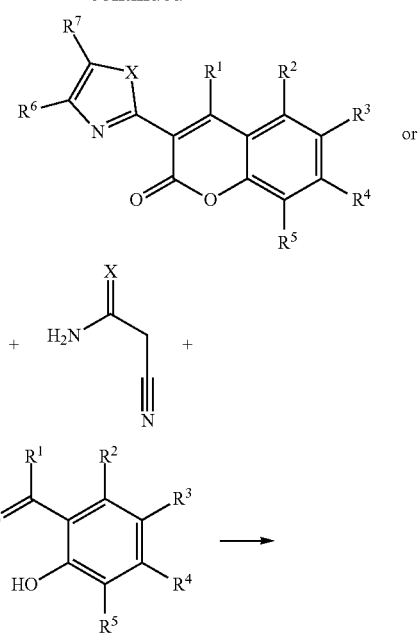

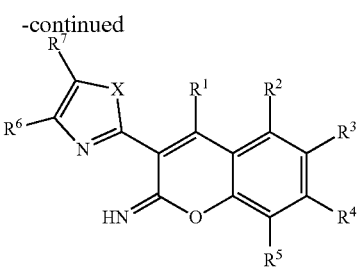

Compound II-51a: Ethyl 2-(2-(7-fluoro-2-oxo-2H-chromen-3-yl)thiazol-4-yl)acetate

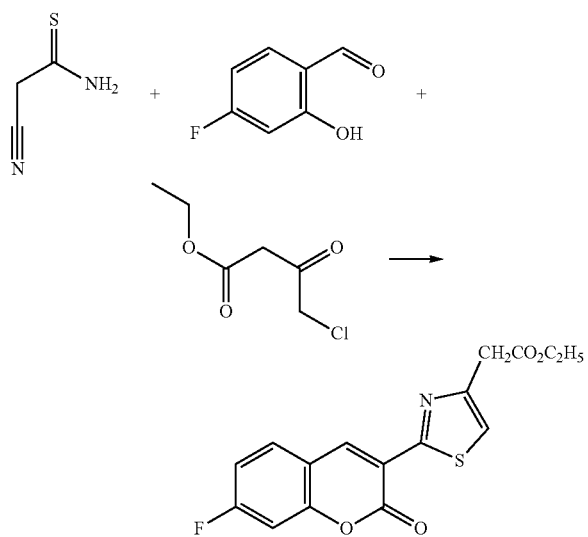

Procedure A: 2-Cyanothioacetamide (5 g, 50 mmol, 1 eq), 4-fluorosalisylic aldehyde (7.7 g, 55 mmol, 1.1 eq), ethyl 4-chloro-acetoacetate (9.9 g, 60 mmol, 1.2 eq) in ethanol (100 mL) were heated at ~70° C. for 2 h. Tetrabutylammonium bromide (NBu₄Br, 0.5 g) was added ant the reaction mixture was heated at 90° C. for 1.5 h and was left stirring overnight at RT. Then precipitate was filtered off, washed with ethanol (~5 mL) and water (2×15 mL). Crystallization from EtOH. Yield 11 g (~67%).

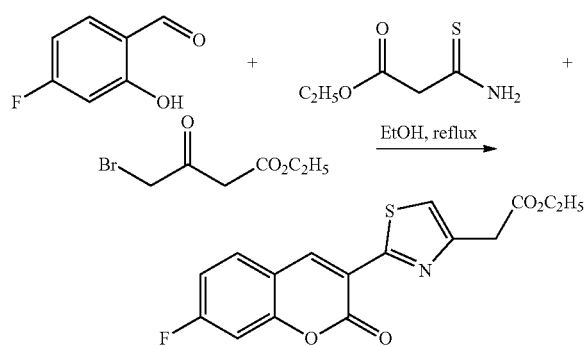

Procedure B: 4-Fluoro-2-hydroxybenzaldehyde (1.5 g, 1.1 eq), ethyl 3-amino-3-thioxopropanoate (1.5 g, 1.0 eq) and ethyl 4-bromoacetoacetate (2.3 g, 1.1 eq) in ethanol (5 mL) were refluxed for 3 h. Reaction mixture was left at RT overnight. Precipitate isolated by filtration, washed with small volume of ethanol, suspended in water (~15 mL) and sodium bicarbonate (1.1 eq) added, mixture stirred for 10 min, precipitate filtered off. Washed with water. Target compound isolated as of white solid.

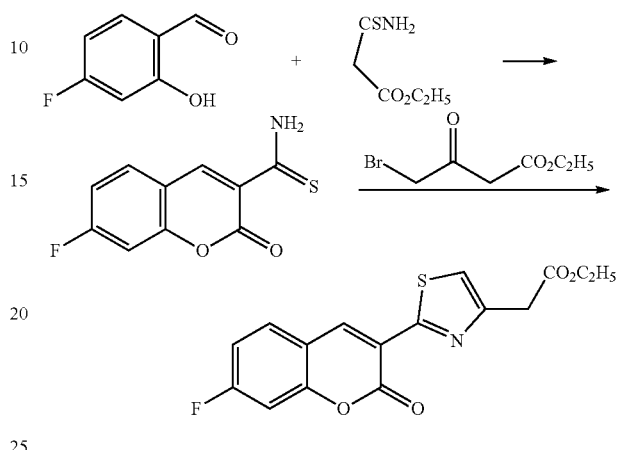

4-Fluoro-2-hydroxybenzaldehyde (5 g, 1 eq) and ethyl 3-amino-3-thioxopropanoate (5.8 g, 1.1 eq) were dissolved in EtOH (50 mL). Reaction mixture was stirred 1 h at RT and then refluxed for 3 h. Reaction mixture was left stirred at RT overnight. Precipitate isolated by filtration, washed with small volume of ethanol. Yield 6.6 g (83%).

7-Fluoro-2-oxo-2H-chromene-3-carbothioamide (2 g, 1.0 eq) and ethyl 4-bromoacetoacetate (1.87 g, 1 eq) in ethanol (5 mL) were refluxed for 3 h. Reaction mixture was left at RT overnight. Precipitate isolated by filtration, washed with small volume of ethanol, suspended in water (~15 mL) and sodium bicarbonate (1 g) was added, mixture stirred for 10 min, precipitate filtered off. Washed with water. Target compound isolated as off white solid.

Compound II-51d (ethyl 2-(2-(7-bromo-2-oxo-2H-chromen-3-yl)thiazol-4-yl)acetate) was prepared following similar procedure described above in the preparation of Compound II-51a. Yield:~80%.

Compound II-60a: Ethyl 2-(2-(6-fluoro-2-oxo-2H-chromen-3-yl)thiazol-4-yl)acetate

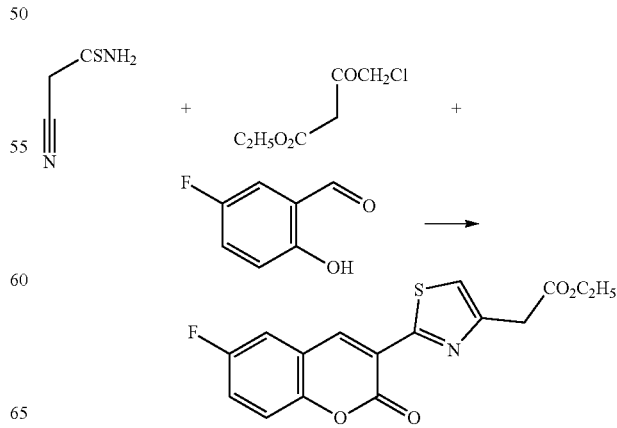

Compound II-60a was Prepared similarly to procedure A described in the preparation of Compound II-51a. Yield: ~50%.

Compound II-54a: Ethyl 2-(7-fluoro-2-oxo-2H-chromen-3-yl)-4-methylthiazole-5-carboxylate

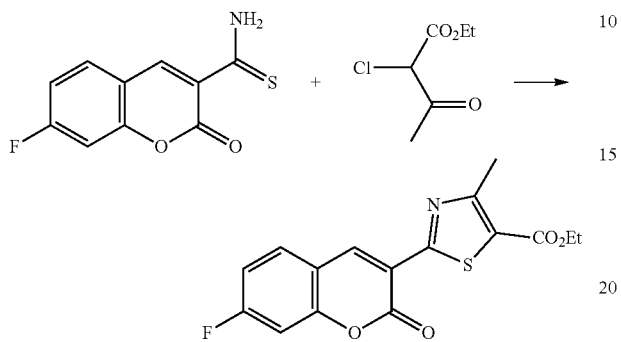

Mixture of 7-fluoro-3-thiocarbamoylcoumarin (450 mg, 1 eq) and ethyl 2-chloroacetoacetate (365 mg, 1.1 eq) in dimethylformamide (3 mL) was stirred at 90° C. for 2 h and left overnight at RT. Then reaction mixture was diluted with water (5 mL) and neutralized with sodium bicarbonate. Precipitate was filtered off and crystallised from ethanol. Yield ~81%.

Compound II-51: (2-(7-Fluoro-2-oxo-2H-chromen-3-yl)thiazol-4-yl)acetic acid

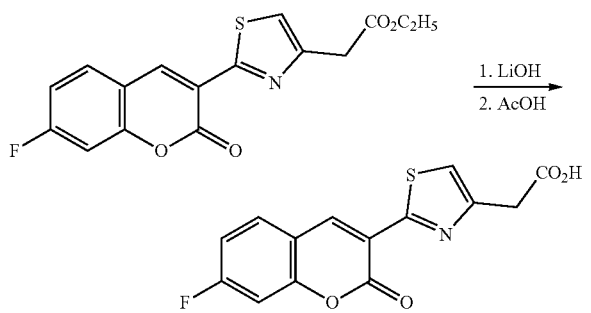

7-Fluoro-3-[(4-ethoxycarbonylmethyl)-2-thiazolyl]-2H-benzopyranone-2 (1 g, 3 mmol, 1 eq) was suspended in water (5 mL), ethanol (0.5 mL) and lithium hydroxide (0.36 g, 15 mmol, 5 eq) were added. Reaction mixture was stirred at 35° C. for about 3 hours. Nearly clear solution was filtered, filtrate acidified with acetic acid (1.5 mL) and was left overnight at RT. Then the product was filtered off, washed with cold water (2×1 0.5 mL) and dried in air. Yield 0.76 g (83%). $^1$H NMR (400 MHz, DMSO-$d_6$) δ 8.97 (s, 1H), 8.14 (dd, J=8.8, 6.4 Hz, 1H), 7.66 (s, 1H), 7.53 (dd, J=9.7, 2.5 Hz, 1H), 7.35 (td, J=8.8, 2.5 Hz, 1H), 3.83 (s, 2H). $^{19}$F NMR (376 MHz, DMSO) δ −104.37.

2-(2-(7-Bromo-2-oxo-2H-chromen-3-yl) thiazol-4-yl) acetic acid (Compound II-51c) was prepared from the corresponding ethyl ester Compound II-51d following the similar procedure described in the preparation of Compound II-51. Yield ~75%.

(2-(6-Fluoro-2-oxo-2H-chromen-3-yl)thiazol-4-yl)acetic acid (Compound II-60) was prepared from the corresponding ethyl ester Compound II-60a following the similar procedure described in the preparation of Compound II-51. Yield ~83%.

(2-(7-Fluoro-2-oxo-2H-chromen-3-yl)-4-methylthiazole-5-carboxylic acid (Compound II-54) was prepared from the corresponding ethyl ester Compound II-54a following the similar procedure described in the preparation of Compound II-51 in water-DMSO mixture at 50° C. Yield ~80%.

Compound II-52: (2-(7-Fluoro-2-oxo-2H-chromen-3-yl)thiazole-4-carboxylic acid

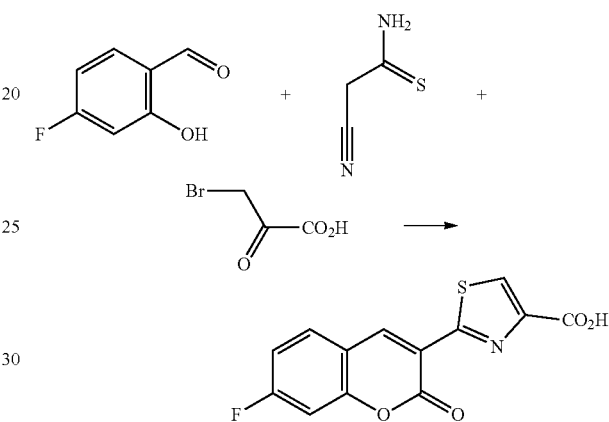

This compound was prepared following similar procedure described above in the preparation of II-51 in ethanol at about 80° C. for 1 h. Precipitate was filtered off. Then imino derivatives was hydrolyzed by stirred with water for 1 h. May contain ethyl ester as by-product which may be removed by re-precipitation from NaHCO$_3$— or Na$_2$CO$_3$ solution with acetic acid after filtration. Yield ~74%. LC-MS: (+) m/z 292(M+1); (−) m/z 290 (M−1)$^-$, 581 (2M−1)$^-$.

Compound II-1: 2-(2-(2-oxo-7-((3-sulfopropyl)amino)-2H-chromen-3-yl)thiazol-4-yl)acetic acid

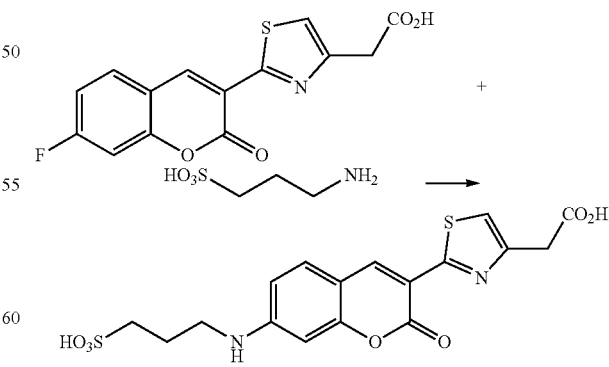

Compound II-51 (1.0 eq) and 3-aminopropanesulfonic acid (2.0 eq) in DMSO treated with DIPEA (2.0 eq) and heated at 110° C. for 18 h. Cooled to RT, diluted with 0.1M TEAB/MeCN and purified by preparative HPLC. Combined HPLC fractions were dried in vacuo. Yield ~10%. Absorption maximum 431 nm (EtOH). LC-MS: (+) m/z 425(M+1).

3-[(3-(4-(2-Ethoxycarbonylmethyl)thiazol-2-yl)-2-oxo-2H-chromen-7-yl)amino]propane-1-sulfonic acid (Compound II-1a) was prepared from reacting Compound II-51a (1.0 eq) and 3-aminopropanesulfonic acid (2.0 eq) in DMSO treated with DIPEA (2.0 eq) and heated at 100° C. for 12 h. Cooled to RT, diluted with 0.1M TEAB/MeCN and purified by preparative HPLC. Yield ~14%.

Compound II-2a: Ethyl 2-[2-(Diethylamino-2-oxo-2H-chromen-3-yl)-4-thiazolyl]acetate

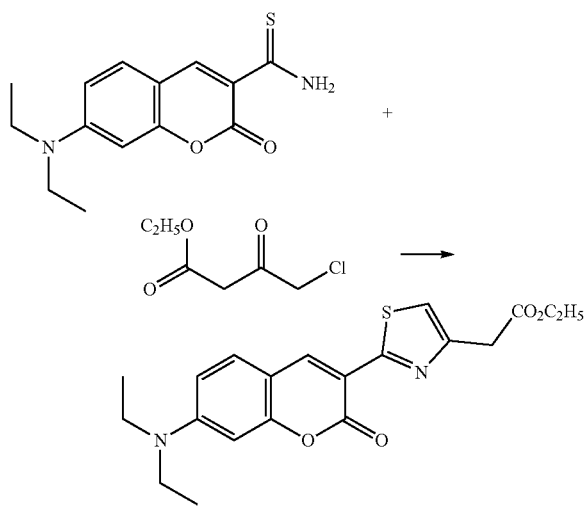

A mixture of 7-diethylamino-3-thiocarbamoyl-2H-benzopyrone-2 (276 mg, 1 eq) and ethyl 4-chloroacetoacetate (180 mg, 1.1 eq) was stirred at 100° C. in DMF (2.5 mL) for 0.5 h and left overnight at RT. Then the reaction mixture was diluted with water (2.5 mL), added sodium bicarbonate and yellow precipitate filtered off. May be crystallized from ethanol. $^1$H NMR (400 MHz, DMSO-$d_6$) δ 8.74 (s, 1H), 7.74 (d, J=9.0 Hz, 1H), 7.49 (s, 1H), 6.81 (dd, J=9.1, 2.4 Hz, 1H), 6.65 (d, J=2.4 Hz, 1H), 4.12 (q, J=7.1 Hz, 2H), 3.87 (s, 2H), 3.49 (q, J=7.0 Hz, 4H), 1.21 (t, J=7.1 Hz, 3H), 1.15 (t, J=7.0 Hz, 6H).

[2-(7-Diethylamino-2-oxo-2H-chromen-3-yl)thiazol-4-yl]acetic acid (Compound II-2) was prepared by reacting the corresponding ethyl ester II-2a with LiOH following the general procedure described in the preparation of Compound II-51. Yield ~93%. $^1$H NMR (400 MHz, DMSO-$d_6$) δ 12.43 (s, 1H), 8.75 (s, 1H), 7.74 (d, J=9.0 Hz, 1H), 7.46 (d, J=0.7 Hz, 1H), 6.81 (dd, J=9.0, 2.5 Hz, 1H), 6.65 (d, J=2.4 Hz, 1H), 3.78 (d, J=0.8 Hz, 2H), 3.49 (q, J=7.0 Hz, 4H), 1.15 (t, J=7.0 Hz, 6H).

Compound II-2b: Ethyl 2-(2-(7-Diethylamino-2-oxo-2H-chromen-3-yl)thiazol-4-yl)acetate

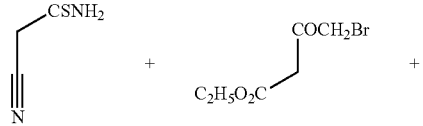

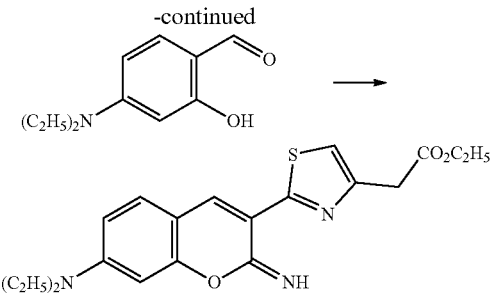

2-Cyanothioacetamide (2 g, 1 eq), p-diethylaminosalicylic aldehyde (3.86 g, 1 eq), ethyl 4-bromoacetoacetate (3.45 mL, 1 eq) in EtOH (50 mL) were stirred at RT for 0.5 h. Triethylamine (0.25 g) was added and the reaction mixture was stirred at RT again for 1.5 h and precipitated product was filtered off. Yield ~45.5%. LC-MS: (+) 386 (M+1)$^+$.

Compound II-5b: p-[2-(7-(Diethylamino)-2-imino-2H-chromen-3-yl)thiazol-4-yl]benzoic acid

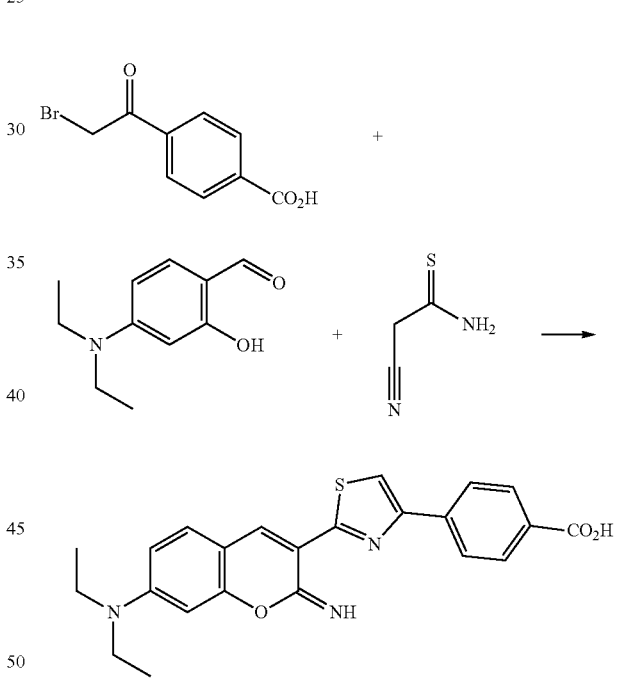

2-Cyanothioacetamide (0.41 g, 1 eq), p-diethylaminosalicylic aldehyde (0.8 g, 1 eq), 4-(2-bromoacetyl)benzoic acid (1 g, 1 eq) in EtOH (50 mL) were stirred at RT for 0.5 h. Triethylamine (0.25 g) was added and the reaction mixture was stirred at RT again for 1.5 h and precipitated product was filtered off. Yield ~89%. LC-MS: (+) 420 (M+1)$^+$.

p-[2-(7-(Diethylamino)-2-oxo-2H-chromen-3-yl)thiazol-4-yl]benzoic acid (Compound II-5) was prepared from hydrolyzing Compound II-5b in a mixture of EtOH-Water-HCl. Product filtered off and washed with EtOH. Yield 95%. $^1$H NMR (400 MHz, DMSO) δ 12.99 (s, 1H), 8.96 (s, 1H), 8.32 (s, 1H), 8.28-8.17 (m, 2H), 8.10-7.95 (m, 2H), 7.78 (d, J=9.0 Hz, 1H), 6.86 (dd, J=9.0, 2.4 Hz, 1H), 6.68 (d, J=2.3 Hz, 1H), 3.51 (q, J=7.0 Hz, 4H), 1.16 (t, J=7.0 Hz, 6H).

Compound II-7: 2-[2-oxo-7-((3-sulfopropyl)amino)-2H-chromen-3-yl]thiazole-5-carboxylic acid

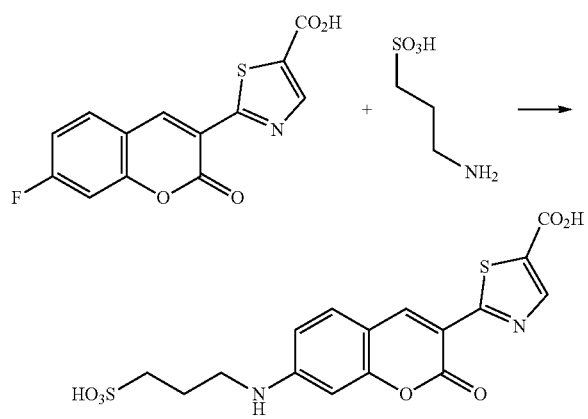

In a 10 mL 1-neck round-bottomed flask was added 7-fluoro coumarin (89 mg, 300 µmol), 3-amino-1-propanesulfonic acid (125 mg, 900 µmol) and DMSO (2 mL). N,N-Diisopropylethylamine (DIPEA, 261 µl, 1500 µmol) was added to the flask and heating to 80° C. was started. On heating, the reaction mixture changed color from pale yellow to orange/red. Heated at 80° C. for 18 h. Then the mixture was allowed to cool to RT, and stopped reaction by adding water (3 mL). Filtered reaction mixture through a 20 µm Nylon filter. Purified crude material via preparative HPLC (Axia column, Gradient 6-20). Yield: 28.6 µmol (9.5%).

Compound II-8: 4-Methyl-2-[2-oxo-7-((3-sulfopropyl)amino)-2H-chromen-3-yl]thiazole-5-carboxylic acid

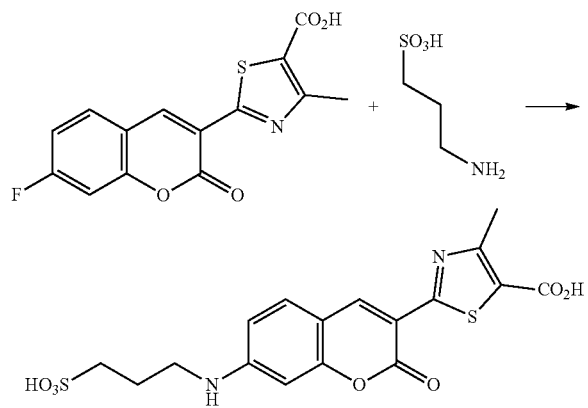

In a 10 mL 1-neck round-bottomed flask was added Compound II-54 (110 mg, 360 µmol), 3-amino-1-propanesulfonic acid (150 mg, 1080 µmol) and DMSO (2 mL). N,N-diisopropylethylamine (DIPEA, 313 µL, 1800 µmol) was added to the flask. The reaction was heated at 100° C. for 5 h. Then the reaction mixture was allowed to cool to RT, and stopped reaction by adding water (3 mL). Filtered reaction mixture through a 20 µm Nylon filter. Purified crude material by preparative HPLC (Axia column, Gradient 10-22). Yield: 74.5 µmol, 21%. Absorption at 439 nm (in 10 mM TRIS pH=8).

Compound II-11a: Ethyl 2-(2-(7-ethylamino-2-oxo-6-methyl-2H-chromen-3-yl)-4-thiazolyl)acetate

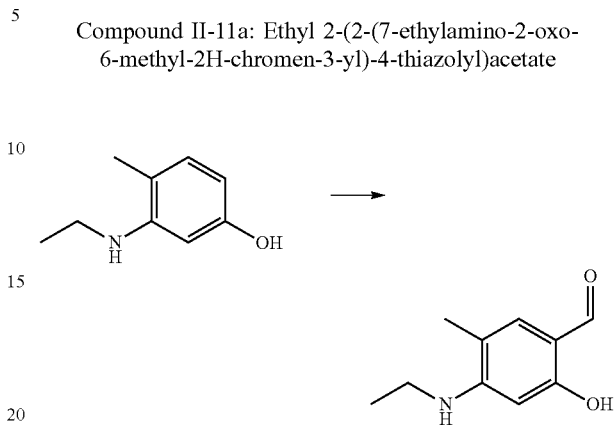

A mixture of 3-(ethylamino)-p-cresol (1 eq), anhydrous magnesium dichloride (1.5 eq) and anhydrous triethylamine (3.5 eq) in anhydrous acetonitrile was stirred under nitrogen at RT for 10 minutes. Paraformaldehyde (6.5 eq) was added and stirring was continued with refluxing for 4 h. Then the reaction mixture was cooled down to RT, aqueous HCl (10%) was added and the resulting mixture was extracted with dichloromethane. The combined organic layers were washed with water, dried over anhydrous magnesium sulfate and concentrated under reduced pressure and purification by column chromatography. Yield:15-20%.

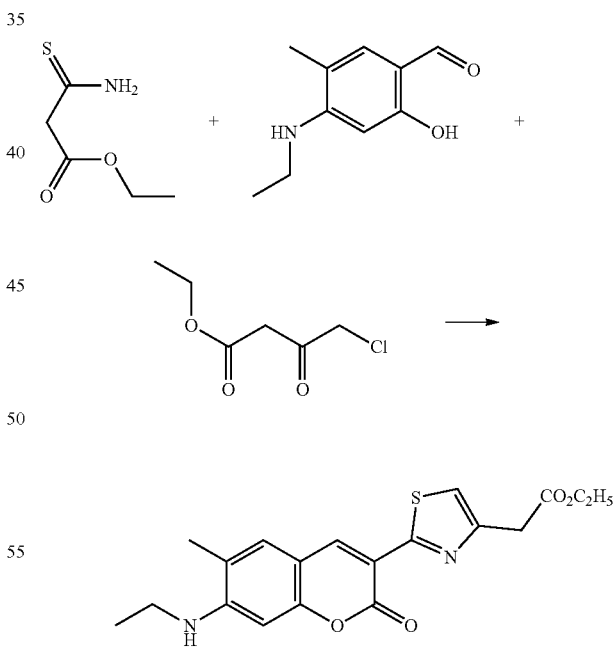

2-Ethoxycarbonylthioacetamide (300 mg, 1 eq), 3-ethylamino-4-methylsalisylic aldehyde (402 mg, 1.1 eq), ethyl 3-chloro-2-oxobutanoate (403 mg, 1.2 eq) in EtOH (3 mL) were heated at ~70° C. for 2 h. then at 90° C. for 0.5 h and was left stirring overnight at RT. Then the precipitate was filtered off, washed with EtOH (~0.5 mL) and water (2×0.5 mL). Yield 330 mg (~43%).

Compound II-11b: 2-[2-(7-(Butylamino)-2-oxo-2H-chromen-3-yl)thiazol-4-yl]acetic acid

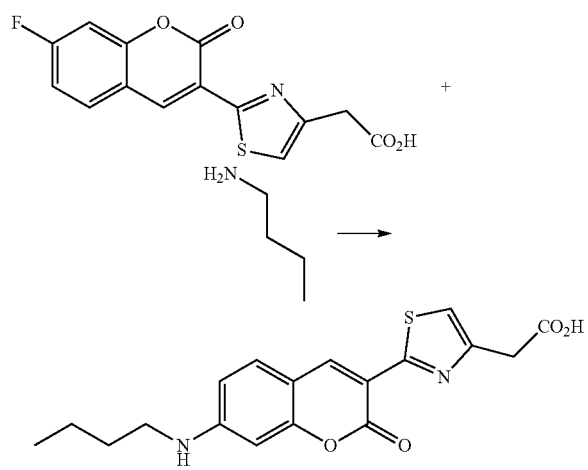

Compound II-11b was prepared from reacting Compound II-51 (20 mg, 66 μmol), butylamine (10 mg, 133 μmol) in DMSO (0.5 mL) and DIPEA (23 μl, 132 μmol). After heating at 110° C. for 5 h the reaction mixture was diluted with water (2 mL). An orange solid was filtered off and dried. Yield 6 mg (25%). LC-MS (+): 359 (M+1).

Compound II-12a: Ethyl 2-(2-(7-fluoro-2-oxo-2H-chromen-3-yl)-4-methyl-thiazol-5-yl)acetate

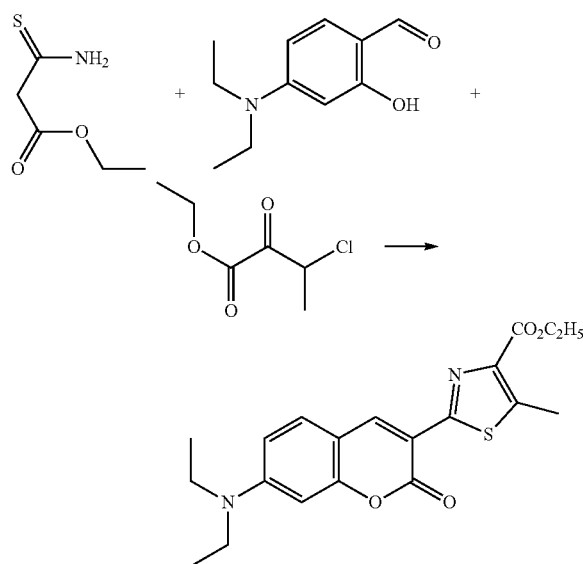

2-Ethoxycarbonylthioacetamide (5 g, 50 mmol, 1 eq), p-diethylaminosalisylic aldehyde (7.7 g, 55 mmol, 1.1 eq), ethyl 3-chloro-2-oxobutanoate (6.7 g, 41 mmol, 1.2 eq) in EtOH (100 mL) were heated at ~70° C. for 2 h. Tetrabutylammonium bromide (0.5 g) was added ant the reaction mixture was heated at 90° C. for 0.5 h and was left stirring overnight at RT. Then the precipitate was filtered off, washed with EtOH (~5 mL) and water (2×15 mL). Crystallization from EtOH. Yield 11.2 g (~85%). $^1$H NMR (400 MHz, DMSO-$d_6$) δ 8.87 (s, 1H), 7.77 (d, J=9.0 Hz, 1H), 6.85 (dd, J=9.1, 2.5 Hz, 1H), 6.67 (d, J=2.4 Hz, 1H), 4.28 (q, J=7.1 Hz, 2H), 3.51 (q, J=7.0 Hz, 4H), 2.68 (s, 3H), 1.31 (t, J=7.1 Hz, 3H), 1.16 (t, J=7.0 Hz, 6H).

[2-(7-Diethylamino-2-oxo-2H-chromen-3-yl)-4-methyl-thiazol-5-yl)carboxylic acid (Compound II-12) was prepared from reacting the corresponding ethyl ester Compound II-12a with LiOH following similar procedure described in the preparation of Compound II-51. Target compound was isolated by crystallization from ethanol. Yield 58%. $^1$H NMR (400 MHz, DMSO-$d_6$) δ 8.86 (s, 1H), 7.76 (d, J=9.1 Hz, 1H), 6.84 (dd, J=9.1, 2.5 Hz, 1H), 6.66 (d, J=2.4 Hz, 1H), 3.51 (q, J=7.0 Hz, 4H), 2.67 (s, 3H), 1.16 (t, J=7.0 Hz, 6H).

Compound II-12b: Ethyl 2-(2-(7-fluoro-2-imino-2H-chromen-3-yl)-4-methyl-thiazol-5-yl)acetate

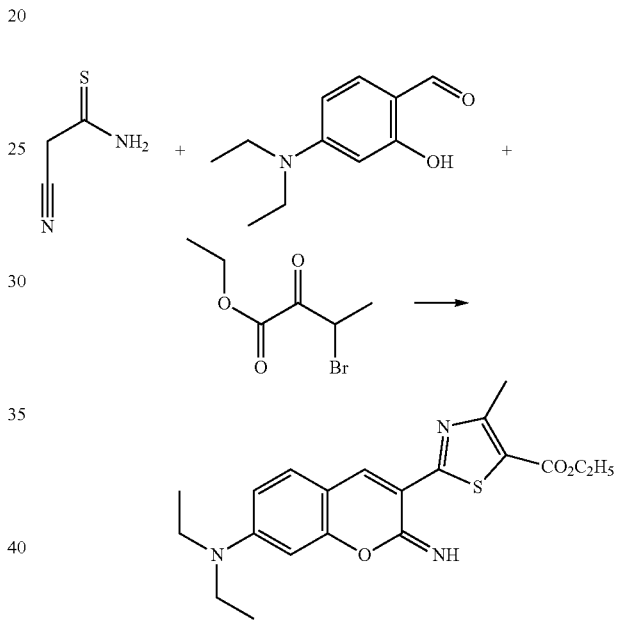

2-Cyanothioacetamide (5 g, 50 mmol, 1 eq), p-diethylaminosalisylic aldehyde (10.6 g, 55 mmol, 1.1 eq), 3-bromo-2-oxobutanoate (12.52 g, 60 mmol, 1.2 eq) in EtOH (80 mL) were heated at RT for 3 h. Precipitate was filtered off, washed with EtOH (~5 mL). Yield 9 g (47%). This compound hydrolyzed in diluted hydrochloric acid into Compound II-12a.

Compound II-33a: 2-[2-(7-(3-(tert-Butoxycarbonyl)azetidin-1-yl)-2-oxo-2H-chromen-3-yl)thiazol-4-yl]acetic acid

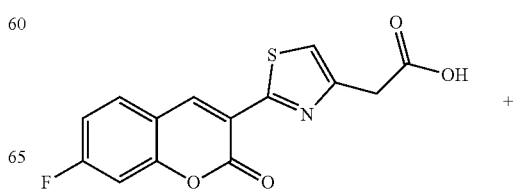

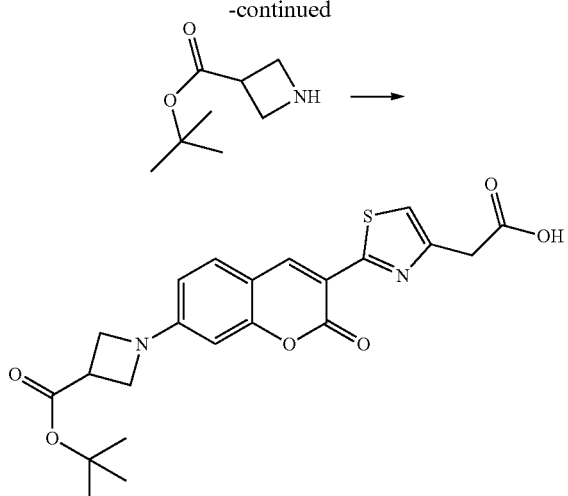

Compound II-51 (31 mg, 100 µmol), 3-(tert-butoxycarbonyl)azetidine hydrochloride (39 mg, 200 µmol) in DMSO (0.5 mL) and DIPEA (35 µL, 200 µmol) was heated at 90° C. for 5 h. The reaction mixture was diluted with water and the product isolated by preparative HPLC. Yield: 25%.

2-[2-(7-(Azetidin-1-yl)-2-oxo-2H-chromen-3-yl)thiazol-4-yl]acetic acid (Compound II-33) was prepared by reacting Compound II-51 (31 mg, 100 µmol), azetidine (13.5 µL, 200 µmol) in DMSO (1 mL) and DIPEA (35 µl, 200 µmol) following similar procedure in the preparation of II-33a. Yield: 49 µmol (49%). LC-MS (+): 343 (M+1).

Compound II-43c: Ethyl 2-(7-(ethylamino)-6-methyl-2-oxo-2H-chromen-3-yl)-4,5,6,7-tetrahydrobenzo[d]thiazole-6-carboxylate

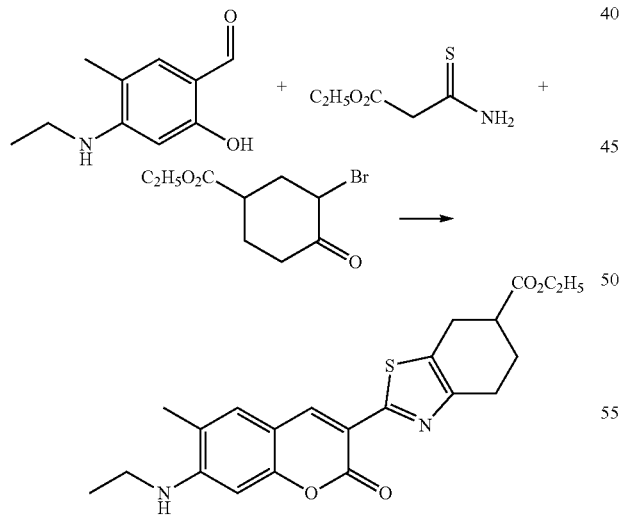

2-Bromo-4-ethoxycarbonylcyclohexanone (400 mg, 1.8 mmol), 2-hydroxy-4-ethylamino-5-methyl benzaldehyde (293 mg, 1.64 mmol), ethyl-3-amino-3-thioxoproponate (265 mg, 1.8 mmol) were mixed with ethanol (10 mL). The reaction mixture was stirred and heated at 80° C. for 2 h. To the end of this time starting material is consumed. The reaction was allowed to cool to RT. The solvent was removed in vacuo and then the solid residue was dissolved in ethyl acetate. The solution was washed with water and brine. Dried the organic layer over magnesium sulfate, filtered and dried in vacuo. Purified by flash chromatography. Dried in vacuo to yield a yellow-colored power. Yield 75 mg (11%). 1H NMR (400 MHz, CDCl3) δ 7.32 (s, 1H), 6.50 (s, 1H), 4.19 (qd, J=7.1, 1.0 Hz, 2H), 3.30 (dd, J=7.6, 3.9 Hz, 2H), 3.17-3.01 (m, 2H), 3.01-2.76 (m, 2H), 2.36-2.25 (m, 1H), 2.21-2.14 (m, 3H), 2.10-1.97 (m, 1H), 1.48 (d, J=31.1 Hz, 2H), 1.37 (td, J=7.1, 1.7 Hz, 3H), 1.29 (t, J=7.1 Hz, 3H).

2-(7-(Ethylamino)-6-methyl-2-oxo-2H-chromen-3-yl)-4,5,6,7-tetrahydrobenzo[d]thiazole-6-carboxylic acid (Compound II-43b) was prepared by reacting the corresponding ethyl ester II-43c with LiOH following similar procedure described in the preparation of Compound II-51. Yield: 54%. UV-Vis: Abs 441 nm in 50% EtOH/H$_2$O. Fluorescence: 498 nm in 50% EtOH/H$_2$O.

Compound II-43e: Ethyl 2-(7-(diethylamino)-2-oxo-2H-chromen-3-yl)-4,5,6,7-tetrahydrobenzo[d]thiazole-4-carboxylate

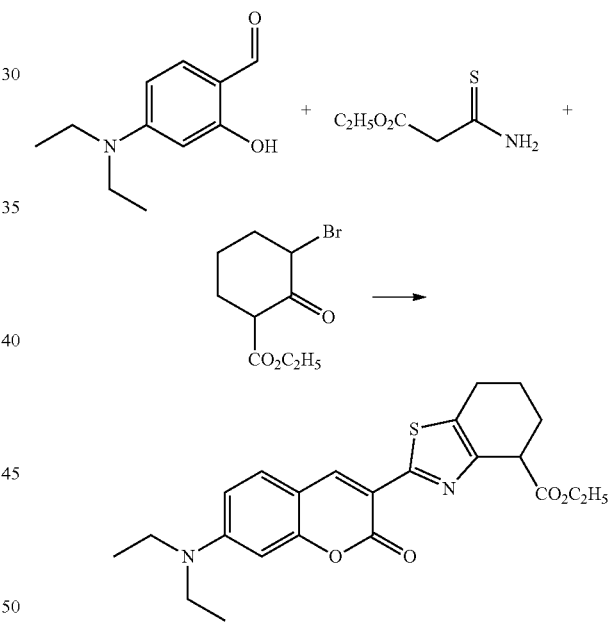

4-Diethylamino-salicylaldehyde (0.35 g, 1.82 mmol), ethyl 3-bromo-2-oxocyclohexane-1-carboxylate (0.5 g, 2.00 mmol) and ethyl-3-amino-3-thioxoproponate (0.29 g, 2.00 mmol) were mixed with ethanol (20 mL). The reaction mixture was stirred and heated at 80° C. for 2 h. To the end of this time starting material is consumed. The reaction was allowed to cool to RT. The solvent was removed in vacuo and then the residue was dissolved in ethyl acetate. The solution was washed with water and brine. Dried the organic layer over magnesium sulfate, filtered and dried in vacuo. Purified by flash chromatography. Dried in vacuo to yield a yellow-colored oil. Yield 300 mg (38%).

Compound II-47a: Ethyl 2-[2-(7-(4-methylpiper-azin-1-yl)-2-oxo-2H-chromen-3-yl)thiazol-4-yl]ac-etate

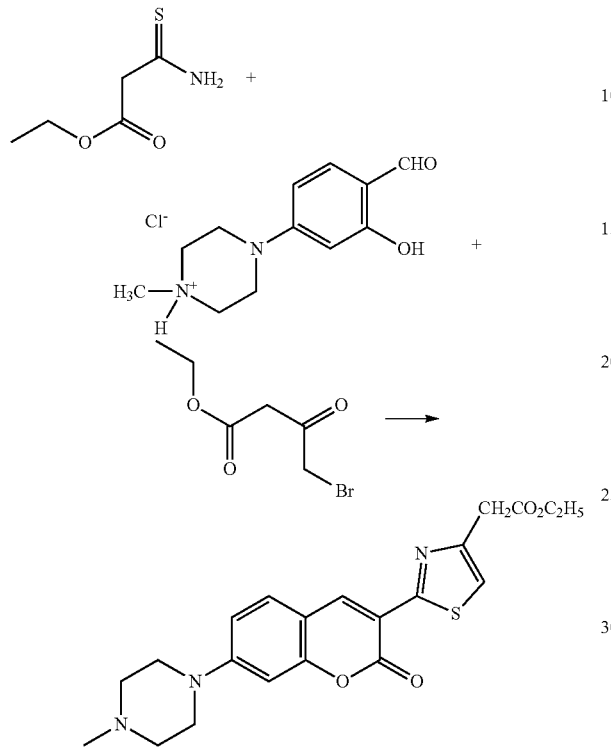

A mixture of 4-fluorosalicylaldehyde (5 g, 1 eq), 1-methyl-piperazine (3.93 g) in DMSO (6 mL) was heated at 100° C. for 10 h. Reaction mixture was left at RT overnight. A part of solvent and excess of N-methyl pipera- zine distilled off in vacuum at 75° C. This salicylic aldehyde derivative pure enough for next step, but may be converted to a salt for long storage. For example, hydrogen chloride salt could be prepared. To this viscous residue solution of HCl in anhydrous diethylether (100 ml, 1M) was added. Ether was decanted and product triturated with ethanol. After 1 h product filtered off.

Ethyl 3-amino-3-thioxopropanoate (0.6 g, 1 eq, 4.08 mmol) and 4-(4-methyl-piperazin-1-yl)-2-hydroxybenzalde-hyde hydrochloride (1.05 g, 1 eq, 4.08 mmol) mixed together in absolute ethanol (5 mL) and ethyl 4-bromoac-etoacetate was added. Reaction mixture was stirred at RT for about 1 h then kept at 80° C. for 4 h. A new yellow precipitate was formed. Reaction mixture was left at RT overnight. Product was filtered off, washed with EtOH and crystallized as hydrochloride salt from absolute ethanol. Dissolved in water and converted to base with sodium bicarbonate. Yield 1.39 g (82.5%).

2-(2-(7-(4-methylpiperazin-1-yl)-2-oxo-2H-chromen-3-yl)thiazol-4-yl)acetic acid (Compound II-47) was prepared by reacting the corresponding ethyl ester (Compound II-47a, 207 mg, 1 eq) with LiOH (60 mg, 5 eq) in EtOH (0.25 mL) and water (2 mL). The reaction mixture was stirred at 30-40 C for about 3 h. Nearly clear solution was filtered, acidified with acetic acid and was left overnight at RT. Then the product was filtered off, washed with cold water (2×1 0.5 mL) and dried an air. Yield 0.15 g (78.8%). $^1$H NMR (400 MHz, DMSO) δ 8.77 (s, 1H), 7.77 (d, J=8.9 Hz, 1H), 7.51 (s, 1H), 7.05 (dd, J=9.0, 2.4 Hz, 1H), 6.92 (d, J=2.3 Hz, 1H), 3.79 (s, 2H), 3.44 (t, J=5.2 Hz, 4H), 2.45 (t, J=5.1 Hz, 5H), 2.23 (s, 3H).

II-48: 2-[2-(7-(4-methyl-4-(3-sulfonatopropyl)piper-azin-1-yl)-2-oxo-2H-chromen-3-yl)thiazol-4-yl]ace-tic acid

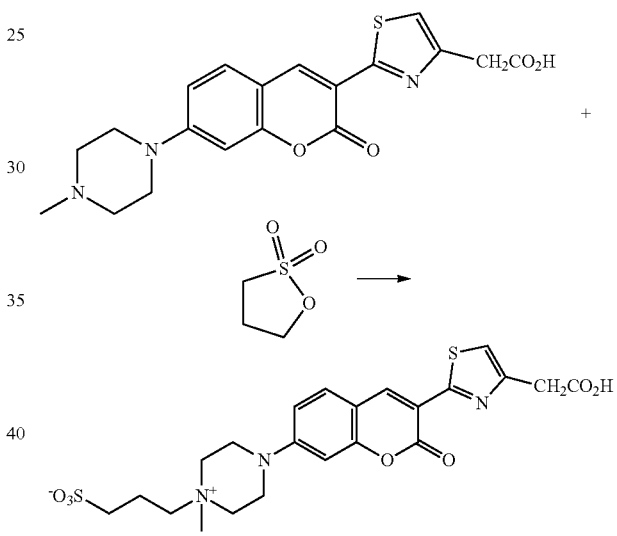

Mixture of 2-(2-(7-(4-methylpiperazin-1-yl)-2-oxo-2H-chromen-3-yl)thiazol-4-yl)acetic acid (Compound II-47, 38 mg, 1 eq) and 1,3-propanesultone (12.2 mg, 1 eq) in dry DMF (0.5 mL) were heated at 100° C. for 3 h. Product precipitated with dry diethyl ether, filtered off, washed with acetone and dried. Yield 54 mg (83%).

Compound II-49a: Ethyl 2-[2-(7-(4-methyl-4-(5-carboxylatopenthyl)piperazin-1-yl)-2-oxo-2H-chromen-3-yl)thiazol-4-yl]acetate

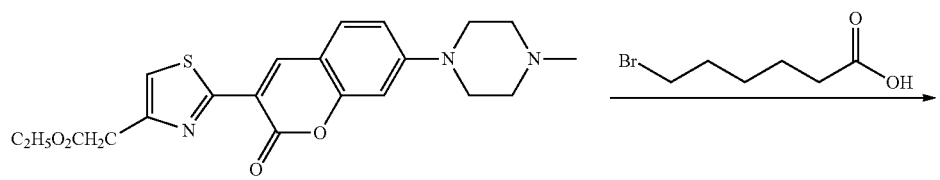

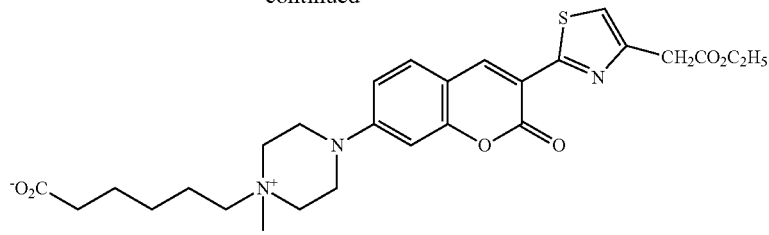

Mixture of ethyl 2-(2-(7-(4-methylpiperazin-1-yl)-2-oxo-2H-chromen-3-yl)thiazol-4-yl)acetate (Compound II-47a, 413 mg, 1 eq) and 6-bromohexanoic acid (195 mg, 1 eq) in dry acetonitrile (5 mL) was heated at 90° C. for 12 h. Next day precipitated product was filtered off, washed with acetone and dried. Yield 321 mg (~60%).

Compound II-49c: 3-(4-(3-(4-(Ethoxycarbonylmethyl)thiazol-2-yl)-2-oxo-2H-chromen-7-yl)-1-methylpiperazin-1-ium-1-yl)propylsulfonate

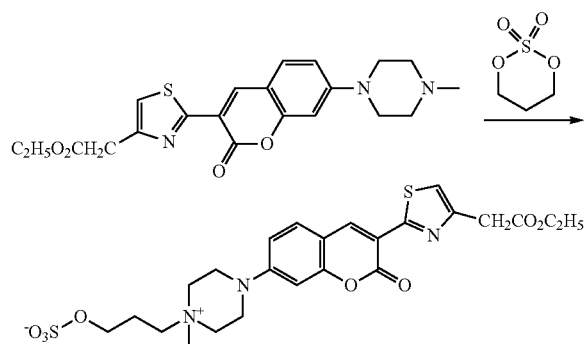

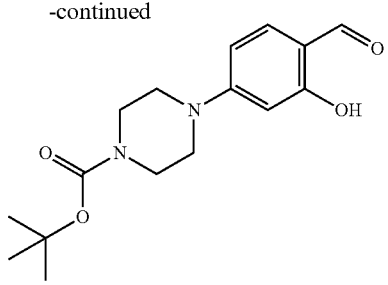

Mixture of ethyl 2-(2-(7-(4-methylpiperazin-1-yl)-2-oxo-2H-chromen-3-yl)thiazol-4-yl)acetate (Example II-6, 100 mg, 1 eq) and 1,3-dioxa-2-thiane-2,2-dioxide (50 mg, 1 eq) in dry acetonitrile (1 mL) were heated at 80° C. for 1 h. Then precipitated product was filtered off, washed with acetone and dried. Yield 110 mg (82%). $^1$H NMR (400 MHz, TFA-d) δ 8.90 (s, 1H), 7.87 (d, J=9.1 Hz, 1H), 7.81 (s, 1H), 7.24 (dd, J=9.2, 2.4 Hz, 1H), 7.06 (d, J=2.3 Hz, 1H), 4.58 (t, J=5.3 Hz, 2H), 4.46 (q, J=7.2 Hz, 2H), 4.31 (s, 2H), 4.26-3.88 (m, 8H), 3.80 (t, J=9.3 Hz, 2H), 3.40 (s, 3H), 2.47 (d, J=6.4 Hz, 2H), 1.45 (t, J=7.2 Hz, 3H).

Compound II-50a: Ethyl 2-(2-(7-(4-t-butoxycarbonylpiperazin-1-yl)-2-oxo-2H-chromen-3-yl)thiazol-4-yl)acetate

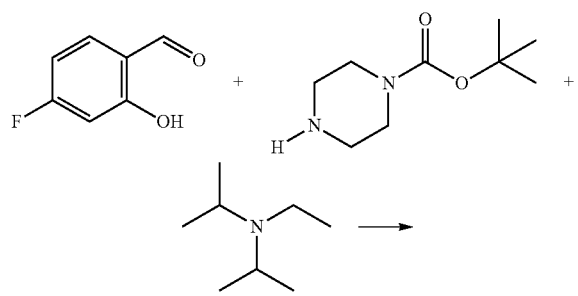

A mixture of 4-fluorosalicylaldehyde (2.80 g, 20 mmol, 1 eq), 1-Boc-piperazine (4.09 g, 22 mmol) and Hunig Base in DMSO (6 mL) was heated at 80° C. for 10 h. Reaction mixture was left at RT overnight. Crystallized reaction mass was diluted with small volume of acetonitrile and product filtered off, washed with water.

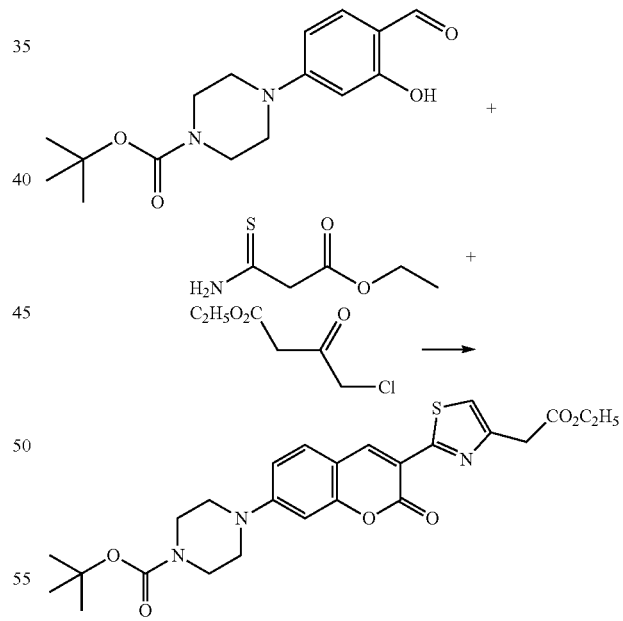

A mixture of (4-t-Butoxycarbonylpiperazin-1-yl)salicylic aldehyde (1.5 g, 1 eq), 2-ethoxycarbonyl-thioacetamide and ethyl 4-chloroacetoacetate was stirred at 80-85° C. in EtOH (25 mL) 1 h and left overnight at RT. Then the reaction mixture was diluted with water (25 mL), added sodium bicarbonate and yellow precipitate filtered off. May be crystallized from ethanol. Yield 78%. $^1$H NMR (400 MHz, DMSO) δ 8.80 (s, 1H), 7.83 (d, J=9.0 Hz, 1H), 7.56 (s, 1H), 7.07 (ddd, J=9.0, 4.5, 2.4 Hz, 1H), 6.95 (d, J=2.3 Hz, 1H), 4.14 (q, J=7.1 Hz, 2H), 3.89 (d, J=1.4 Hz, 2H), 3.48 (s, 7H), 3.41-3.35 (m, 1H), 2.82 (t, J=5.2 Hz, 1H), 1.44 (s, 9H), 1.23 (t, J=7.1 Hz, 3H).

Compound II-1a': Ethyl 2-(4-(7-(diethylamino)-2-oxo-2H-chromen-3-yl)thiazol-2-yl)acetate

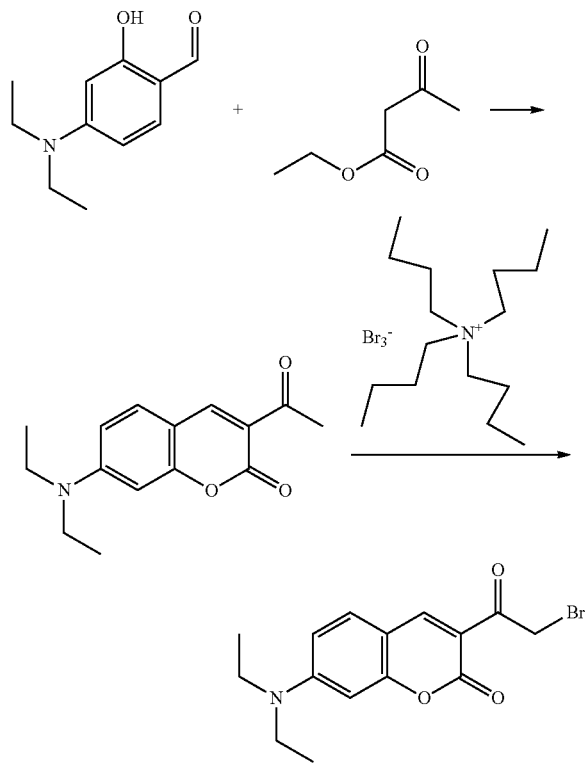

p-Diethylamino-salicylic aldehyde (5.50 g) and ethyl acetoacetate (3.89 g) in absolute EtOH (70 mL) was stirred 10 min at RT. Piperidine (3 drops) was added and the reaction mixture was refluxed for 2 h. The crystalline product as yellow solid precipitate was filtered off, washed with EtOH.

A solution of 3-acetyl-7-diethylamino-2H-chromen-2-one (5.18 g, 20 mmol) and tetra-n-butyl ammonium tribromide (19.3 g, 40 mmol) in dichloromethane (100 mL) was stirred at RT for 48 h. The resulting precipitate was filtered off and washed with ethyl acetate.as a yellow prisms (yield ~80%). Product was used in the next step without further purification.

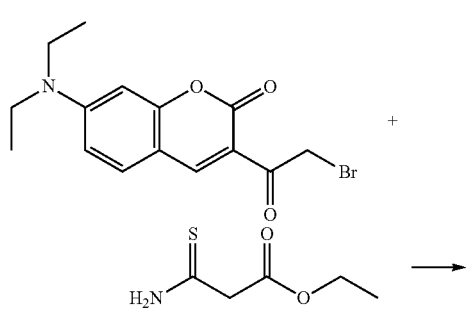

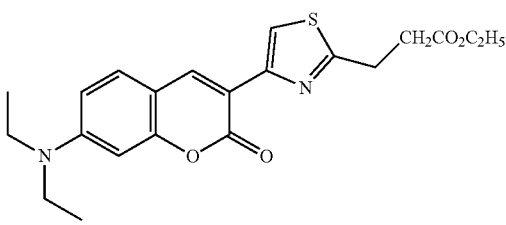

3-(2-Bromoacetyl)-7-diethylamino-2H-chromen-2-one (700 mg, 1 egv) from previous step and ethyl 3-amino-3-thioxopropanoate (380 mg, 1.25 eq) mixed with ethanol (5 mL) and reaction mixture was kept 2 h at 80° C. The reaction mixture was left at RT overnight. The colorless precipitate was filtered off and washed with ethanol than transferred to a beaker with water (15 mL) and was neutralized with sodium bicarbonate. After 1 h the product was filtered off and washed with water. Yield 780 mg (94%). $^1$H NMR (400 MHz, CDCl$_3$) δ 8.64 (s, 1H), 8.30 (s, 1H), 7.45 (d, J=8.7 Hz, 1H), 6.74 (s, 1H), 6.63 (s, 1H), 4.28 (q, J=7.1 Hz, 2H), 4.14 (s, 2H), 3.47 (q, J=7.1 Hz, 4H), 1.34 (td, J=7.1, 0.6 Hz, 3H), 1.26 (t, J=7.1 Hz, 6H).

2-(4-(7-(Diethylamino)-2-oxo-2H-chromen-3-yl)thiazol-2-yl)acetic acid (Compound II-1') was prepared by reacting the corresponding ethyl ester II-1a' with LiOH following similar procedure described in the preparation of II-51. Yield 0.275 g (~74%). $^1$H NMR (400 MHz, DMSO) δ 8.61 (s, 1H), 8.13 (s, 1H), 7.65 (d, J=9.0 Hz, 1H), 6.75 (dd, J=8.9, 2.5 Hz, 1H), 6.59 (d, J=2.4 Hz, 1H), 4.10 (s, 2H), 3.46 (q, J=7.0 Hz, 4H), 1.14 (t, J=7.0 Hz, 6H).

General Procedure for Preparing Nucleotide Labeled with Compound of Formula (I), (II) or (II')

Appropriate dye (1.0 eq) in dimethylacetamide (DMA) treated with diisopropylethylamine (DIPEA, 10 eq) and 2-(endo-5-norbornene-2.3-dicarboxylimide)-1,1,3,3-tetramethyluronium tetrafluoroborate (TNTU) (1.2 eq). The reaction mixture was stirred for 10 min at RT. Relevant amino-substituted nucleotide derivatives (nucleotide with a linker moiety containing an amino functional group, 1.2 eq) then added, followed by triethylamine. The reaction mixture stirred at RT for 18 h. After of coupling completion solvents were distilled of in vacuum, the residue was pre-purified by ion exchange column (Sephadex, eluent TEAB with gradient 0.1M to 1.0 M) and further purified using reverse phase HPLC. Composition of the product confirmed by LC-MS and HRMS.

TABLE 3

Characterizations of various ffNs labeled with the dyes of Formula (II)

| No. | Dyes | Base | Linker | Mw (dye) | Mw | Ex/Em (nm) (SRE)* |
|---|---|---|---|---|---|---|
| 1 | II-6 | C | sPA | 358 | 1263 | 480/519 |
| 2 | II-2 | C | sPA | 358 | 1263 | 467/511 |
| 3 | II-5 | C | sPA | 420 | 1324 | 450/503 |
| 4 | II-1 | C | sPA | 424 | 1328 | 442/497 |
| 5 | II-8 | C | sPA | 424 | 1328 | 455/503 |

*The spectral property of the labelled ffNs were measured in a scan mix at RT (excitation 460 nm).

The structures of some exemplary ffCs and ffAs in Table 3 are shown below:

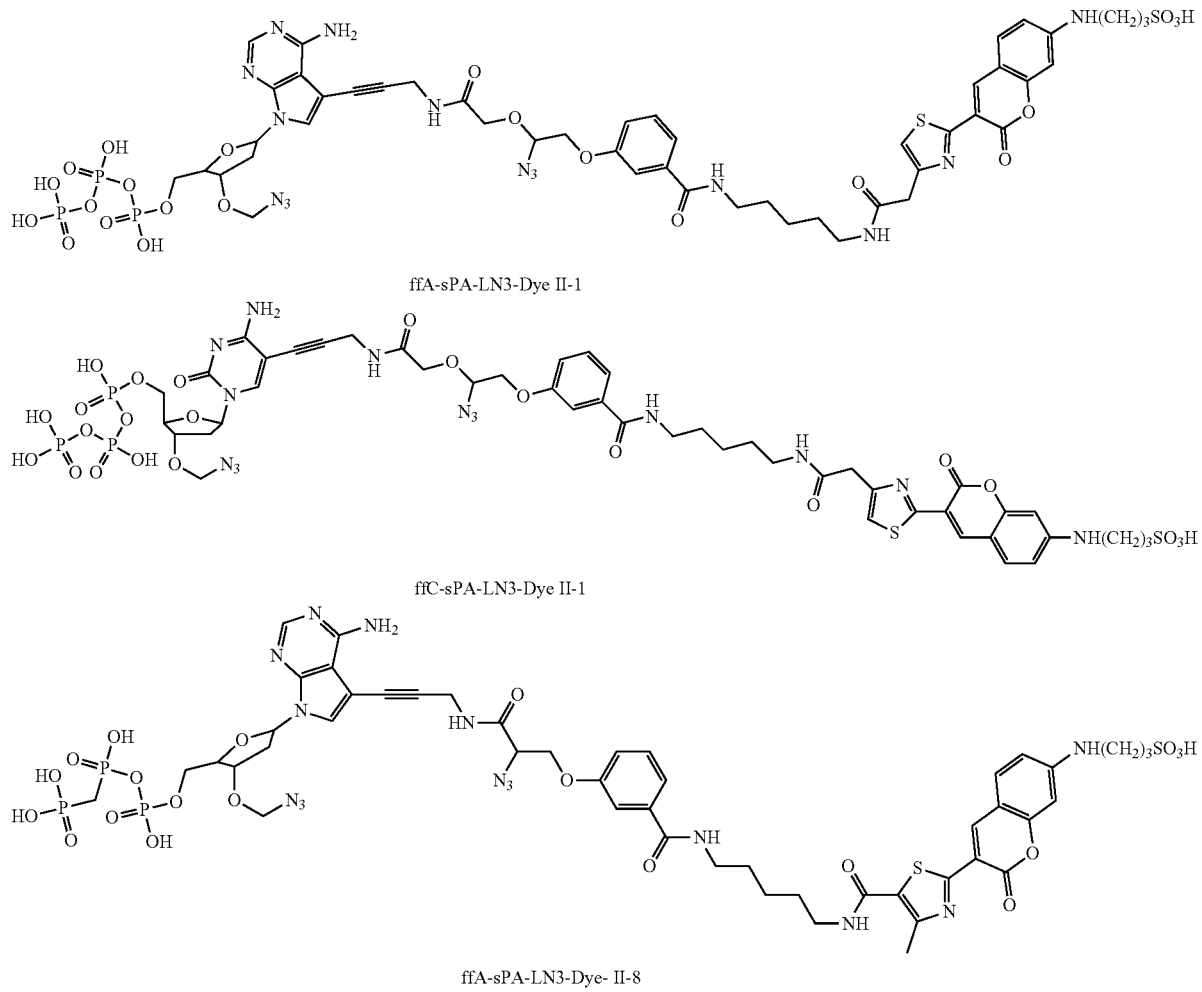

ffA-sPA-LN3-Dye II-1 ffC-sPA-LN3-Dye II-1 ffA-sPA-LN3-Dye- II-8

Figure 3A:
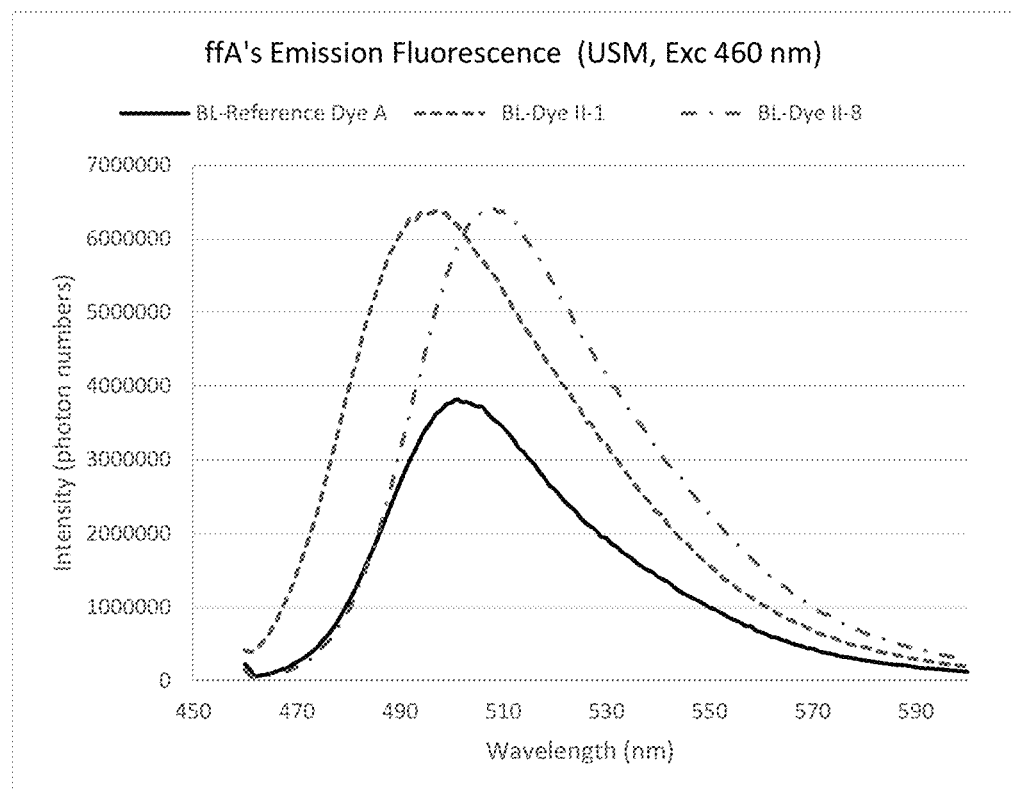
FIG. 3A illustrates the emission spectra of a fully functionalized A nucleotide (ffA) labeled with reference Dye A as compared to the same ffA labeled with Dye II-1 or Dye II-8 in a buffer solution when excited at 460 nm.

FIG. 3A illustrates the emission spectra of a fully functionalized A nucleotide (ffA) labeled with reference Dye A as compared to the same ffA labeled with Dye II-1 or Dye II-8 in a buffer solution when excited at 460 nm.

Figure 3B:
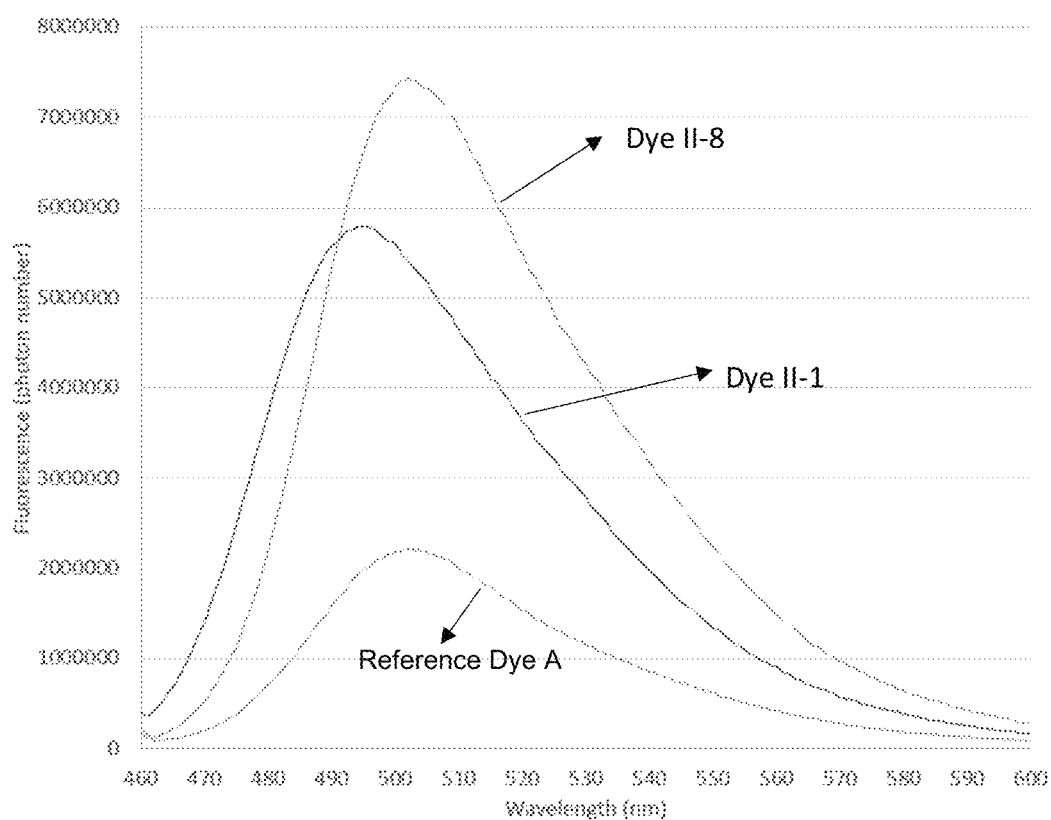
FIG. 3B illustrates the emission spectra of a fully functionalized C nucleotide (ffC) labeled with reference Dye A as compared to the same ffC labeled with Dye II-1 and Dye II- in a buffer solution when excited at 460 nm.

FIG. 3B illustrates the emission spectra of a fully functionalized C nucleotide (ffC) labeled with reference Dye A as compared to the same ffC labeled with Dye II-1 and Dye II-8 in a buffer solution when excited at 460 nm.

It was observed that Dyes II-1 and II-8 had sufficient absorption at excitation by blue laser wavelength (~460 nm) as compared to the reference Dye A and provided stronger fluorescent signal in the "blue-emission" detection region (about 470-520 nm). The results demonstrate the utility of these dyes as fluorescent biomarkers, for example, in nucleic acid sequencing applications.

Example 4. Two-Channel Sequencing Applications

The efficiency of the fully functionalized nucleotides labeled with the new dyes (Dyes I-4a and I-3a; Dyes II-1 and II-8) described herein in sequencing application was demonstrated in the two-channel detection method on Illumina's Miseq® platform. With respect to the two-channel methods described herein, nucleic acids can be sequenced utilizing methods and systems described in U.S. Patent Application No. 2013/0079232, the disclosure of which is incorporated herein by reference in its entirety. Blue exposure (Chanel 1) 500 ms, Green exposure (Chanel 2) 1000 ms; Nominal 1× exposure is blue 450 ms and green exposure is 540 ms, which correspond to around 3.5 J/cm$^2$. Performance of the ffA/ffC labeled with Dye I-4a, Dye I-3a, Dye II-1 or Dye II-8 were compared with the sequencing data generated from the ffNs labeled with the standard dye set used on Miseq®. These data are shown in FIGS. 4A-4C and 5A-5C. The data clearly demonstrated that ffNs based on Dyes I-4a, I-3a, II-1 and II-8 have comparable chemical stability to the Reference Dye A and are suitable for sequencing. Each sequencing run was performed for 151 cycles at five different light dosage (1×, 3×, 5×, 7.5× and 10×).

In the two-channel detection, a nucleic acid can be sequenced by providing a first nucleotide type that is detected in a first channel, a second nucleotide type that is detected in a second channel, a third nucleotide type that is detected in both the first and the second channel and a fourth nucleotide type that lacks a label that is not, or minimally, detected in either channel. The scatterplots were generated by RTA2.0.93 analysis of an experiment. The scatterplots are illustrated in FIGS. 6A-6H.

Figure 4A:
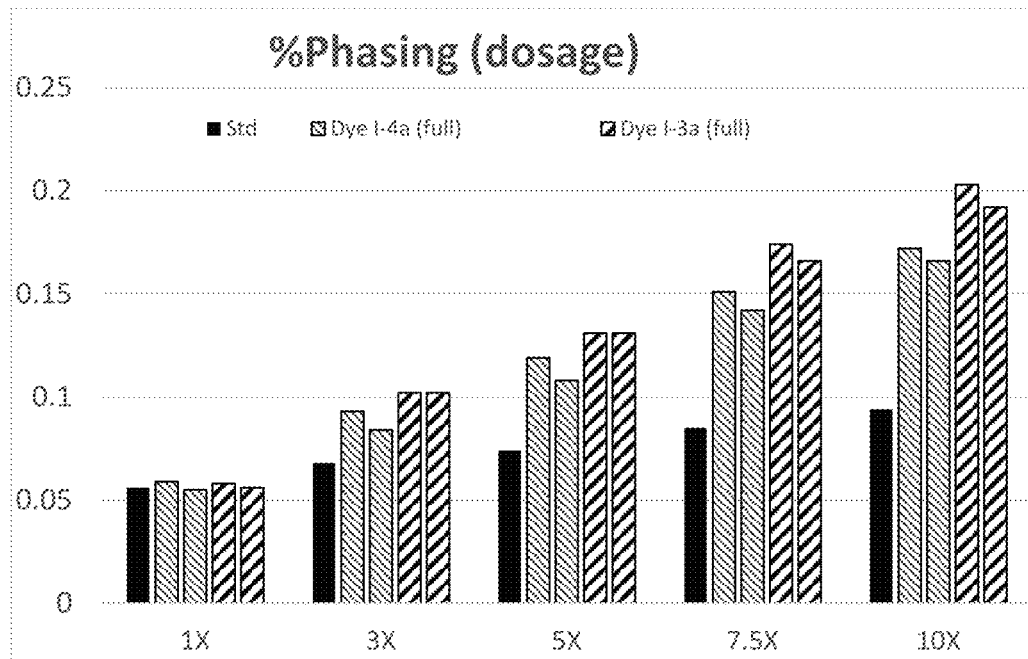
FIGS. 4A-4C illustrates the sequencing metrics (% phasing, % error rate, % remaining signal) when the ffAs and ffCs used on Illumina's Miseq® sequencing platform are labeled with Dye I-3a or Dye I-4a, as compared to the sequencing metrics with the ffNs labeled with the standard dye set used on Miseq®.
Figure 4B:
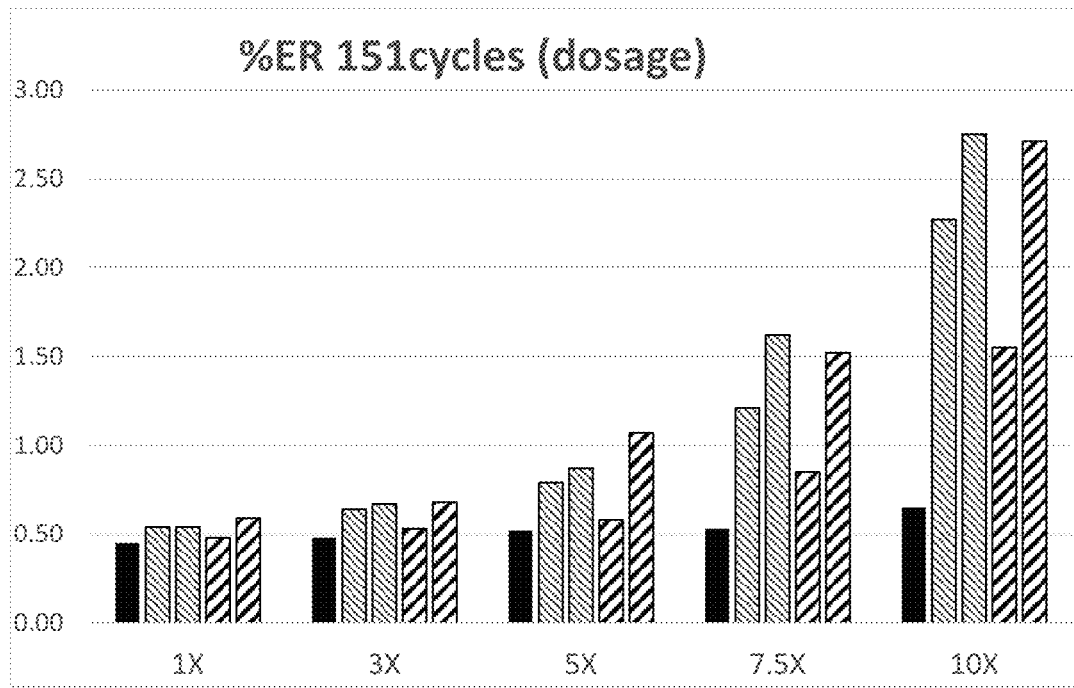
Figure 4C:
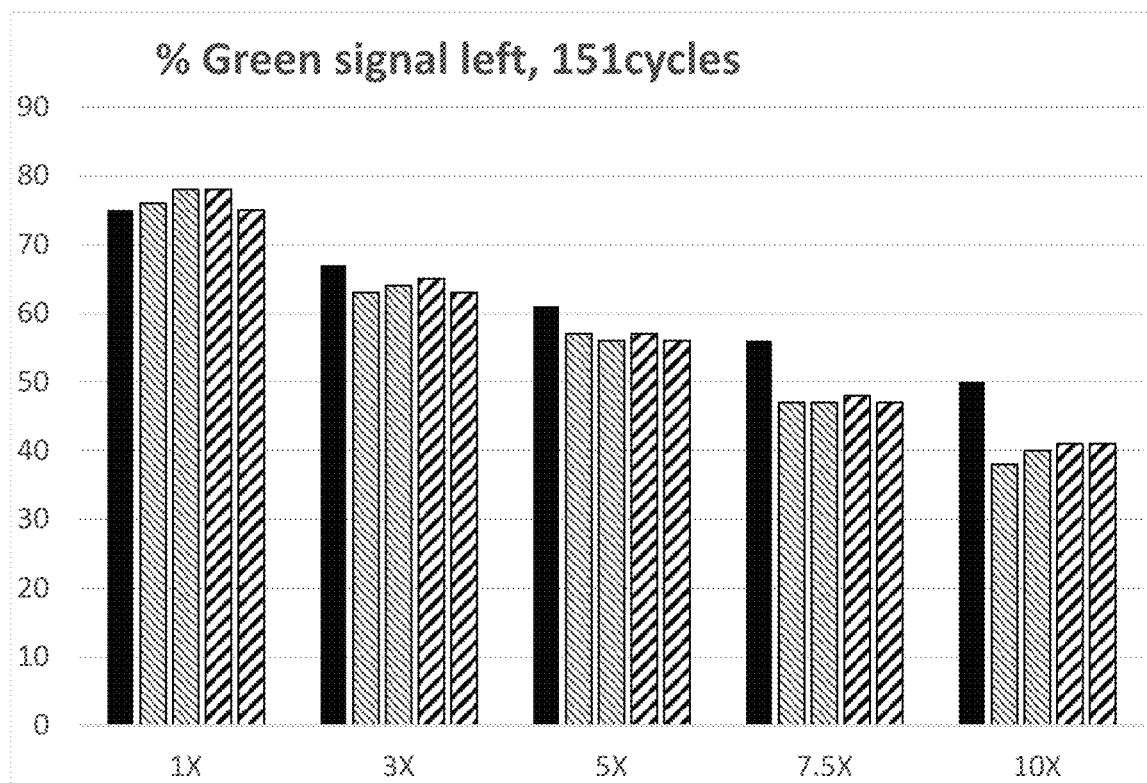

FIGS. 4A-4C illustrate the sequencing metrics when the ffAs and ffCs used in the Miseq® sequencing platform were labeled with Dye I-4a (ffC=1.25 uM; ffA=1.5 uM) or Dye I-3a (ffC=1.5 uM; ffA=1.6 uM) as compared to the ffNs labeled with the standard dye set, when different dosage of light were used (1×, 3×, 5×, 7.5× and 10×). For the ffNs labeled with standard dye set, ffC-sPA-Reference Dye A and ffA-BL-Reference Dye A were used. An DNA polymerase Pol 1901 was used for incorporation of the ffNs at 90 ug/ml final concentration. It was observed that the ffA/ffC labeled with Dyes I-3a and I-4a provided comparable sequencing results to those labeled with Reference Dye A at 1× and 3× light dosage.

Figure 5A:
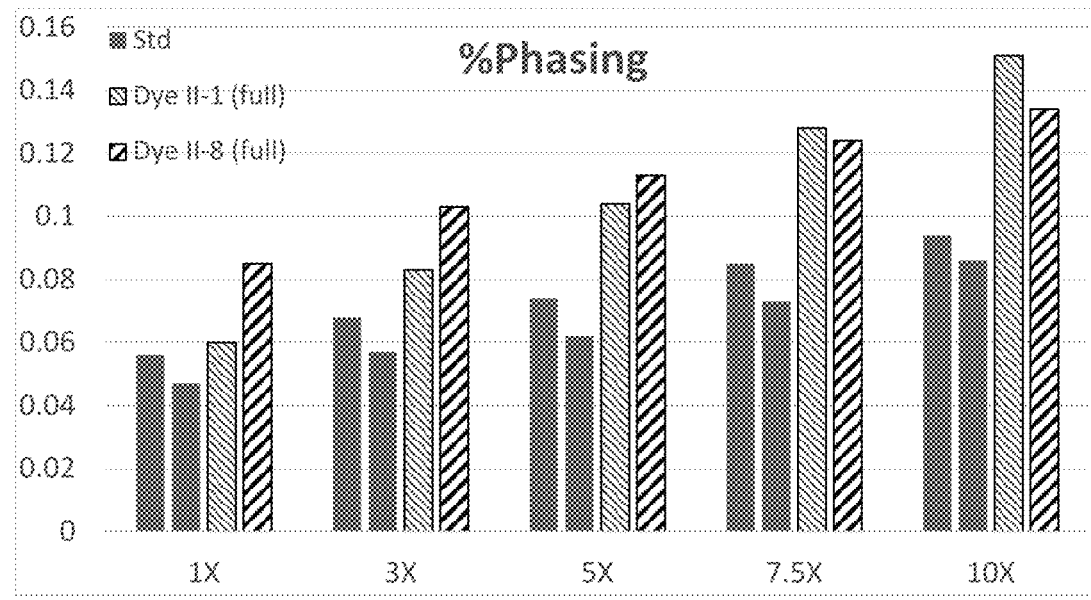
FIGS. 5A-5C illustrates the sequencing metrics (% phasing, % error rate, and % remaining signal) when the ffCs used in the Miseq® sequencing platform are labeled with Dye II-1 or Dye II-8, as compared to the to the sequencing metrics with the ffNs labeled with the standard dye set used on Miseq®.
Figure 5B:
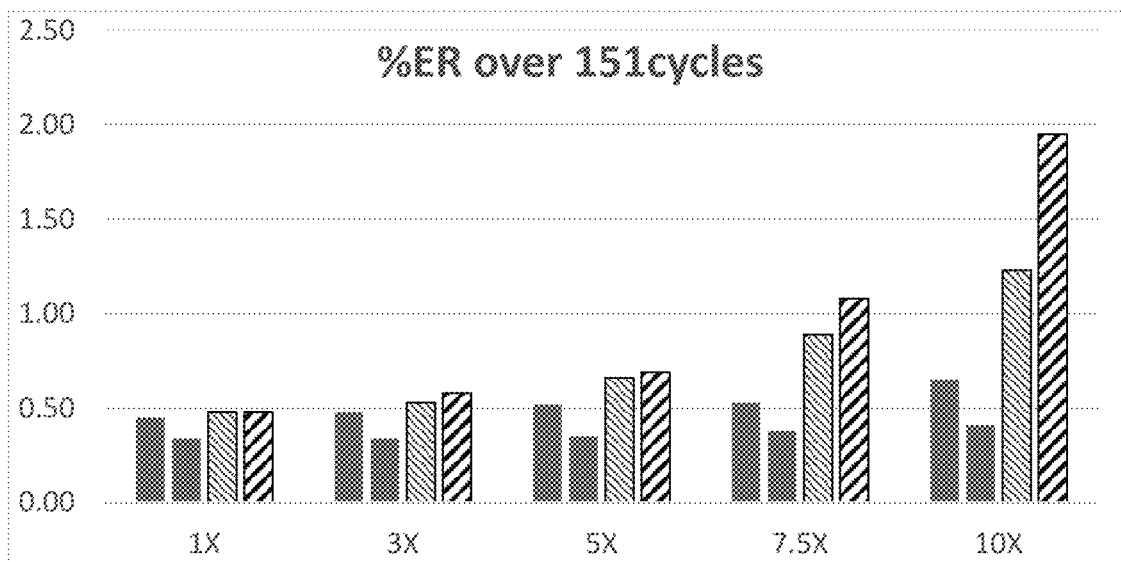
Figure 5C:
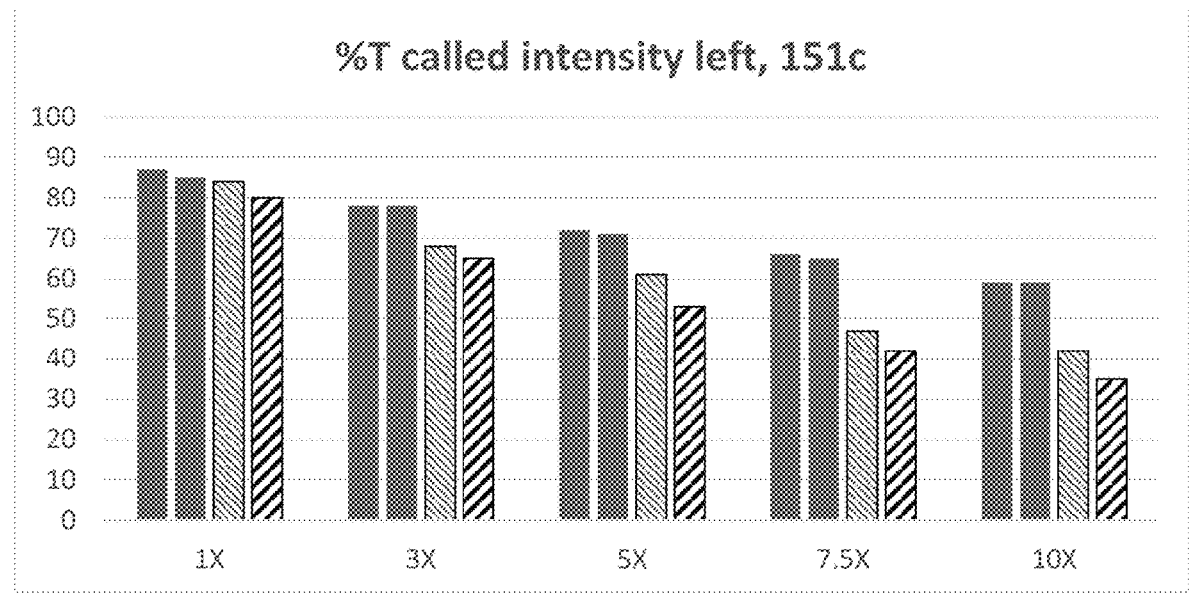
Figure 6A:
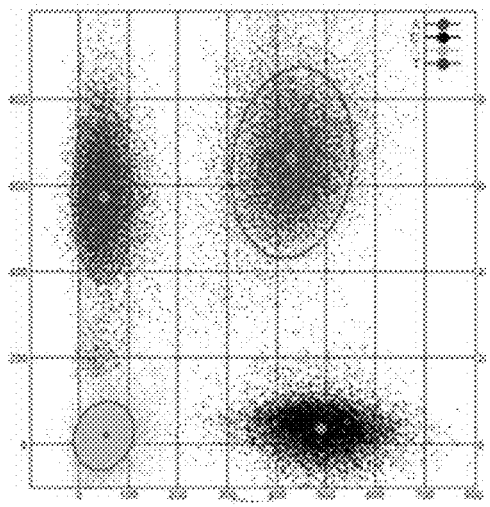
FIGS. 6A-6B are scatterplots illustrating the usability of ffA and ffC labeled with Dye I-4a where presented ratio of signals from ffC and ffT nucleotides after one dose of light exposure (C/T @ 1×) and ratio of appropriate signals after ten doses of exposure (C/T @ 10×/1×).
Figure 6B:
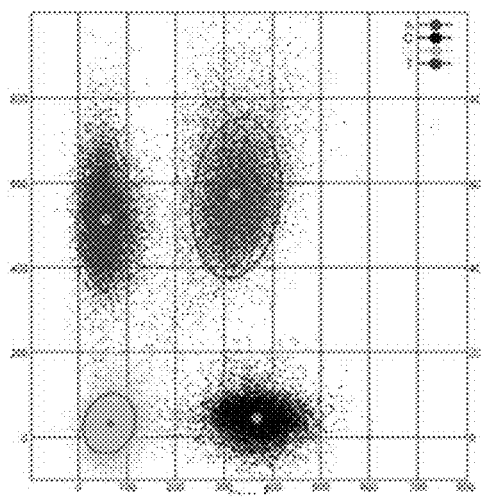
Figure 6C:
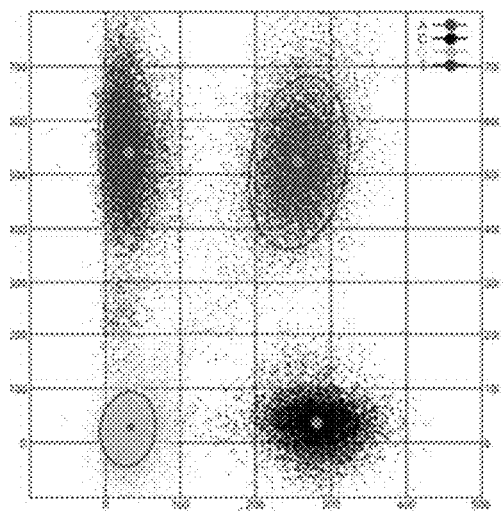
FIGS. 6C-6D are scatterplots illustrating the usability of ffA and ffC labeled with Dye I-3a where presented ratio of signals from ffC and ffT nucleotides after one dose of light exposure (C/T @ 1×) and ratio of appropriate signals after ten doses of exposure (C/T @ 10×/1×).
Figure 6D:
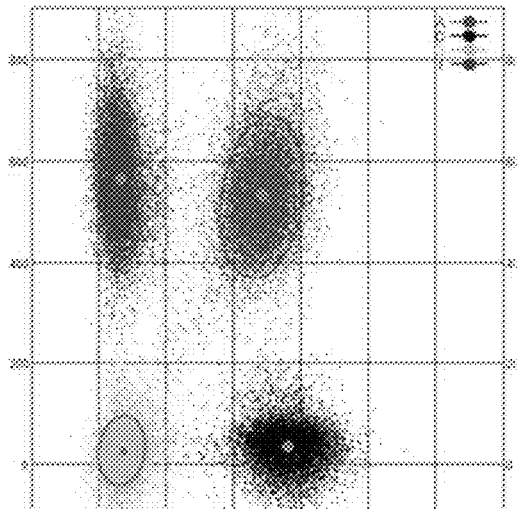
Figure 6E:
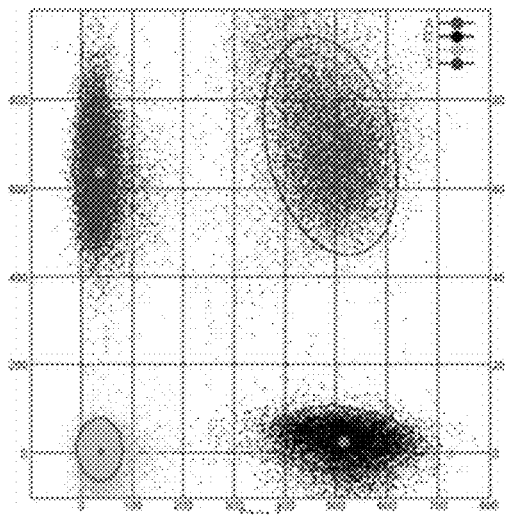
FIGS. 6E-6F are scatterplots illustrating the usability of ffA and ffC labeled with Dye II-1 where presented ratio of signals from ffC and ffT nucleotides after one dose of light exposure (C/T @ 1×) and ratio of appropriate signals after ten doses of exposure (C/T @ 10×/1×).
Figure 6F:
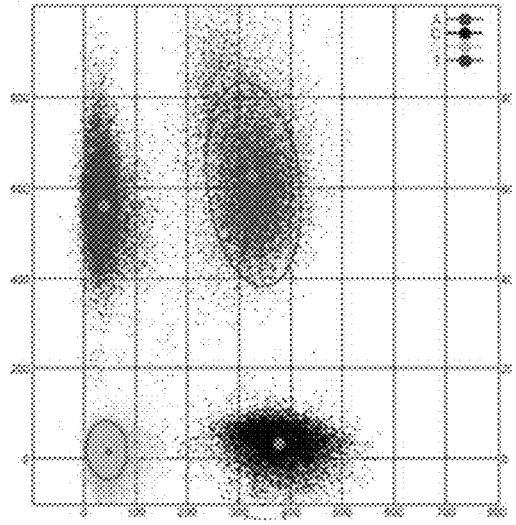
Figure 6G:
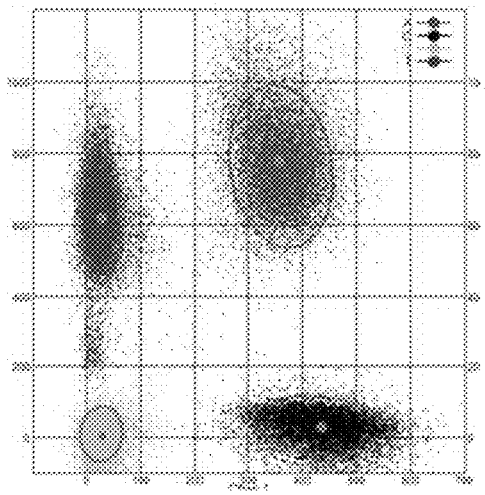
FIGS. 6G-6H are scatterplots illustrating the usability of ffA and ffC labeled with Dye II-8 where presented ratio of signals from ffC and ffT nucleotides after one dose of light exposure (C/T @ 1×) and ratio of appropriate signals after ten doses of exposure (C/T @ 10×/1×).
Figure 6H:
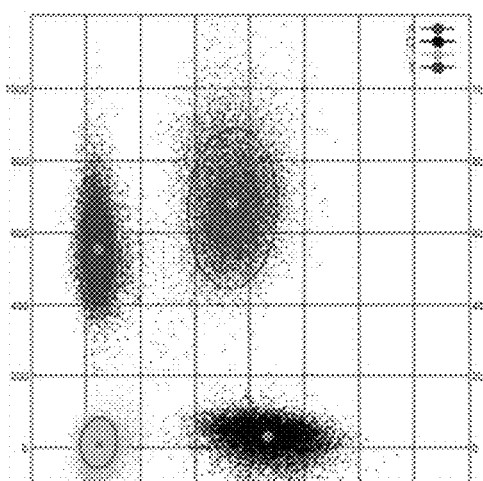

FIGS. 5A-5C illustrate the sequencing metrics when the ffAs and ffCs used in the Miseq® sequencing platform are labeled with Dye II-1 or Dye II-8 as compared to the ffNs labeled with the standard dye set, when different dosage of light were used (1×, 3×, 5×, 7.5× and 10×). In particular, the following ffNs were used: ffA-sPA-BL-Dye II-1 (1.65 uM)+ffA-sPA-BL-NR550S0 (0.35 uM); ffC-sPA-Dye II-1 (1.5 uM)+ffC-LN3-SO7181 (0.5 uM); ffA-BL-Dye II-8 (1.8 uM)+ffA-sPA-BL-NR550S0 (0.2 uM); ffC-sPA-Dye II-8 (1.5 uM)+ffC-LN3-SO7181 (0.5 uM). ffT is ffT-LN3-AF550POPOS0 used at 1 uM, and G is unlabeled. For the ffNs labeled with standard dye set, ffC-sPA-Reference Dye A and ffA-BL-Reference Dye A were used. An DNA polymerase Pol 1901 was used for incorporation of the ffNs at 90 ug/ml final concentration. It was observed that the ffA/ffC labeled with Dyes II-1 and II-8 provided comparable sequencing results to those labeled with Reference Dye A at 1× and 3× light dosage.

FIGS. 6A-6H are scatterplots of the ffA/ffC labeled with Dyes I-4a, I-3a, I-1 and I-8 as described above respectively at 1× and 10× light dosage. ffT is ffT-LN3-AF550POPOS0 used at 1 uM, and G was unlabeled (dark G). Pol 1901 was used in the incorporation buffer at 90 ug/ml final concentration. Blue exposure (Chanel 1) 500 ms, Green exposure (Chanel 2) 1000 ms; Scanned in Scanning mix. In each of FIGS. 6A-6H, "G" nucleotide is shown as the lower left cloud ("dark G"). The signal from a mixture of "A" nucleotide labeled by the new blue dyes described herein and a green dye (NR550S0) is shown as the upper right cloud. The signal from the "T" nucleotide labelled with dye AF550POPOS0 is indicated by the upper left cloud, and signal from a mixture of "C" nucleotide labelled by the new blue dyes described herein and another dye S07181 is indicated by the lower right cloud. The X-axis shows the signal intensity for one (Blue) channel and the Y-axis shows the signal intensity for the other (Green) channel. The chemical structures of AF550POPOS0, and NR550S0 are disclosed in PCT Publication Nos. WO2018060482A1, WO2017051201A1, and WO2014135221A1 respectively, all of which are incorporated by references.

FIGS. 6A-6H illustrating the usability of ffA and ffC labeled with the new blue dyes (Dyes I-4a, I-3a, Dye II-1 or Dye II-8) where presented ratio of signals from ffC and ffT nucleotides after one dose of light exposure (C/T @ 1×) and ratio of appropriate signals after ten doses of exposure (C/T @ 10×/1×). This parameter measures how much the ffC fluorescent intensity is moving in relation to that of the ffT at higher dosages of light, which is indicative of photobleaching. FIGS. 6A-6H each shows that the ffC conjugates labelled with the new dye described herein provides sufficient signal intensities and great cloud separation.

What is claimed is:

1. A compound of Formula (I), or a salt or mesomeric form thereof:

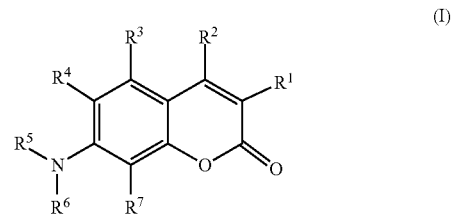

wherein $R^1$ is

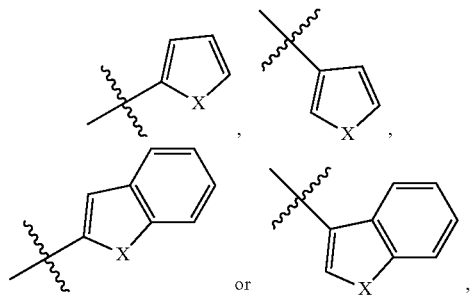

each optionally substituted with one or more substituents independently selected from the group consisting of carboxyl, $-C(O)NR^bR^c$, $-C(O)OR^d$, $C_1$-$C_6$ alkyl, substituted $C_1$-$C_6$ alkyl, halo, optionally substituted amino, hydroxy, sulfo, sulfonate, sulfate, N-sulfonamido, and S-sulfonamido;

$R^2$ is H, optionally substituted $C_1$-$C_6$ alkyl, or phenyl optionally substituted with one or more substituents selected from the group consisting of carboxyl, $-C(O)NR^bR^c$, $-C(O)OR^d$, optionally substituted $C_1$-$C_6$ alkyl, halo, cyano, nitro, sulfonyl, sulfino, sulfo, sulfonate, optionally substituted amino, and hydroxy;

each $R^3$, $R^4$ and $R^7$ is independently H, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, ($C_1$-$C_6$ alkoxy)($C_1$-$C_6$ alkyl), optionally substituted amino, halo, cyano, hydroxy, nitro, sulfonyl, sulfino, sulfo, sulfonate, S-sulfonamido, N-sulfonamido, optionally substituted $C_3$-$C_{10}$ carbocyclyl, or optionally substituted 3 to 10 membered heterocyclyl;

$R^5$ is H and $R^6$ is H, $C_1$-$C_6$ alkyl, or substituted $C_1$-$C_6$ alkyl, or both $R^5$ and $R^6$ are $C_1$-$C_6$ alkyl, or $R^5$ and $R^6$ together with the nitrogen atom to which they are attached form an optionally substituted 4 to 10 membered heterocyclyl;

X is O, S, or $NR^a$;

$R^a$ is H or $C_1$-$C_6$ alkyl;

each $R^b$ and $R^c$ is independently H, $C_1$-$C_6$ alkyl, or substituted $C_1$-$C_6$ alkyl; and $R^d$ is optionally substituted $C_1$-$C_6$ alkyl or optionally substituted phenyl; provided that at least one of $R^6$, or the optionally substituted 4 to 10 membered heterocyclyl formed from $R^5$ and $R^6$ and the nitrogen atom to which they are attached, comprises a carboxyl or —C(O)OR$^d$; or $R^1$ comprises a carboxyl or —C(O)OR$^d$.

2. The compound of claim 1, wherein $R^1$ is

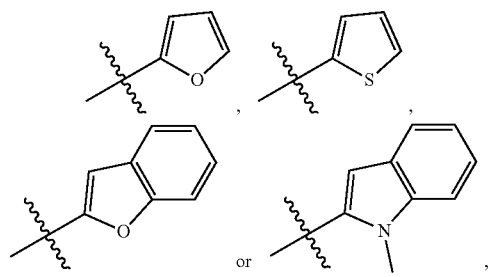

each substituted with carboxyl.

3. The compound of claim 2, wherein $R^1$ is

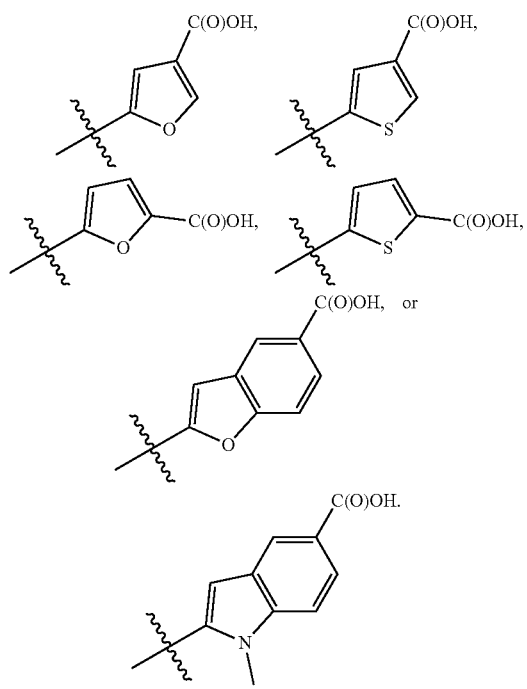

4. The compound of claim 1, wherein each of $R^5$ and $R^6$ is $C_1$-$C_6$ alkyl.

5. The compound of claim 1, wherein $R^5$ is H and $R^6$ is substituted $C_1$-$C_6$ alkyl.

6. The compound of claim 5, wherein the $C_1$-$C_6$ alkyl is substituted with carboxyl, —C(O)OR$^d$, sulfo (—SO$_3$H), sulfonate (—SO$_3^-$), sulfate (—O—SO$_3^-$) or an optionally substituted amino.

7. The compound of claim 1, wherein $R^1$ is

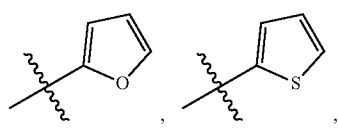

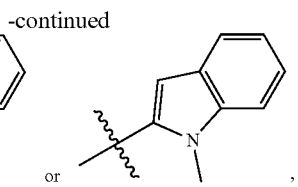

each unsubstituted or substituted with sulfo (—SO$_3$H).

8. The compound of claim 7, wherein $R^5$ is H and $R^6$ is $C_1$-$C_6$ alkyl substituted with carboxyl or —C(O)OR$^d$.

9. The compound of claim 7, wherein $R^5$ and $R^6$ and the nitrogen atom to which they are attached form a 5 or 6 membered heterocyclyl substituted with carboxyl or —C(O)OR$^d$.

10. The compound of claim 1, wherein $R^2$ is H.

11. The compound of claim 1, wherein $R^2$ is $C_1$-$C_6$ alkyl.

12. The compound of claim 1, wherein each of $R^3$, $R^4$ and $R^7$ is H.

13. The compound of claim 1, selected from the group consisting of:

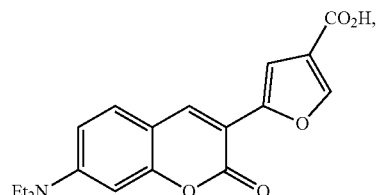

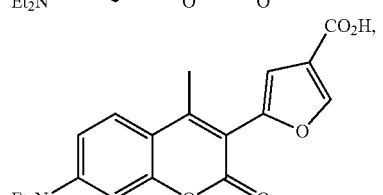

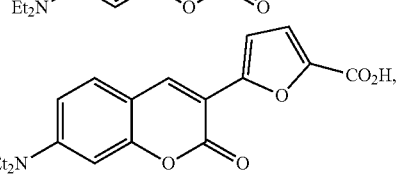

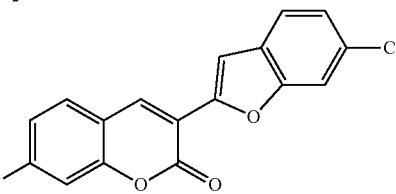

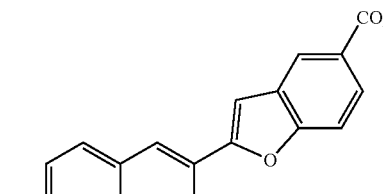

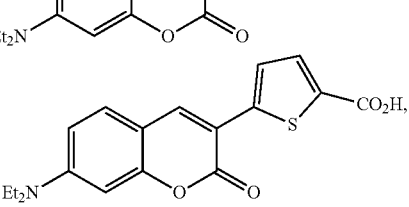

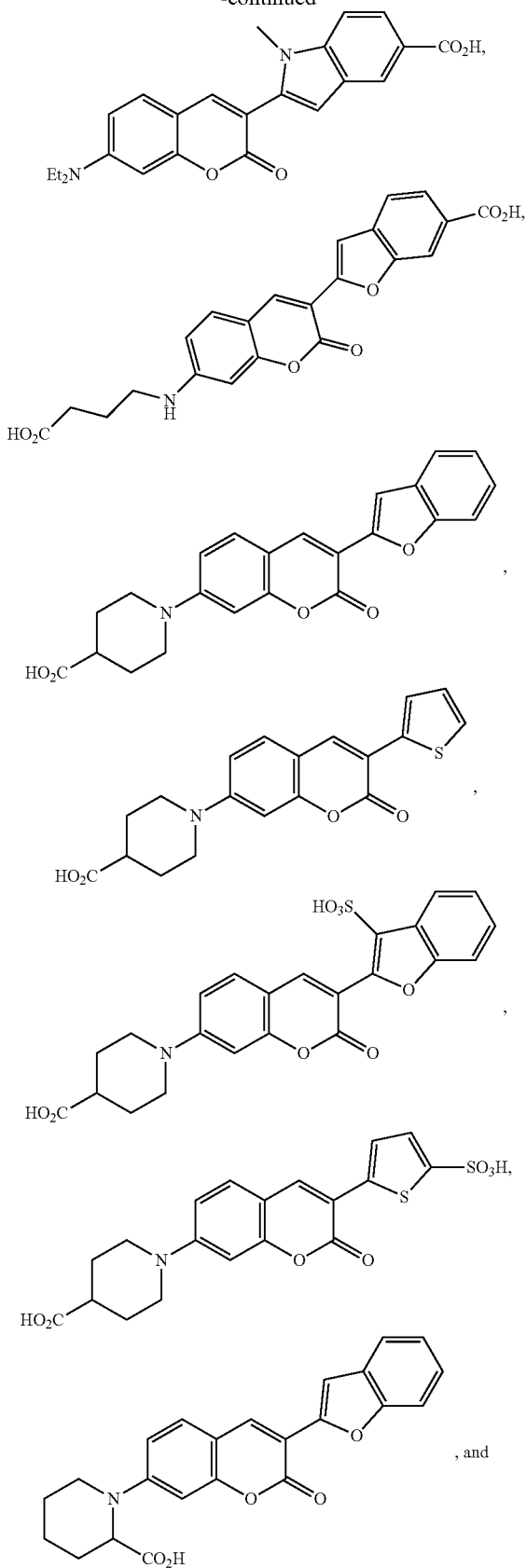

salts and mesomeric forms thereof.

14. A nucleotide or oligonucleotide labeled with a compound according to claim 1, wherein the compound is attached the nucleotide or oligonucleotide via a carboxyl group of the compound.

15. The labeled nucleotide or oligonucleotide of claim 14, wherein the compound is attached to the C5 position of a pyrimidine base or the C7 position of a 7-deaza purine base through a linker moiety.

16. The labeled nucleotide or oligonucleotide of claim 14, further comprising a 3' OH blocking group covalently attached to the ribose or deoxyribose sugar of the nucleotide.

17. The nucleotide or oligonucleotide of claim 14, wherein the nucleotide or oligonucleotide is an oligonucleotide hybridized to at least a portion of a target polynucleotide, and wherein the target polynucleotide is immobilized on a solid support.

18. A kit comprising a first type of labeled nucleotide according to claim 14.

19. The kit of claim 18, wherein the kit comprises four types of nucleotides, wherein each of the first, the second, the third, and the fourth type of nucleotides is labeled with a different compound, wherein each label has a distinct absorbance maximum that is distinguishable from the other labels.

20. The kit of claim 18, wherein the kit comprises four types of nucleotides, the second type of nucleotide is labeled with a second label, the third type of nucleotide is labeled with a third label, and the fourth type of nucleotide is unlabeled (dark).

21. The kit of claim 18, wherein the kit comprises four types of nucleotides, the second type of nucleotide is labeled with a second label, the third type of nucleotide is labeled with a mixture of two labels, and the fourth type of nucleotide is unlabeled (dark).

22. A method of determining the sequence of a single-stranded target polynucleotide, comprising:
  (a) contacting a primer polynucleotide/target polynucleotide complex with one or more different types of nucleotides, wherein at least one type of nucleotides is the label nucleotide of claim 15, wherein each nucleotide comprises a 3' hydroxy blocking group covalently attached to the deoxyribose sugar of the nucleotide, and wherein the primer polynucleotide is complementary to at least a portion of the target polynucleotide;
  (b) incorporating a labeled nucleotide into the primer polynucleotide;
  (c) performing one or more fluorescent measurements to determine the identity of the incorporated nucleotide; and
  (d) removing the label and the 3' blocking group from the nucleotide incorporated into the primer polynucleotide.

23. The method of claim 22, further comprising (e) washing the removed label and the 3' blocking group away from the primer polynucleotide, and wherein steps (a) to (e) are repeated until a sequence of at least a portion of the template polynucleotide strand is determined.

24. The method of claim 22, wherein the label and the 3' blocking group from the nucleotide incorporated into the primer polynucleotide are removed in a single chemical reaction.

25. The method of claim 22, wherein the method is performed on an automated sequencing instrument, and wherein the automated sequencing instrument comprises two light sources operating at different wavelengths.

* * * * *